(12) United States Patent
Brown et al.

(10) Patent No.: US 8,853,258 B2
(45) Date of Patent: Oct. 7, 2014

(54) C-LINKED HYDROXAMIC ACID DERIVATIVES USEFUL AS ANTIBACTERIAL AGENTS

(75) Inventors: Matthew Frank Brown, Stonington, CT (US); Anthony Marfat, Mystic, CT (US); Michael Joseph Melnick, Portage, MI (US); Usa Reilly, West Haven, CT (US)

(73) Assignee: Pfizer Inc., New York, NY (US)

(*) Notice: Subject to any disclaimer, the term of this patent is extended or adjusted under 35 U.S.C. 154(b) by 118 days.

(21) Appl. No.: 13/501,776

(22) PCT Filed: Oct. 4, 2010

(86) PCT No.: PCT/IB2010/054463
§ 371 (c)(1),
(2), (4) Date: Apr. 13, 2012

(87) PCT Pub. No.: WO2011/045703
PCT Pub. Date: Apr. 21, 2011

(65) Prior Publication Data
US 2012/0202777 A1     Aug. 9, 2012

Related U.S. Application Data

(60) Provisional application No. 61/251,016, filed on Oct. 13, 2009.

(51) Int. Cl.
| | |
|---|---|
| *A61K 31/382* | (2006.01) |
| *A61K 31/47* | (2006.01) |
| *A61K 31/661* | (2006.01) |
| *C07D 215/06* | (2006.01) |
| *C07C 317/44* | (2006.01) |
| *C07D 231/56* | (2006.01) |
| *C07F 9/12* | (2006.01) |
| *C07C 323/65* | (2006.01) |
| *C07C 317/46* | (2006.01) |
| *C07D 213/56* | (2006.01) |
| *C07C 317/48* | (2006.01) |
| *C07D 263/08* | (2006.01) |
| *C07D 295/03* | (2006.01) |
| *C07D 263/20* | (2006.01) |
| *C07D 335/02* | (2006.01) |
| *C07D 213/30* | (2006.01) |

(52) U.S. Cl.
CPC ............ *C07C 317/44* (2013.01); *C07D 231/56* (2013.01); *C07F 9/12* (2013.01); *C07C 323/65* (2013.01); *C07C 317/46* (2013.01); *C07C 2101/08* (2013.01); *C07D 213/56* (2013.01); *C07C 317/48* (2013.01); *C07D 263/08* (2013.01); *C07D 295/03* (2013.01); *C07D 263/20* (2013.01); *C07D 215/06* (2013.01); *C07D 335/02* (2013.01); *C07D 213/30* (2013.01); *C07C 2101/18* (2013.01); *C07C 2101/02* (2013.01)
USPC ............ 514/432; 514/311; 514/119; 546/152

(58) Field of Classification Search
None
See application file for complete search history.

(56) References Cited

FOREIGN PATENT DOCUMENTS

| WO | WO2007069020 | 6/2007 | |
|---|---|---|---|
| WO | WO2009008905 | 1/2009 | ............ C07C 259/06 |

OTHER PUBLICATIONS

Rappé et al., Annual Review of Microbiology, 2003, vol. 57, pp. 369-394.*
Apfel, C., et al., "Hydroxamic Acid derivatives a Potent Peptide Deformylase Inhibitors and Antibacterial Agents", Journal of Medicinal Chemistry, May 20, 2000, pp. 2324-2331, 43.
PCT International Search Report for PCT/IB2010/054463, mailed Apr. 11, 2011, 5 pages.
PCT International Written Opinion for PCT/IB2010/054463, mailed Apr. 11, 2011, 9 pages.
Rice, L.B., et al., "Unmet Medical Needs in Antibacterial Therapy", BioChemical Pharmacology, Mar. 30, 2006, pp. 991-995, 71(7).
Gennadios, H.A., et al., "Mechanistic Inferences from the Binding of Ligands to LpxC, a Metal-Dependent Deacetylase", Biochemistry, 2006, pp. 7940-7948, vol. 45.
Raetz, C.R.H., et al., "Lipid A Modification systems in Gram-Negative Bacteria", Annual Review Biochem, Jun. 2007, pp. 295-329, vol. 76.
Kwok, A., et al., "*Helicobacter pylori* eradication therapy: indications, efficacy and safety", Expert Opinion Drug Safety, May 2008, pp. 271-281, 7(3).
Andrews, Jennifer M., "Determination of minimum inhibitory concentrations", Journal of Antimicrobial Chemotherapy, 2001, pp. 5-16, 48(Suppl. S1).

* cited by examiner

*Primary Examiner* — Savitha Rao
*Assistant Examiner* — Gregg Polansky
(74) *Attorney, Agent, or Firm* — John A. Wichtowski

(57) ABSTRACT

The present invention is directed to a new class of hydroxamic acid derivatives of Formula I,

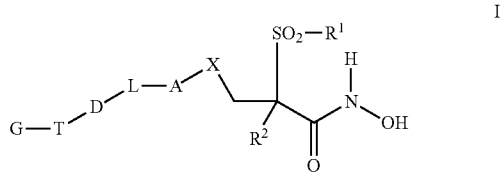

wherein the variables G, T, D, L, A, X, $R^1$ and $R^2$ are as described hereinabove, and their use as LpxC inhibitors, and more specifically their use to treat bacterial infections.

5 Claims, No Drawings

C-LINKED HYDROXAMIC ACID DERIVATIVES USEFUL AS ANTIBACTERIAL AGENTS

This application is a National Stage filing of PCT/IB2010/054463 filed Oct. 4, 2010, which claims priority to U.S. Provisional Patent Application No. 61/251,016 filed Oct. 13, 2009 the disclosures of which are hereby incorporated by reference in its entirety.

FIELD OF THE INVENTION

This invention relates to novel hydroxamic acid derivatives that are useful for the treatment of bacterial infections, especially Gram-negative infections. The invention also relates to methods of using such compounds in the treatment of bacterial infections in mammals, and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Enterobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most gram-negative bacteria. LpxC is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC [UDP-3-O—(R-3-hydroxymyristoyl)-GlcNAc deacetylase] with low nM affinity have been reported (Biochemistry 45: 7940-48, 2006).

SUMMARY OF THE INVENTION

A new class of LpxC inhibitors has been discovered. These compounds, or their pharmaceutical salts, can be represented by Formula I below:

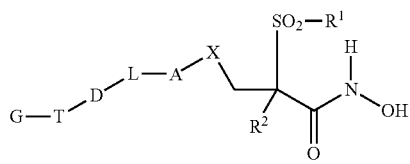

in which
$R^1$ is represented by $C_1$-$C_3$ alkyl;
$R^2$ is represented by hydrogen or $C_1$-$C_3$ alkyl;
X is represented $CH_2$, O, NH, S or $SO_2$,
A is represented by phenyl or a 6-membered heteroaryl as depicted below:

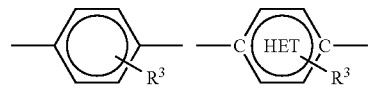

$R^3$ is independently selected from the group consisting of hydrogen, halogen, nitro, cyano, hydroxy, amino, ($C_1$-$C_6$) alkyl optionally substituted, ($C_1$-$C_6$)alkoxy optionally substituted, trifluoromethyl, and trifluoromethoxy;
L is absent, or is represented by S, SH, OH, —$(CH_2)_p$—O—$(CH_2)_n$—, —$(CH_2)_p$—O—$(CH_2)_z$—O—$(CH_2)_n$—, S—$(CH_2)_z$, or $(CH_2)_n$—S;
n is represented by an integer ranging from 0 to 3;
p is represented by an integer ranging from 0 to 3;
z is represented by an integer from 1 to 3;
D is absent, or is represented by a substituent selected from the group consisting of:
  i) ($C_3$-$C_{10}$)cycloalkyl, optionally substituted,
  ii) ($C_3$-$C_{10}$)cycloalkyl ($C_1$-$C_6$)alkyl, in which the alkyl and cycloalkyl moieties may each be optionally substituted,
  iii) ($C_6$-$C_{10}$)aryl optionally substituted,
  iv) ($C_6$-$C_{10}$)aryl ($C_1$-$C_6$)alkyl, in which the alkyl and aryl moieties may each be optionally substituted,
  v) heteroaryl, optionally substituted,
  vi) heteroaryl($C_1$-$C_6$)alkyl, in which the heteroaryl and alkyl moieties may each be optionally substituted,
  vii) heterocyclic, optionally substituted, and;
  viii) heterocyclic($C_1$-$C_6$)alkyl, in which the alkyl and heterocyclic moieties may each be optionally substituted;
T is absent, or is represented by —$(CH_2)_z$—, —$(CH_2)_n$—, —C(O)—$(CH_2)_p$—, O—$(CH_2)_z$—, —$(CH_2)_z$—O—, or —O—$(CH_2)_p$—C(O)—$(CH_2)_n$—;
G is absent, or is represented by a substituent selected from the group consisting of:
  i) ($C_3$-$C_{10}$)cycloalkyl, optionally substituted;
  ii) ($C_6$-$C_{10}$)aryl optionally substituted;
  iii) heteroaryl, optionally substituted, and;
  iv) heterocyclic, optionally substituted; with the proviso that:
    a) at least one of D or L must be present
    b) if D is absent, then T and G are also absent.

The compounds of Formula I exhibit antibacterial activity, especially against Gram-negative organisms. They may be used to treat bacterial infections in mammals, especially humans. The compounds may also be used for veterinary applications, such as treating infections in livestock and companion animals.

The compounds of Formula I are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation and solutions/suspensions for oral ingestion.

DETAILED DESCRIPTION OF THE INVENTION

The headings within this document are only being utilized to expedite its review by the reader. They should not be construed as limiting the invention or claims in any manner.

DEFINITIONS AND EXEMPLIFICATION

As used throughout this application, including the claims, the following terms have the meanings defined below, unless specifically indicated otherwise. The plural and singular should be treated as interchangeable, other than the indication of number:

a. "$C_1$-$C_3$ alkyl" refers to a branched or straight chained alkyl group containing from 1 to 3 carbon atoms, such as methyl, ethyl, n-propyl, or isopropyl, etc.

b. "6-membered heteroaryl" refers to an aromatic 6 membered ring that may contain 1, 2, 3, or 4 nitrogen atoms Examples of such rings include pyridyl, pyridazinyl, pyrimidinyl, and pryazinyl.

c. "optionally substituted 6-membered heteroaryl" refers to a 6-membered heteroaryl ring, as described above, in which up to 3 carbon atoms of any such ring may be substituted with a non-hydrogen substituent, each substituent is independently selected from the group consisting of halogen, nitro, cyano, hydroxy, amino, ($C_1$-$C_6$)alkyl optionally substituted, ($C_1$-$C_6$)alkoxy optionally substituted, trifluoromethyl, and trifluoromethoxy.

d. "halogen" refers to a chlorine, fluorine, iodine, or bromine atom.

e. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, etc.

f. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc; which may be unsubstituted or optionally further substituted with halogen, hydroxy, thiol or amino.

g. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, cyano, —O—$R^a$, and —S$R^aR^b$ in which $R^a$ and $R^b$ are each independently represented by hydrogen or $C_1$-$C_6$ alkyl.

h. "($C_3$-$C_{10}$) cycloalkyl" refers to a saturated or partially saturated monocyclic, bicyclic, bridged bicyclic or tricyclic alkyl radical wherein each cyclic moiety has 3 to 10 carbon atoms. Examples of such cycloalkyl radicals include cyclopropyl, cyclobutyl, cyclopentyl, cyclohexyl, cyclooctyl, and the like.

i. "($C_3$-$C_{10}$) cycloalkyl" optionally substituted refers to a ($C_3$-$C_{10}$) cycloalkyl moiety as described above. Such a cycloalkyl group may be optionally substituted, in which up to 4 hydrogen atoms are replaced by a substituent selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, oxo, —SO$_2$NR$^4$, —(CH$_2$)$_m$—N—C(O)—R$^4$, —(CH$_2$)$_m$—C(O)—N—R$^4$, —C(O)—R$^4$, —C(O)—O—R$^4$, —SR$^4$, —SO$_2$R$^4$ and —NR$^4$R$^5$, in which R$^4$ and R$^5$ are each independently represented by hydrogen or $C_1$-$C_6$ alkyl, which may be optionally substituted as defined above, and m is 0-4.

j. "($C_6$-$C_1$)aryl" means a cyclic, aromatic hydrocarbon containing from 6 to 10 carbon atoms. Examples of such aryl groups include phenyl, naphthyl, etc.

k. "($C_6$-$C_{10}$)aryl" optionally substituted means a cyclic, aromatic hydrocarbon as defined above. Such an aryl moiety may be optionally substituted with up to 4 non-hydrogen substituents, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, oxo, —SO$_2$NR$^4$, —(CH$_2$)$_m$—N—C(O)—R$^4$, —(CH$_2$)$_m$—C(O)—N—R$^4$, —C(O)—R$^4$, —C(O)—O—R$^4$, —SR$^4$, —SO$_2$R$^4$ and —NR$^4$R$^5$, in which m, R$^4$ and R$^5$ are as defined above. These substituents may be the same or different and may be located at any position of the ring, that is chemically permissible.

l. "heteroaryl" refers to an aromatic ring having one, or more, heteroatoms selected from oxygen, nitrogen and sulfur. More specifically, it refers to a 5- or 6-membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

m. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, nitro, hydroxy, ($C_1$-$C_6$)alkyl optionally substituted, ($C_1$-$C_6$)alkoxy optionally substituted, trifluoromethyl, trifluoromethoxy, phosphate, oxo, SO$_2$NR$^4$, —(CH$_2$)$_m$—N—C(O)—R$^4$, —(CH$_2$)$_m$—C(O)—N—R$^4$, —C(O)—R$^4$, —C(O)—O—R$^4$, —SR$^4$, —SO$_2$R$^4$ and —NR$^4$R$^5$, in which m, R$^4$ and R$^5$ are as defined above. These substituents may be the same or different and may be located at any position of the ring, that is chemically permissible.

n. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, thiomorpholinyl, tetrahydropyrimidinyl, dioxolinyl, octahydrobenzofuranyl, octahydrobenzimidazolyl, and octahydrobenzothiazolyl.

o. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, nitro, hydroxy, $(C_1-C_6)$alkyl optionally substituted, $(C_1-C_6)$alkoxy optionally substituted, trifluoromethyl, trifluoromethoxy, phosphate, oxo, $SO_2NR^4$, $—(CH_2)_m—N—C(O)—R^4$, $—(CH_2)_m—C(O)—N—R^4$, $—C(O)—R^4$, $—C(O)—O—R^4$, $—SR^4$, $—SO_2R^4$ and $—NR^4R^5$, in which m, $R^4$ and $R^5$ are as defined above. These substituents may be the same or different and may be located at any position of the ring that is chemically permissible. Any nitrogen atom within such a heterocyclic ring may optionally be substituted with $(C_1-C_6)$ alkyl, if such substitution is chemically permissible.

p. "therapeutically effective amount" refers to an amount of a compound of Formula I that, when administered to a patient, provides the desired effect; i.e., lessening in the severity of the symptoms associated with a bacterial infection, decreasing the number of bacteria in the affected tissue, and/or preventing bacteria in the affected tissue from increasing in number.

q. "patient" refers to warm blooded animals such as, for example, guinea pigs, mice, rats, gerbils, cats, rabbits, dogs, monkeys, chimpanzees, and humans.

r. "treat" refers to the ability of the compounds to relieve, alleviate or slow the progression of the patient's bacterial infection (or condition) or any tissue damage associated with the disease.

s. "pharmaceutically acceptable" indicates that the substance or composition must be compatible chemically and/or toxicologically, with the other ingredients comprising a formulation, and/or the mammal being treated therewith. "isomer" means "stereoisomer" and "geometric isomer" as defined below. "stereoisomer" means compounds that possess one or more chiral centers and each center may exist in the R or S configuration. Stereoisomers include all diastereomeric, enantiomeric and epimeric forms as well as racemates and mixtures thereof.

u. "geometric isomer" means compounds that may exist in cis, trans, anti, entgegen (E), and zusammen (Z) forms as well as mixtures thereof.

v. Compounds of "Formula I", "formula I" and "compounds of the invention" are being used interchangeably thru-out the application and should be treated as synonyms.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare pharmaceutically acceptable base salts of those compounds of the compounds of the invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

All of the compounds of Formula I contain a sulfonyl moiety as depicted below:

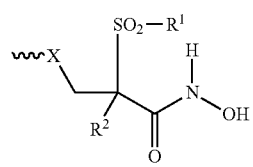

This sulfonyl moiety will always be substituted with a lower alky moiety. Typically it will be methyl. The carbon atom adjacent to the sulfonyl may optionally be substituted, as represented by $R^2$. Typically both $R^1$ and $R^2$ will be methyl. The linker represented by X will typically be methylene.

As is readily apparent to one skilled in the art, the carbon adjacent to the sulfonyl moiety is a chiral center. Therefore the compounds can exist as the racemate, as the S enantiomer, or as the R enantiomer. In a further embodiment, the compounds may be prepared and administered as the R-enantiomer, as depicted below:

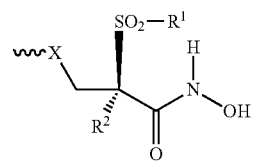

All of the compounds of Formula I contain either a phenyl ring or a 6-membered heteroaryl ring, as depicted by A. Either the phenyl ring or the heteroaryl ring may be optionally substituted as described above by the $R^3$ substituent. $R^3$ may represent up to 4-non-hydrogen substituents when A is phenyl. When A is a 6-membered heteroaryl, $R^3$ may represent up to 3 non-hydrogen substituents. These substituents may be the same or different and are listed above.

When A is heteroaryl, it will be connected to the rest of the molecule via carbon atoms as depicted above. When A is a heteroaryl, it will typically be pyridyl, pyrimidyl, or pyridazinyl.

Examples of such pyridyl's include:

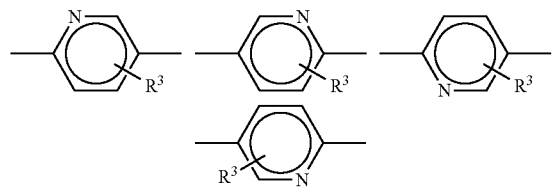

Typically these pyridyl rings will be unsubstituted or mono-substituted with $C_1$-$C_6$ lower alkyl optionally substituted, hydroxy or amino.

All of the compounds may also contain one of the substituents as defined by D. Alternatively, D may be absent, along with T and G, and the tail of the molecule may be one of the ether or thioether moieties defined by L as discussed below.

D, if present, may be cycloalkyl, aryl, heteroaryl, or heterocyclic. Alternatively, D may be (cycloalkyl)alkyl, (heteroaryl)alkyl, (aryl)alkyl, or heterocyclic(alkyl), etc. Any of theses ring systems may be optionally substituted with up to 4 non-hydrogen substituents from the list specified above. These substituents may be the same or different. Such substitution may occur wherever chemically permissible. For example, in a heterocyclic system, a nitrogen atom may be substituted with an alkyl moiety. In an aromatic system, substitution may only occur on a carbon atom.

If D is (cycloalkyl)alkyl, (heteroaryl)alkyl, etc., the alkyl moiety will be bonded to the phenyl or heteroaryl ring represented by A. This alkylene moiety may be optionally substituted with up to 6-non-hydrogen atoms as described above. These substituents may be the same or different.

Typically, D will either be phenyl, or pyridyl. If D represents phenyl; then it will be unsubstituted, or substituted with halogen, amino, nitro, phosphate, or hydroxyl. If pyridyl, D will be typically be unsubstituted.

The presence of L is optional. The moieties represented by A and D may be bonded to each other, or L may serve as a linker. Alternatively, L may serve as the tail of the molecule, when D, T and G are absent. Most typically, L will be absent.

The presence of T is optional. It may serve as a linker between the rings that define D and G. Typically T will be absent.

The presence of G in the molecule is also optional. It may be absent. Alternatively, it may be represented by a heteroaryl moiety, a heterocyclic moiety, $(C_3-C_{10})$ cycloalkyl, or $(C_6-C_{10})$ aryl. Any of these moieties may be unsubstituted or optionally substituted. They may be substituted with up to 4-non-hydrogen substituents. These substituents may be the same or different. Such substitution may occur wherever chemically permissible. Typically, G will be absent.

More specific embodiments of the invention include compounds of Formula I in which:
a) $R^1$ is methyl;
b) $R^1$ and $R^2$ are each methyl;
c) X is $CH_2$;
d) $R^1$ and $R^2$ are each methyl and X is $CH_2$;
e) $R^1$ and $R^2$ are each methyl, X is $CH_2$ and A is phenyl or pyridyl;
f) $R^1$ and $R^2$ are each methyl, X is $CH_2$ and A is phenyl or pyridyl in which $R^3$ is hydrogen;
g) $R^1$ and $R^2$ are each methyl, X is $CH_2$, A and D are both optionally substituted phenyl, L, T and G are all absent;
h) $R^1$ and $R^2$ are each methyl, X is $CH_2$, L, T and G are each absent, A and D are each independently selected from the group consisting of optionally substituted pyridyl and optionally substituted phenyl, and;
i) $R^1$ and $R^2$ are each methyl, X is $CH_2$, D, T and G are each absent, and L is present and as defined above.

Synthesis

The compounds of Formula I can be prepared by a variety of methods that are analogously known in the art. The reactions schemes presented below illustrate one method for preparing these compounds. Others, including modifications thereof will be readily apparent to one skilled in the art.

Scheme A provides an overview of how to synthesize the compounds of Formula I in which X is $CH_2$, as depicted. For the generation of the phenyl or heteroaryl intermediate identified as structure 1, see Reaction Scheme B. In the compound of structure 1, Z will be represented by a suitable reactive group such as halogen, boronic acid or boronate ester, etc, depending upon the identity of D, T and G in the final product. Y will typically be represented by a hydroxyl group or the protected sulfonyl-containing moiety as depicted. "PG" is a protecting group such as a lower alkyl (as part of an ester) or a tetrahydropyranyl group (as part of a hydroxamate).

Scheme A

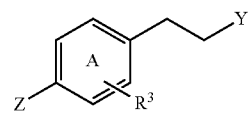

1

Y = OH or

—$CR_2(SO_2R^1)$—C(O)—O—PG

—$CR_2(SO_2R^1)$—C(O)—NH—OPG

| Scheme 1A<br>L absent<br>D and A linked via<br>C—C bond<br>G—T—D—$M^1$ | Scheme 1B<br>L present-<br>forms ether<br>or thioether<br>directly with at<br>least one of<br>D or A<br>G—T—D—L—$M^2$ | Scheme 1C<br>L absent D and<br>A linked via<br>C—N bond<br>G—T—D | Scheme 1D<br>L present<br>forms<br>C—C<br>bond with<br>A and D<br>G—T—D—L' |

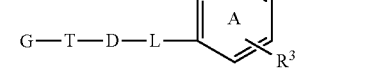

2

Scheme 2 | Hydroxamic Acid Formation

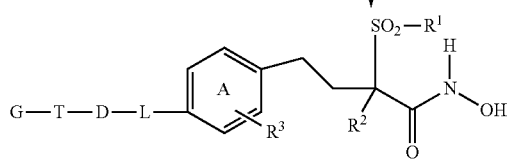

I

As depicted in Scheme A, the next step in the synthesis will depend upon the identity of D, T, G, and L in the final product. Four alternative reactions are depicted. If L is absent and the goal is to form a carbon-carbon bond then Scheme 1A should be chosen. This is appropriate for compounds in which D is aryl, arylalkyl, cycloalkyl, cycloalkylalkyl, C-linked heteroaryl, etc.

If L forms an ether or thioether with at least one of D or A, then Scheme 1B should be chosen. If L is absent and D is a heteroaryl or heterocyclic moiety and the bond will be with the heteroatom (i.e. C—N), then Scheme 1C should be chosen. Finally, if L is present and forms a carbon-carbon bond with both A and D (if present), then Scheme 1D should be utilized. The specifics of these reactions are discussed infra.

The final step in the synthesis is to incorporate the hydroxamic acid moiety into the molecule utilizing the methodologies depicted in Scheme 2 infra. As is readily apparent to one skilled in the art, the order in which the reactions are carried out is typically not critical. If desired, the hydroxamic acid moiety may be incorporated into the molecule and then the G-T-D-L moiety may be added. Further D, T or G may also be added separately. Such manipulations are readily apparent to one skilled in the art and can be carried out using standard techniques well known to medicinal chemists.

Scheme 1A is appropriate for the compounds in which L is absent and a C—C bond is desired. Thus this reaction will be used when D is any of cycloalkyl, cycloalkylalkyl, aryl, arylalkyl, heteroaryl, heteroarylalkyl, heterocyclic, heterocyclic alkyl, cycloalkyl, or cycloalkyl alkyl (any of which may be optionally substituted).

One of the starting materials will be an appropriately substituted phenyl or heteroaryl moiety as described by structure 1. $R^3$ will typically be represented by the same substituent as is desired in the final product. Z will be a halide, boronic acid, boronate ester or other appropriately reactive group. Y will be hydroxyl or the protected sulfonyl-containing moiety as depicted above. The other reactant, G-T-D-$M^1$, will be represented by the same moiety as desired in the final product except that it will be substituted by a halogen atom or metal such as magnesium, copper, or a boronate ester, etc. at the desired point of attachment to the aryl moiety "A".

The molecule may be assembled using any of a number of coupling reactions known in the art. For example, the Suzuki-Miyaura strategy may be used. In such a reaction $M^1$ will be a boronic acid/ester and Z will be a halogen atom or a triflate (or vice versa). Equivalent molar amounts of the reactants will be contacted in a solvent such as THF, dioxane, water, toluene, or an admixture thereof; in the presence of a transition metal catalyst such as palladium, or nickel (or resin bound catalyst) along with a base such as sodium carbonate, potassium carbonate, cesium fluoride or cesium carbonate. The reactants will be heated by microwave or other conventional technique till completed. Once completed the desired product may be isolated and recovered from the reaction and further purified as is known in the art. Alternatively the crude may be used in Step 2 described below.

Alternatively an Ullmann coupling strategy may be used. In such a reaction $M^1$ will be copper or nickel and Z will be a halogen. Equivalent amounts of the reactants will be contacted in an aprotic solvent such as ether, DMF, or DME and the reactants are heated to reaction completion. The desired product of structure 2 may be isolated and purified as is known in the art, or used as a crude mixture in the next step of the reaction.

Scheme 1B is appropriate for the compounds in which L is present and a C—O or C—S bond is desired (i.e. L is an ether or thioether linkage) between L and at least one of A or D. A Willamson/Ullmann ether coupling, Mitsunobu or alkylation reaction may be utilized to produce these derivatives. One of the starting materials will be an appropriately substituted phenyl or heteroaryl moiety as described by structure 1. $R^3$ will typically be represented by the same substituent as is desired in the final product. Z will be halide, boronic acid, hydroxyl, etc. and Y will be hydroxyl or the protected sulfonyl moiety as depicted above. The other reactant, G-T-D-L-$M^2$, will be represented by the same moiety as desired in the final product, except that it will be substituted by a hydroxyl function at the desired point of attachment to the aryl moiety 'A'. If a thioether is desired, G-T-D-L-$M^2$ will be an appropriately substituted disulfide moiety. The Ullmann ether reaction can be carried out in the presence of copper salts. If a Williamson ether approach is used, then equivalent amounts of the reactants will be contacted in an aprotic solvent such as dioxane in the presence or absence of a phase transfer catalyst such as 18-crown-6. A base such as potassium hydroxide, sodium t-butoxide or sodium methoxide will typically be added as well. The reactants will be heated by microwave or other conventional technique to reaction completion. The desired product of structure 2 may be isolated and purified as is known in the art, or used as a crude mixture in the next step of the reaction.

Scheme IC is appropriate for those compounds in which L is absent and a carbon-nitrogen bond is desired between the carbon of the heteroaryl moiety, "A", and a nitrogen atom of the D moiety. This reaction will be used when D is any of heteroaryl or heterocyclic (either of which may be optionally substituted). One of the starting materials will be an appropriately substituted phenyl or heteroaryl moiety as described by structure 1. $R^3$ will typically be represented by the same substituent as is desired in the final product. Z will be a boronic acid, boronate ester or other appropriately reactive group. Y will be hydroxyl or the protected sulfonyl moiety as depicted above. The other reactant, G-T-D, will be represented by the same moiety as desired in the final product.

The carbon-nitrogen bond may be formed using a Buchwald-Hartwig cross-coupling or Ullmann strategy similar to that described above. Equivalent amounts of the reactants will be contacted in an aprotic solvent such as ether, dimethylformamide, or dimethyoxyethane in the presence of a source of copper, such as copper acetate, and a base such as pyridine or catalyst such as a palladium complex. The reaction will be allowed to proceed to completion and the desired product of structure 2 may be isolated and purified as is known in the art, or used as crude in the next step of the reaction.

Scheme 1D is appropriate for compounds in which L is present and forms a carbon-carbon bond with A and D (if D is present). One of the starting materials will be the derivative of structure 1 as described above in Scheme 1A in which $R^3$ will be represented by the same substituent as is desired in the final product and Y will be hydroxyl or the protected sulfonyl moiety depicted above. Z will be halide, boronic acid, boronate ester, or other appropriately reactive group. The other reactant, G-T-D-L', will be represented by the same moiety as desired in the final product except that it will be substituted by a halogen atom or metal such as magnesium, copper, or a boronate ester, at the desired point of attachment to the aryl moiety "A". The coupling reaction of Scheme 1D can be carried out using either the Suzuki-Miyaura strategy or the Ullmann coupling strategy described above in Scheme 1A.

As noted in Reaction Scheme A, the second step in the reaction is to incorporate the hydroxamic acid moiety into the molecule. This may be accomplished as depicted in Scheme 2 below:

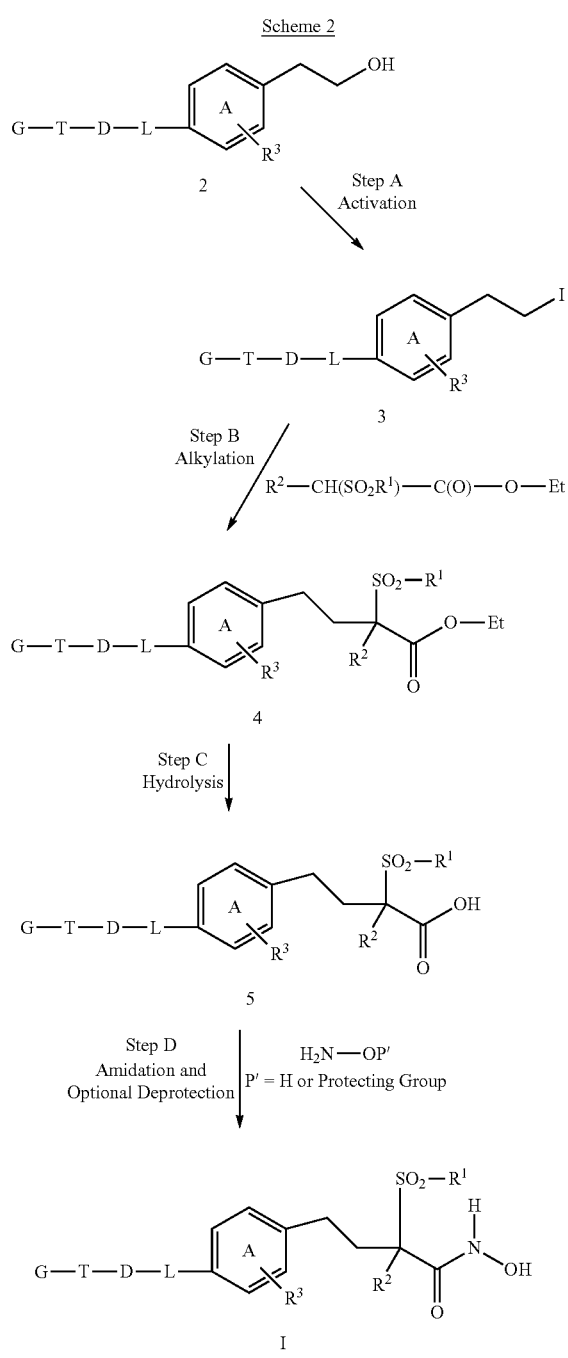

Scheme 2 tion. The desired product of structure 3 may then be isolated and purified as is known in the art, or the crude product may be used in Step B.

In Step B, the leaving group is displaced with the protected alkylsulfonyl acetate or 2-alkylsulfonyl propionic ester as depicted in Scheme 2. $R^1$ and $R^2$ will typically be represented by the same moiety as is desired in the final product. An ethyl ester moiety is depicted, but any standard ester group may be utilized. The alkylation may be carried out as is known in the art. Typically equivalent amounts of the compound of structure 3 and the protected sulfonyl ester are contacted in an aprotic solvent such as dimethylformamide, tetrahydrofuran, etc. An excess of an inorganic base such as cesium carbonate, potassium carbonate or sodium hydride is added to the reaction. The reaction may be run at room temperature or heated to accelerate completion. The desired product of structure 4 may be isolated and purified as is known in the art. Alternatively the crude product may be used in Step C.

In Step C, the protecting group of the carboxylic acid is removed generating the intermediate of structure 5. The manner in which this is accomplished will vary with the identity of the actual protecting group and is well known to those skilled in the art.

In Step D, the hydroxamic acid moiety depicted is incorporated into the molecule. This can also be carried out as is known in the art. If desired, a protected hydroxylamine may be used, followed by a subsequent deprotection reaction. Alternatively hydroxylamine may be directly incorporated. In either case the hydroxamic acid functionality is incorporated into the molecule using standard amidation reactions. For example, the compound of structure 5 may be contacted with an excess of oxalyl chloride in an aprotic solvent such as dichloromethane to allow formation of the corresponding acid chloride, followed by the addition of an excess of either the hydroxylamine or protected hydroxylamine. The reaction is then allowed to proceed to completion and the final product of Formula I or its corresponding protected intermediate is isolated from the reaction medium and purified as is known in the art. As mentioned above, any deprotection, if required, may be carried out as is known in the art.

Scheme B depicted below teaches how to prepare the starting material described in Scheme A:

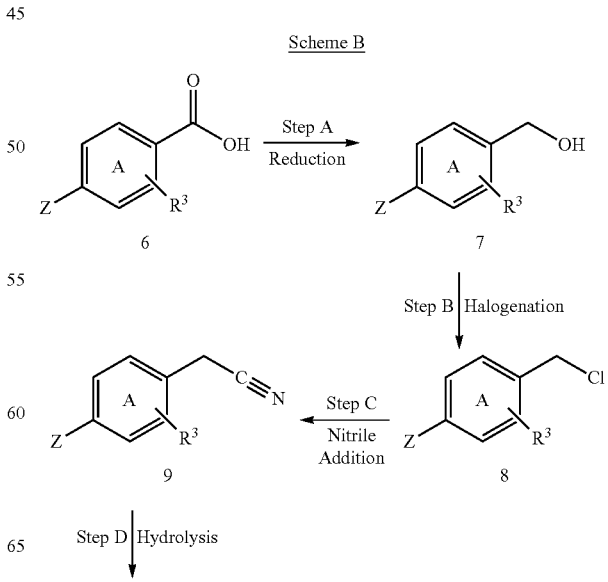

Scheme B

In the initial step, the hydroxyl function depicted in structure 2 is converted into a leaving group. In structure 2, G, T, D, L and $R^3$ will typically be represented by the same moiety as is desired in the final product. Typically, the leaving group will be a halogen atom, such as iodine, but it may also be a tosylate or mesylate functional group. Methods of incorporating such leaving groups are well known to those skilled in the art.

For example, if the desired leaving group is iodine, then the compound of structure 2 is placed in a solution of imidazole and contacted with a molar excess of both triphenylphosphine and iodine. The reaction is typically carried out at reduced temperatures (i.e. 0° C.) and allowed to proceed to comple-

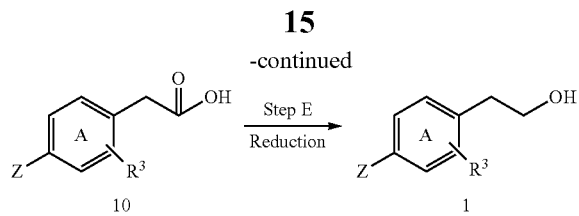

The penultimate starting material, structure 1, can be produced using techniques well known in the art. This material is produced from the carboxylic acid depicted as structure 6. The ring will either be phenyl or heteroaryl depending upon the desired final product. R³ will also typically be represented by the same substituent as is desired in the final product. Z will be a halogen or other appropriately reactive group. Such carboxylic acids may be purchased or produced as described in Comprehensive Organic Transformations: A Guide to Functional Group Preparations by Richard C. Larock, 2nd Edition, 2000, published by Wiley, John & Sons, Inc.

The reduction is typically carried out in an aprotic solvent such as tetrahydrofuran, etc. The carboxylic acid is contacted with an excess of a reducing agent such as borane, etc. at room temperature. The reaction is quenched with a weak base such as potassium carbonate, sodium carbonate, etc. The resulting alcohol, structure 7, may be isolated and purified as known in the art or used as crude in the next step.

In Step B, a halogenation reaction is carried out in which the hydroxyl function is converted to a chlorine atom. This may be accomplished by contacting the alcohol of structure 7 with a chlorinating agent such as thionyl chloride or oxalyl chloride and with a catalytic amount of dimethylformamide (DMF). The reaction will typically be carried out at ambient to reflux temperature and the resulting product, structure 8, may be recovered and isolated as is known or used as crude in Step C.

In Step C, a nitrile addition is carried out as depicted. The product from Step B is contacted with an aprotic solvent such as dimethylformamide, etc. An excess of sodium cyanide, or other cyanide source, is typically added to the reaction mixture and the reaction is allowed to proceed to completion at room temperature. The product, structure, 9, may be isolated and purified or used as crude product in the next step.

The hydrolysis of Step D may be conducted by contacting structure 9 with an aqueous solution of a strong acid such as HCl, etc. The resulting carboxylic acid may be isolated and purified or used as crude product in Step E.

In Step E, the carbonyl is reduced generating the alcohol depicted as structure 1. This reduction may be carried out in the same manner as Step A immediately above. The desired product may be isolated and purified as is known in the art.

The reaction schemes depicted above for producing the compound of Formula I, are merely illustrative. As is readily apparent to one skilled in the art, they may be modified depending upon the specific compound, availability of reagents, etc.

Medical and Veterinary Uses

The compounds may be used for the treatment or prevention of infectious disorders, especially those caused by susceptible and multi-drug resistant (MDR) Gram-negative bacteria. Examples of such Gram-negative bacteria include *Acinetobacter baumannii*, *Acinetobacter* spp., *Achromobacter* spp., *Aeromonas* spp., *Bacteroides fragilis*, *Bordetella* spp., *Borrelia* spp., *Brucella* spp., *Campylobacter* spp., *Citrobacter diversus* (koseri), *Citrobacter freundii*, *Enterobacter aerogenes*, *Enterobacter cloacae*, *Escherichia coli*, *Francisella tularensis*, *Fusobacterium* spp., *Haemophilus influenzae* (β-lactamase positive and negative), *Helicobacter pylori*, *Klebsiella oxytoca*, *Klebsiella pneumoniae* (including those encoding extended-spectrum β-lactamases (hereinafter "ESBLs"), *Legionella pneumophila*, *Moraxella catarrhalis* (β-lactamase positive and negative), *Morganella morganii*, *Neisseria gonorrhoeae*, *Neisseria meningitidis*, *Proteus vulgaris*, *Porphyromonas* spp., *Prevotella* spp., members of the Enterobacteriaceae that express ESBLs KPCs, CTX-M, metallo-β-lactamases, and AmpC-type beta-lactamases that confer resistance to currently available cephalosporins, cephamycins, carbapenems, and beta-lactam/beta-lactamase inhibitor combinations, *Mannheimia haemolyticus*, *Pasteurella* spp., *Proteus mirabilis*, *Providencia* spp., *Pseudomonas aeruginosa*, *Pseudomonas* spp., *Salmonella* spp., *Shigella* spp., *Serratia marcescens*, *Treponema* spp., *Burkholderia cepacia*, *Vibrio* spp., *Yersinia* spp., and *Stenotrophomonas malophilia*.

In a more specific embodiment, the Gram-negative bacteria are selected from the group consisting of *Acinetobacter baumannii*, *Acinetobacter* spp., *Enterobacter aerogenes*, *Enterobacter cloacae*, *Escherichia coli*, *Klebsiella oxytoca*, *Klebsiella pneumoniae*, *Serratia marcescens*, *Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, and beta-lactam/beta-lactamase inhibitor combinations.

Examples of infections that may be treated with the compounds of Formula I include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: www.informahealthcare.com, Expert Opin. Drug Saf. (2008) 7(3).

In order to exhibit this anti-infective activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessibly by local application, such as, for example, eyes, ears including external and middle ear infections, vaginal, open wound, skin including the surface skin and the underneath dermal structures, or other lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 60% by weight, of the active material, depending on the method of administration. Where the compositions comprise dosage units, each unit will contain, for example, from about 5-500 mg of the active ingredient. The dosage as employed for adult human treatment will range, for example, from about 10 to 3000 mg per day, depending on the route and frequency of administration.

If desired, the compounds of the invention may be administered in combination with one or more additional anti-bacterial agents ("the additional active agent"). Such use of compounds of the invention in combination with an additional active agent may be for simultaneous, separate or sequential use.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Experimental Procedures

Experiments were generally carried out under an inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed. Melting points are uncorrected. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20-25° C.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

In the discussion above and in the examples below, the following abbreviations have the following meanings. If an abbreviation is not defined, it has its generally accepted meaning.

Aq.=aqueous
bm=broad multiplet
BOC=tert-butoxycarbonyl
bd=broad doublet
bs=broad singlet
CDI=1,1'-carbonyldiimidazole
d=doublet
dd=doublet of doublets
dq=doublet of quartets
dt=doublet of triplets
DMF=dimethylformamide
DMA=dimethylacetamide
DMAP=dimethylaminopyridine
DMSO=dimethyl sulfoxide
eq.=equivalents
g=grams
h=hours
HPLC=high pressure liquid chromatography
LG=leaving group
m=multiplet
M=molar
M %=mole percent
max=maximum
meq=milliequivalent
mg=milligram
mL=milliliter
mm=millimeter
mmol=millimol
q=quartet
s=singlet
t or tr=triplet
TBS=tert-butyldimethylsilyl
TFA=trifluoroacetic acid
THF=tetrahydrofuran
TLC=thin layer chromatography
p-TLC=preparative thin layer chromatography
pL=microliter
N=normality
MeOH=methanol
DCM=dichloromethane
HCl=hydrochloric acid
ACN=acetonitrile
MS=mass spectrometry
rt=room temperature
EtOAc=ethyl acetate
EtO=ethoxy
Ac=acetate
NMP=1-methyl-2-pyrrolidinone
μL=microliter
J=coupling constant
NMR=nuclear magnetic resonance
MHz=megahertz
Hz=hertz
m/z=mass to charge ratio
min=minutes
ppt=precipitate
CBZ=benzyloxycarbonyl
DCC=1,3-dicyclohexylcarbodiimide
PyBop=benzotriazole-1-yl-oxy-trispyrrolidinophosphonium hexafluorophosphate
Pd(dppf)Cl$_2$=bis(diphenylphosphino)ferrocenepalladium (II) chloride Pd(dppf)Cl$_2$ DCM complex
Pd tetrakis=Tetrakis(triphenylphosphine)palladium(0)
Pd (II) EnCat=Pd (II) EnCat™ BINAP 30
LDA=lithium diisopropylamide
mCPBA=meta-chloroperbenzoic acid
TMS=trimethyl silyl
TPP=triphenyl phosphine
TPPO=triphenyl phosphine oxide
DME=dimethyl ether
IPA=isopropanol
Et$_2$O=diethyl ether
LiHMDS=lithium hexamethyldisilazide/lithium bis(trimethylsilyl)amide
9-BBN=9-Borabicyclo[3.3.1]nonane
sat.=saturated Preparation of Starting Materials Preparation 1

Ethyl 2-(methylsulfonyl)propanoate

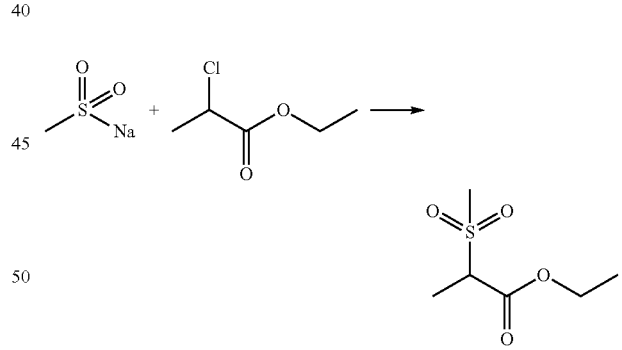

Sodium methyl sulfinate (103 g, 937 mmol) was combined with the ethyl 2-chloropropionate (109 g, 892 mmol) in ethanol (350 mL) in a 500 mL one neck round bottom flask. The reaction was warmed to 77° C. for 20 hours and then allowed to cool to room temperature. Solids were removed by filtration through celite, and the filter pad was washed with ethanol and the combined filtrates were concentrated. The crude product was suspended in diethyl ether (250 mL), and solids were removed by filtration. The filtrate was concentrated in vacuo to afford the title compound as a pale yellow oil (51 g, 73%). $^1$H NMR (400 MHz, CHLOROFORM-d) δ ppm 1.32 (t, J=7.05 Hz, 3H) 1.67 (d, J=7.47 Hz, 3H) 3.05 (s, 3H) 3.83-3.92 (m, 1H) 4.18-4.37 (m, 2H).

Preparation 2

(+/−)-4-(4-Bromophenyl)-N-hydroxy-2-methyl-2-(methylsulfonyl)butanamide

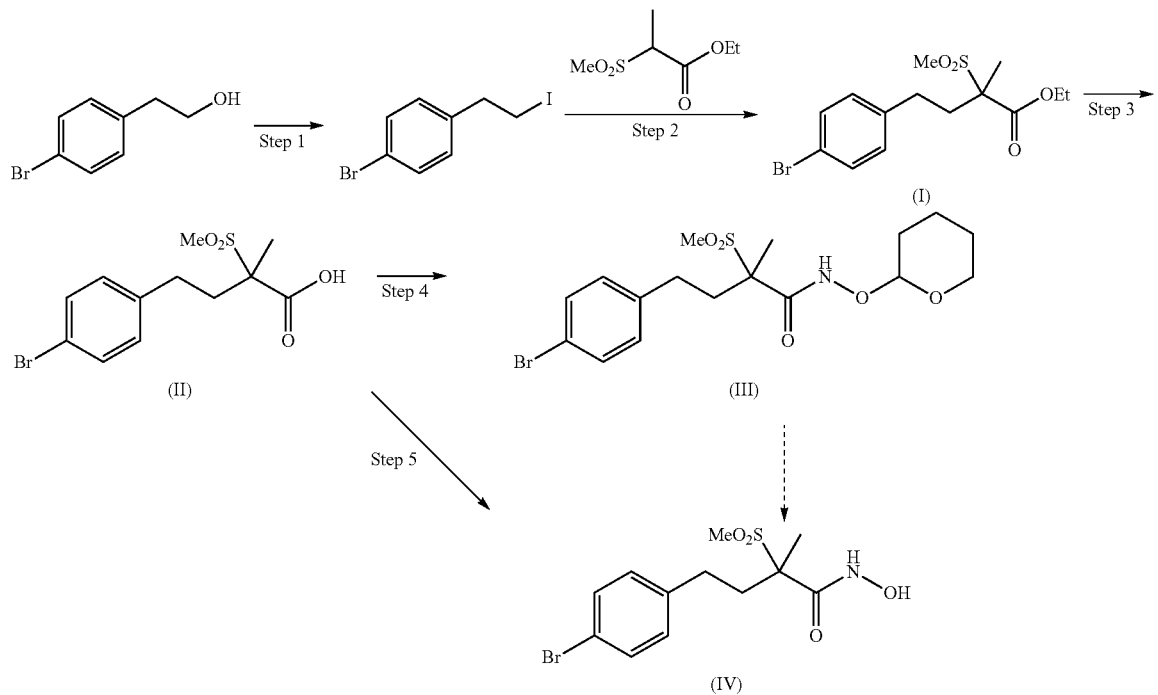

Scheme 1

Step 1

1-Bromo-4-(2-iodoethyl)benzene

A solution of 2-(4-bromophenyl)ethanol (40.0 g, 0.199 mol) in dichloromethane (10 mL) was added dropwise to a solution of imidazole (22.4 mg, 0.329 mmol), triphenylphosphine (66.5 g, 0.254 mol), and iodine (65.0 g, 0.26 mol) in dichloromethane (50 mL) at 0° C. When the addition was complete it was warmed to rt. After 1 hour the reaction was filtered through celite, the filtrate was washed with saturated aqueous sodium thiosufate (2×100 mL), brine (100 mL), dried over $MgSO_4$, filtered and concentrated in vacuo. Purification by flash column chromatography on silica gel (heptane/ethyl acetate 4:1) afforded the title compound as a yellow-white solid (59.09 g, 60%). $^1$HNMR (400 MHz, CHLOROFORM-d) δ ppm 3.14 (t, J=7.69 Hz, 2H) 3.33 (t, J=7.69 Hz, 2H) 7.08 (d, J=7.89 Hz, 2H) 7.45 (d, J=8.31 Hz, 2H)

Step 2

(+/−)-Ethyl 4-(4-bromophenyl)-2-methyl-2-(methylsulfonyl)butanoate (I)

A suspension of 1-bromo-4-(2-iodo-ethyl)-benzene (25.0 g, 80 mmol) and (+/−)-2-methanesulfonyl-propionic acid ethyl ester (15.9 g, 88.4 mmol) in DMF (100 mL) with solid $Cs_2CO_3$ (52.4 g, 161 mmol) was stirred overnight at room temperature. After 16 hours the reaction was poured into water (500 mL). The resulting suspension was stirred for 2 h. The mixture was extracted with diethylether (2×). The organic layers were combined and washed with water then brine, dried ($Na_2SO_4$) and concentrated in vacuo. Purification by flash column chromatography on silica gel (hexanes/ethyl acetate 9:1-8:2) afforded the title compound as a white solid (21.0 g, 72%). $^1$HNMR (400 MHz, CHLOROFORM-d) δ ppm 1.35 (t, J=7.22 Hz, 3H) 1.70 (s, 3H) 2.14-2.24 (m, 1H) 2.42-2.55 (m, 2H) 2.68-2.78 (m, 1H) 3.04 (s, 3H) 4.25-4.31 (m, 2H) 7.07 (d, J=8.20 Hz, 2H) 7.43 (d, J=8.20 Hz, 2H)

Step 3

(+/−)-4-(4-Bromophenyl)-2-methyl-2-(methylsulfonyl)butanoic acid (II)

Lithium hydroxide (3.29 g, 78.5 mmol) was added to a stirred solution of (+/−)-ethyl 4-(4-bromophenyl)-2-methyl-2-(methylsulfonyl)butanoate (9.50 g, 78.5 mmol) in THF:MeOH:water (2:2:1, 225 mL) at 0° C. The reaction was warmed to room temperature as the ice bath expired. After 18 hours the reaction was acidified to pH 4 with 1N HCl (aq) and extracted with ethyl acetate (2×). The organic layers were combined, dried ($Na_2SO_4$) and concentrated in vacuo to give a white solid (8.5 g, 97%). LCMS m/z 333.1 (M−1). $^1$H NMR (400 MHz, DMSO-$d_6$) δ ppm 1.53 (s, 3H) 1.95-2.05 (m, 1H) 2.30-2.48 (m, 2H) 2.67-2.79 (m, 1H) 3.10 (s, 3H) 3.26 (br. s., 1H) 7.17-7.24 (m, 2H) 7.43-7.52 (m, 2H).

Step 4

(+/−)-4-(4-Bromophenyl)-2-methyl-2-(methylsulfonyl)-N-(tetrahydro-2H-pyran-2-yloxy)butanamide (III) (a mixture of diastereomers)

Triethylamine (5.49 g, 54.3 mmol) and 1H-benzo[d][1,2,3]triazol-1-ol (7.5 g, 49 mmol) were added to a solution of the (+/−)-4-(4-bromophenyl)-2-methyl-2-(methylsulfonyl)butanoic acid (9.1 g, 27.1 mmol) in dichloromethane (100 mL). After 10 minutes O-tetrahydro-2H-pyran-2yl-hydroxylamine (4.6 g, 39 mmol) was added followed by N1-((ethylimino)methylene)-N3,N3-dimethylpropane-1,3-diamine hydrochloride (EDCI) (7.2 g, 38 mmol). After 12 h the reaction was quenched by the addition of saturated aqueous $NaHCO_3$. The layers were separated and the organic layer was dried ($Na_2SO_4$), filtered and concentrated in vacuo. Purification by flash column chromatography on silica gel (hexanes/ethyl acetate 7:3-6:4) afforded the title compound as a white solid (9.0 g, 76%). LCMS m/z 434.1 (M+1) $^1$H NMR (400 MHz, DMSO-$d_6$) δ ppm 1.54 (d, J=3.90 Hz, 6H) 1.69 (br. s., 3H) 1.78-2.06 (m, 1H) 2.27-2.55 (m, 2H) 2.59-2.72 (m, 1H) 3.03 (d, J=6.64 Hz, 3H) 3.50 (d, J=11.32 Hz, 1H) 3.95-4.22 (m, 1H) 4.97 (d, J=9.37 Hz, 1H) 7.22 (dd, J=8.39, 4.49 Hz, 2H) 7.49 (d, J=8.20 Hz, 2H) 11.36 (br. s., 1H)

Step 5

(+/−)-4-(4-Bromophenyl)-N-hydroxy-2-methyl-2-(methylsulfonyl)butanamide (IV)

Oxalyl chloride (4.50 mL, 50 mmol) was added to a solution of 4-(4-bromophenyl)-2-methyl-2-(methylsulfonyl)butanoic acid (II) (14.69 g, 43.82 mmol) in DCM (300 mL) under nitrogen at ambient temperature, followed by DMF (340 ul). The reaction was stirred until effervescence ceased and then was allowed to stir for 1 hour. O-TMS-hydroxylamine (16.0 mL, 130 mmol) was added via syringe and the suspension was stirred for 1 hour. The reaction was quenched with methanol (60 mL), stirred for 1 hour and concentrated in vacuo to afford a yellow-white solid. The solid was triturated in DCM (200 mL) overnight. The solid was collected by filtration, washed with 1:1 DCM:heptane (2×100 mL), and dried under vacuum to afford the title compound as a white solid (14.85 g, 96.76%). LC-MS m/z 350.0 (M+1). $^1$H NMR (500 MHz, METHANOL-$d_4$) δ ppm 1.64 (s, 3H) 2.00-2.10 (m, 1H) 2.44-2.58 (m, 2H) 2.61-2.77 (m, 1H) 3.04 (s, 3H) 7.18 (d, J=8.29 Hz, 2H) 7.44 (d, J=8.29 Hz, 2H).

Preparation 3

(+/−)-2-Methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide (VII)

Scheme 2

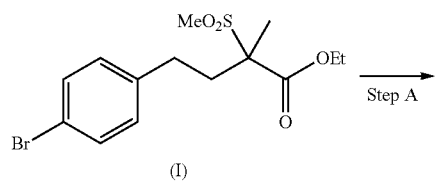

(I)

Step A (+/−)-Ethyl 2-methyl-2-(methylsulfonyl)-4-[4-(4,4,5,5-tetramethyl-1,3,2-dioxaborolan-2-yl)phenyl]butanoate (V)

General Procedure for Pinacol Boronate Ester Formation

A solution of (+/−)-ethyl 4-(4-bromophenyl)-2-methyl-2-(methylsulfonyl)butanoate (12.50 g, 34.41 mmol), bis(pinacolato)diborane (10.5 g, 41.3 mmol), potassium acetate (16.9 g, 172 mmol) and Pd(dppf)$Cl_2$ (2.81 g, 3.44 mmol) in 1,4-dioxane (150 mL) was heated to reflux. After 12 hours the reaction was diluted with dichloromethane and filtered through celite. The filtrate was concentrated in vacuo and subjected to purification by flash column chromatography on silica gel (hexanes/ethyl acetate 8:2-1:1) to give the title compound as a tan solid (10.0 g, 71%). APCI m/z 411.3 (M+1). $^1$H NMR (400 MHz, DMSO-$d_6$) δ ppm 1.23 (t, J=7.03 Hz, 3H) 1.28 (s, 12H) 1.57 (s, 3H) 1.97-2.11 (m, 1H) 2.35-2.48 (m, 2H) 2.69-2.84 (m, 1H) 3.11 (s, 3H) 4.12-4.27 (m, 2H) 7.25 (d, J=8.01 Hz, 2H) 7.61 (d, J=8.20 Hz, 2H).

Step B (+/−)-2-Methyl-2-(methylsulfonyl)-4-[4-(4,4,5,5-tetramethyl-1,3,2-dioxaborolan-2-yl)phenyl]butanoic acid (VI)

The title compound (5.47 g, 100%) was prepared from (+/−)-ethyl 2-methyl-2-(methylsulfonyl)-4-[4-(4,4,5,5-tetramethyl-1,3,2-dioxaborolan-2-yl)phenyl]butanoate (5.2 g, 12.7 mmol) and lithium hydroxide (2.13 g, 50.8 mmol) by a procedure analogous to that described for (+/−)-4-(4-bromophenyl)-2-methyl-2-(methylsulfonyl)butanoic acid (II/Step 3-Preparation Number 2). LCMS m/z 381.6 (M−1). $^1$H NMR (400 MHz, CHLOROFORM-d) δ ppm 1.36 (s, 12H) 1.75 (s, 3H) 2.19-2.30 (m, 1H) 2.44-2.55 (m, 1H) 2.56-2.67 (m, 1H) 2.76-2.87 (m, 1H) 3.09 (s, 3H) 7.23 (d, J=8.01 Hz, 2H) 7.76 (d, J=8.20 Hz, 2H).

Step C (+/−)-2-Methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide (VII) (mixture of diastereomers)

The title compound (3.69 g, 60.4%) was prepared from (+/−)-2-methyl-2-(methylsulfonyl)-4-[4-(4,4,5,5-tetramethyl-1,3,2-dioxaborolan-2-yl)phenyl]butanoic acid (4.86 g, 12.7 mmol) and O-tetrahydro-2H-pyran-2-yl-hydroxylamine (2.1 g, 18.0 mmol) by a procedure analogous to that described for (+/−)-4-(4-bromophenyl)-2-methyl-2-(methylsulfonyl)-N-(tetrahydro-2H-pyran-2-yloxy)butanamide (III/Step 4—Preparation Number 2). LCMS m/z 480.3 (M−1).

Preparation 4

2-(5-Bromopyridin-2-yl)ethanol pended in H$_2$O (1000 mL) and stirred for 30 min. The solids were filtered and the aqueous phase re-extracted with CHCl$_3$ (3×500 mL). The combined organic layers were dried over Na$_2$SO$_4$, filtered and concentrated in vacuo which gave a further 46.2 g. Combined yield of desired 96.2 g of compound 2 (0.55 mol, 35%). $^1$H-NMR (CDCl$_3$, 300 MHz): δ ppm 7.17 (t, 1H, ArH), 7.42 (d, 1H, ArH), 8.16 (d, 1H, ArH), 8.38 (s, 1H, ArH).

Preparation of 3: 5-(5-Bromopyridin-2(1H)-ylidene)-2,2-dimethyl-1,3-dioxane-4,6-dione (Two Identical Batches were Performed)

Two solutions of Meldrum's acid (30.32 g, 210.3 mmol) in Ac$_2$O (210 mL) were cooled to 0° C. 3-Bromopyridine-N-oxide (36.6 g, 210.3 mmol) was added drop-wise to each, keeping the reaction temperatures below 5° C. The two reaction mixtures were allowed to warm up to room temperature and stirred overnight. The batches were combined and filtered. The remaining solid (4) was washed with hot chloroform (50-55° C.). The filtrate was concentrated in vacuo. The residue was crystallized from methanol to give the desired product (3) (29.63 g, 23%). $^1$H-NMR (CDCl$_3$, 300 MHz): δ 1.61 (s, 6H, 2×CH$_3$), 8.23 (d, 1H, ArH), 8.54 (d, ArH), 8.65 (d, 1H, ArH).

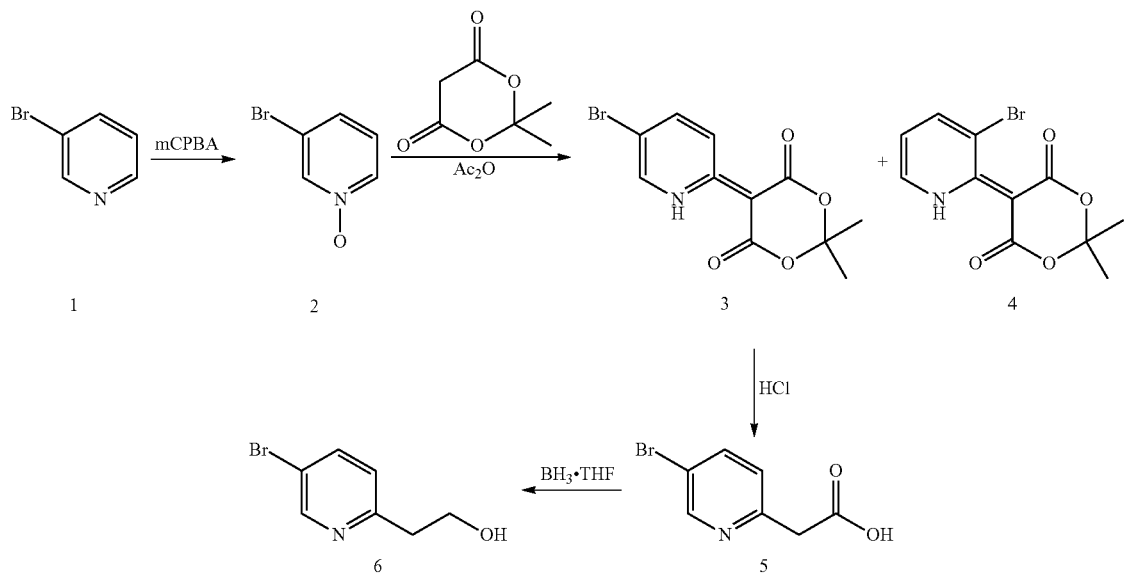

Preparation of 2

3-Bromopyridine-N-oxide

To a solution of 3-bromopyridine (1, 250.0 g, 1.58 mol) in DCM (3500 mL) was added a solution of NaHCO$_3$ (358.9 g, 4.27 mol) in H$_2$O (4270 mL). The biphasic system was cooled to 0° C. and mCPBA (70-75% with H$_2$O, 780.0 g, 3.16 mol) was added in portions. The mixture was allowed to warm up to room temperature and was stirred overnight. The layers were separated and the aqueous phase was extracted with DCM (2×2000 mL). The combined organic layers were dried over Na$_2$SO$_4$, filtered and concentrated in vacuo, but this led to an insignificant isolation of desired material. The aqueous phase was re-extracted with CHCl$_3$ (2×1000 mL), yielding 50 g of the desired product. The remaining material was sus- Preparation of 5

2-(5-Bromopyridin-2-yl)acetic acid

A solution of 5-(5-bromopyridin-2(1H)-ylidene)-2,2-dimethyl-1,3-dioxane-4,6-dione (3) (40.0 g, 133.3 mmol) in HCl (30%, 400 mL) was heated gently to reflux, and was refluxed for 2 h. The solvent was removed in vacuo and the residue (29.75 g) was used in the next step without further purification. $^1$H-NMR (CDCl$_3$, 300 MHz): δ 3.79 (s, 2H, CH$_2$), 7.41 (d, 1H, ArH), 8.08 (dd, 1H, ArH), 8.66 (d, 1H, ArH).

Preparation of 6

2-(5-Bromopyridin-2-yl)ethanol

Under N$_2$, a solution of 2-(5-bromopyridin-2-yl)acetic acid (5, 29.75 g) in THF (450 mL) was cooled to 0° C. Borane THF complex (1 M in THF, 413.2 mL, 413.2 mmol) was added dropwise, keeping the reaction temperature below 5° C. The mixture was allowed to warm to room temperature and stir for 4 h. The mixture was cooled to 0° C. and saturated aqueous $K_2CO_3$ solution (500 mL) and $H_2O$ (500 mL) were added slowly. The mixture was extracted with EtOAc (3×500 mL). The combined organic layers were washed with brine (500 mL), dried over $Na_2SO_4$ and filtered. The solvent was removed in vacuo and the residue was purified by column chromatography (silica, Heptane/EtOAc 3:7) yielding compound 6 (10.9 g, 53.9 mmol, 40% over 2 steps). $^1$H-NMR (CDCl$_3$, 300 MHz): δ 3.00 (t, 2H, CH$_2$), 3.64 (bs, 1H, OH), 4.03 (t, 2H, CH$_2$), 7.10 (d, 1H, ArH), 7.76 (dd, 1H, ArH), 8.59 (d, 1H, ArH).

Preparation 5

2-(4'-Fluoro-3-methoxy-biphenyl-4-yl)-ethanol

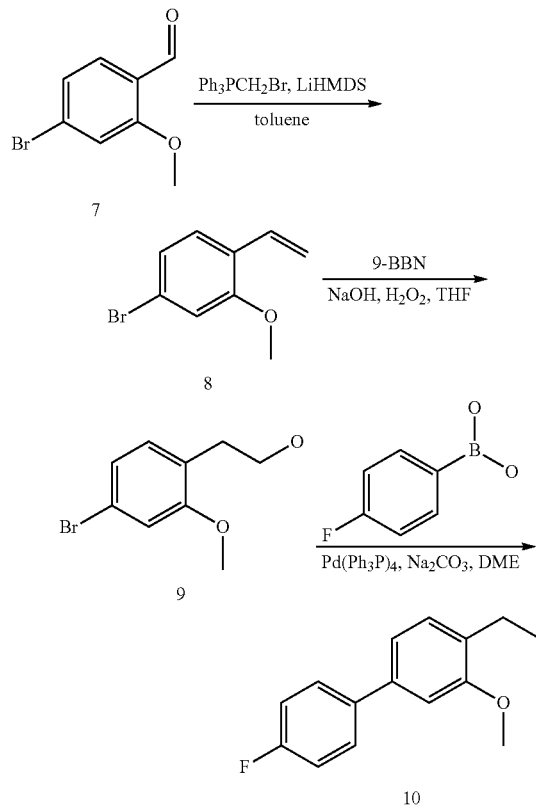

Preparation of 8

4-Bromo-2-methoxy-1-vinyl-benzene

To a suspension of Ph$_3$PCH$_2$Br (140 g, 0.384 mol) in anhydrous toluene (1l) was added LiHMDS (350 mL, 0.35 mol) at 0° C. After the addition, the mixture was stirred at room temperature for 1 hr, then cooled to 0° C., and a solution of compound 7 (62 g, 0.288 mol) in anhydrous toluene (800 mL) was added dropwise. The mixture was stirred at room temperature overnight. TLC (petroleum ether/ethyl acetate 10/1) showed the reaction was complete. The mixture was cooled to 0° C. and NH$_4$Cl (500 mL) was added. The mixture was extracted with ethyl acetate (2×300 mL), and the combined organic layers were washed with brine (3×100 mLI), dried over sodium sulfate and filtered. The filtrate was concentrated in vacuo to give crude product (96 g), which was purified via column chromatography on silica gel (petroleum ether) to give compound 8 (42 g, 68.3%) as an oil.

Preparation of 9

2-(4-Bromo-2-methoxy-phenyl)-ethanol

To a solution of compound 8 (37 g, 0.174 mol) in anhydrous THF (400 mL) was added dropwise 9-BBN (418 mL, 0.209 mol) at 0° C. under N$_2$. After the addition, the reaction mixture was stirred at room temperature overnight. TLC (petroleum ether/ethyl acetate 5/1) indicated the reaction was complete. The mixture was cooled to 0° C. and methanol (300 mL) was added, followed by the addition of 2 M NaOH solution (35 g, in 440 mL of H$_2$O) and H$_2$O$_2$ (185 mL, 30% in water). The reaction mixture was then stirred at room temperature for 2 h. The mixture was concentrated in vacuo and the residue was suspended in water (200 mL) and extracted with diethyl ether (300 mLx3). The combined organic layers were washed with brine (200 mL), filtered and the filtrate was concentrated in vacuo to give crude product (32 g), which was purified via column chromatography on silica gel (petroleum ether/ethyl acetate from 20/1 to 4/1) to give compound 9 (26.5 g, 66.1%) as a white solid.

Preparation of 10

2-(4'-Fluoro-3-methoxy-biphenyl-4-yl)-ethanol

A mixture of compound 9 (15 g, 64.9 mmol), 4-fluorophenyl boronic acid (10.9 g, 77.9 mmol), Pd(Ph$_3$P)$_4$ (2 g) and Na$_2$CO$_3$ (27.5 g, in 130 mL water) in DME (150 mL) was heated to reflux and stirred overnight. TLC (petroleum ether/ethyl acetate 3/1) indicated the reaction was complete. The mixture was cooled to room temperature and extracted with ethyl acetate (100 mL×3). The combined organic layers were washed with brine (50 mL), dried over Na$_2$SO$_4$, filtered and the filtrate was concentrated in vacuo to give crude product (26 g), which was purified via column chromatography on silica gel (petroleum ether/ethyl acetate from 10/1 to 4/1) to give compound 10 (12.5 g, 78.1%) as a white solid.

Preparation 6

Resolution of I: (+/−)-ethyl 4-(4-bromophenyl)-2-methyl-2-(methylsulfonyl)butanoate to generate individual enantiomers Ia and Ib

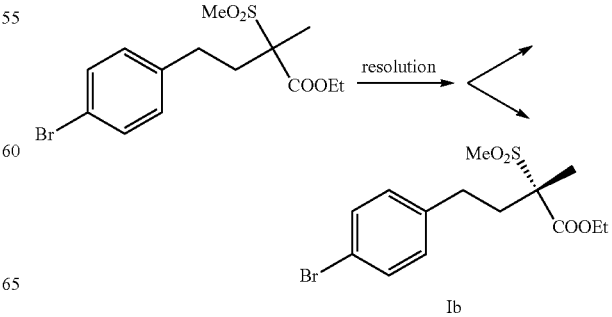

-continued

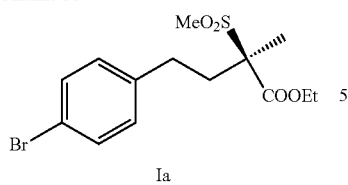

Ia

The title compounds were isolated via chiral chromatography with a packing material of Chiralcel OJ and a mobile phase of 68/32/0.1 heptane/ethanol/phosphoric acid. Both isomers were isolated separately. They were evaporated to low volume, water was added, and the solids that crashed out were filtered and dried. The desired (2R) enantiomer 1a was determined to have an optical rotation in DMSO $[\alpha]_{589}^{25.3}=+19.18°$.

Preparation 7

A) Resolution of II: 2-methyl-2-methylsulfonyl-4-(4-bromophenyl)butanoic acid

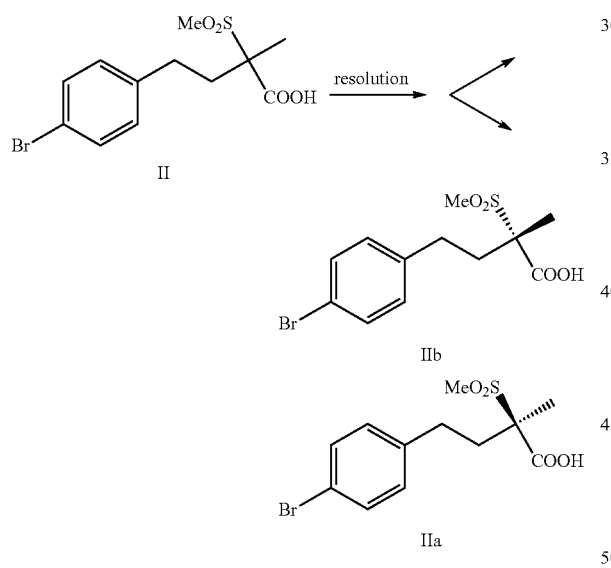

A mixture of (+/−)-4-(4-bromophenyl)-2-methyl-2-(methylsulfonyl)butanoic acid (17.3 g, 51.6 mmol) and (−) ephedrine (8.5 g 51.6 mmol) was dissolved in a mixture of IPA (175 mL) and water (2.5 mL) by the application of some heat. The clear solution was diluted with the same amount of solvents and seeded. Crystallization started rapidly and more IPA (50 mL) and water (1 mL) were added. Crystallization was allowed to proceed over 2 days and the solid was isolated. This afforded 12.45 g of the ephedrine salt of IIa (48%) with an ee of 74%. Recrystallization of this material from IPA-water (200 mL+3 mL) afforded 10 g of the salt with an ee of 97.4%. This was triturated with IPA (200 mL) to afford 9.5 g (36%) of the salt with an ee of 99+%. Liberation of the salt with 1N HCl follows by EtOAc extraction afforded 5.7 g of acid IIa.

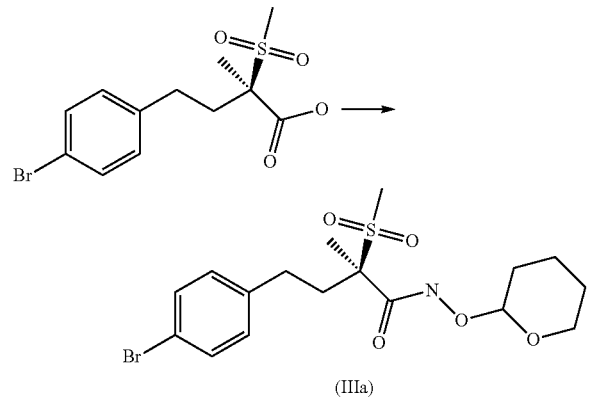

B) Preparation of IIIa: 2R)-4-(4-bromophenyl)-2-methyl-2-(methylsulfonyl)-N-(tetrahydro-2H-pyran-2-yloxy)butanamide (mixture of diastereomers)

The title compound (10.0 g, 77%) was prepared from (2R)-4-(4-bromophenyl)-2-methyl-2-(methylsulfonyl)butanoic acid (IIa)(10.0 g, 29.8 mmol) and O-tetrahydro-2H-pyran-2-yl-hydroxylamine (5.0 g, 43 mmol) by a procedure analogous to that described for (+/−)-4-(4-bromophenyl)-2-methyl-2-(methylsulfonyl)-N-(tetrahydro-2H-pyran-2-yloxy)butanamide as in Preparation 2 Step 4. LCMS m/z 434.1 (M−1).

Preparation 8

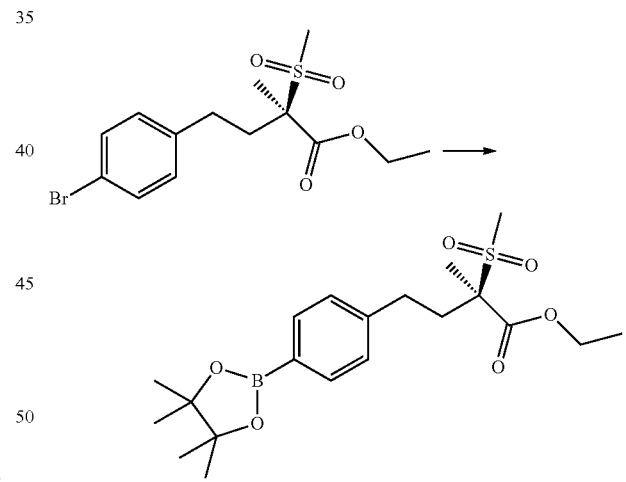

A) Preparation of Va: ethyl (2R)-2-methyl-2-(methylsulfonyl)-4-[4-(4,4,5,5-tetramethyl-1,3,2-dioxaborolan-2-yl)phenyl]butanoate The title compound (10.5 g, 93%) was prepared from ethyl (2R)-4-(4-bromophenyl)-2-methyl-2-(methylsulfonyl)butanoate, (10.0 g, 27.5 mmol) and bis(pinacolato)diborane (7.69 g, 30.3 mmol) by a procedure analogous to that described for (+/−)-ethyl 2-methyl-2-(methylsulfonyl)-4-[4-(4,4,5,5-tetramethyl-1,3,2-dioxaborolan-2-yl)phenyl]butanoate as described in Preparation 3 step A.

¹H NMR (400 MHz, CHLOROFORM-d) δ ppm 1.32 (t, J=7.32, 3H) 1.32 (s, 12H) 1.69 (s, 3H) 2.14-2.24 (m, 1H) 2.42-2.56 (m, 2H) 2.71-2.81 (m, 1H) 2.99-3.05 (m, 3H) 4.23-4.30 (m, 2H) 7.18 (d, J=8.01 Hz, 2H) 7.73 (d, J=8.01 Hz, 2H)

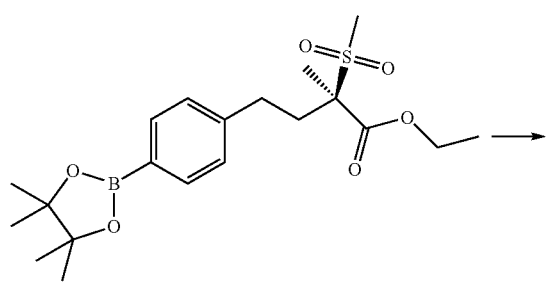

B) Preparation of VIa: (2R)-2-methyl-2-(methylsulfonyl)-4-[4-(4,4,5,5-tetramethyl-1,3,2-dioxaborolan-2-yl)phenyl]butanoic acid The title compound (7.4 g, 76%) was prepared from ethyl (2R)-2-methyl-2-(methylsulfonyl)-4-[4-(4,4,5,5-tetramethyl-1,3,2-dioxaborolan-2-yl)phenyl]butanoate (10.5 g, 25.6 mmol) and lithium hydroxide (4.3 g, 102 mmol) by a procedure analogous to that described for (+/−)-4-(4-bromophenyl)-2-methyl-2-(methylsulfonyl)butanoic acid as in Preparation 3 step B. LCMS m/z 381.6 (M−1).

¹H NMR (400 MHz, CHLOROFORM-d) δ ppm 1.35 (s, 12H) 1.72 (s, 3H) 2.21 (td, J=12.83, 5.17 Hz, 1H) 2.39-2.54 (m, 1H) 2.61 (td, J=12.83, 4.39 Hz, 1H) 2.71-2.90 (m, 1H) 3.08 (s, 3H) 4.36 (br. s., 1H) 7.21 (d, J=7.81 Hz, 2H) 7.75 (d, J=8.00 Hz, 2H)

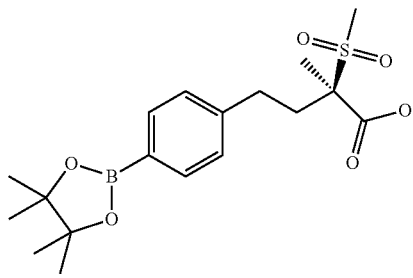

VIa

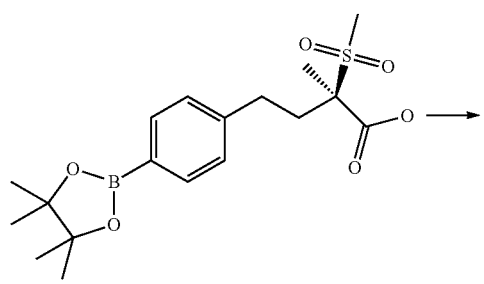

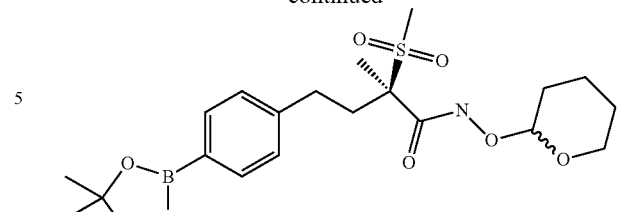

VIIa

C) Preparation of VIIa: (2R)-2-methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide (mixture of diastereomers)

The title compound (7.2 g, 77%) was prepared from (2R)-2-methyl-2-(methylsulfonyl)-4-[4-(4,4,5,5-tetramethyl-1,3,2-dioxaborolan-2-yl)phenyl]butanoic acid (7.4 g, 19.3 mmol) and O-tetrahydro-2H-pyran-2-yl-hydroxylamine (3.3 g, 28 mmol) by a procedure analogous to that described for (+/−)-4-(4-bromophenyl)-2-methyl-2-(methylsulfonyl)-N-(tetrahydro-2H-pyran-2-yloxy)butanamide as in Preparation 3 step C. LCMS m/z 480.8 (M−1).

Example 1

N-Hydroxy-2-methyl-4-(3-methylbiphenyl-4-yl)-2(methylsulfonyl)butanamide

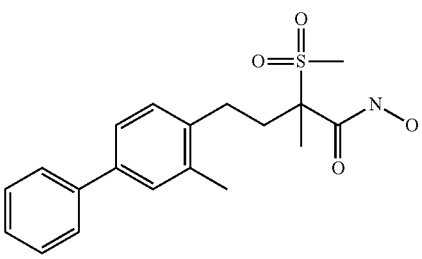 [SMILES: Cc1cc(-c2ccccc2)ccc1CCC(C)(C(=O)NO)S(C)(=O)=O]

Step A: 4-Bromo-2-methyl-phenyl)-methanol

4-Bromo-2-methylbenzoic acid (100 g, 460 mmol) was dissolved in THF (300 mL), and cooled in an ice-bath to 0° C. Borane (1 M in THF, 500 mL, 1.1 eq.) was added dropwise over a period of 30 minutes, while keeping the temperature below 20° C. After complete addition, the reaction mixture was stirred for 1 hour at room temperature, and was then carefully added to saturated aq. K₂CO₃ (250 mL). The obtained suspension was diluted with H₂O (500 mL). The THF layer was separated, and concentrated under reduced pressure. The aqueous layer was extracted with EtOAc (3×300 mL). The residue from the concentrated THF layer was dissolved in the combined organic layer, which was washed with brine. The organic layer was dried (Na₂SO₄), filtered, and concentrated in vacuo yielding the title compound (62 g, 308 mmol, 67%) with acceptable purity according to ¹H NMR as a yellow oil. ¹H NMR (CDCl₃, 300 MHz) δ ppm 2.31 (s, 3H); 4.63 (s, 2H); 7.22 (d, 1H); 7.33 (s, 2H)

Step B: 4-Bromo-1-chloromethyl-2-methyl-benzene (4-Bromo-2-methyl-phenyl)-methanol (40.0 g, 199 mmol) was added to thionyl chloride (106.6 g, 0.896 mole, 65.3 mL). The mixture was heated to reflux, for 1.5 hours. After cooling to room temperature the mixture was concentrated under reduced pressure. The residue was dissolved in EtOAc (300 mL) and added carefully to saturated aqueous NaHCO$_3$ (500 mL). The EtOAc layer was separated, and the aqueous layer was extracted with EtOAc (250 mL). The combined organic layers were dried (Na$_2$SO$_4$), filtered and concentrated in vacuo yielding the title compound (34.19 g, 157 mmol, 79%) as a slightly colored oil that solidified to a white solid upon standing. $^1$H NMR (CDCl$_3$, 300 MHz) δ ppm 2.38 (s, 3H); 4.57 (s, 2H); 7.12 (d, 1H); 7.28 (s, 1H); 7.55 (d, 1H)

Step C: (4-Bromo-2-methylphenyl)acetonitrile

4-Bromo-1-chloromethyl-2-methyl-benzene (63 g, 287 mmol) was dissolved in DMF (180 mL). NaCN (15.5 g, 316 mmol, 1.1 eq.) was added in 1 portion, and the reaction was stirred at room temperature overnight under a N$_2$ atmosphere. The mixture was concentrated under reduced pressure, and the residue was taken into a mixture of sat. aq. NH$_4$Cl (300 mL) and EtOAc (300 mL). The bi-phase solution was diluted with H$_2$O (200 mL). The EtOAc layer was separated, and the aqueous layer was re-extracted with EtOAc (2×200 mL). The combined organic layers were washed with brine (3×300 mL), dried (Na$_2$SO$_4$), filtered, and concentrated under reduced pressure, yielding the title compound (58.8 g, 280 mmol, 98%) with acceptable purity as a brown oil, which solidified to a brown solid on standing. $^1$H-NMR (CDCl$_3$, 300 MHz) δ ppm 2.34 (s, 3H); 3.63 (s, 2H); 7.26 (t, 1H); 7.38 (d, 2H).

Step D: (4-Bromo-2-methylphenyl)acetic acid

To (4-Bromo-2-methylphenyl)acetonitrile (58.8 g, 280 mmol) was added 30% aq. HCl (500 mL). The suspension was refluxed for 18 hours. After cooling to room temperature, the solids were collected by filtration, and the filtrate was extracted with CH$_2$Cl$_2$ (750 mL). The solids were dissolved in the organic layer, which was washed with brine, dried (Na$_2$SO$_4$), filtered and concentrated under reduced pressure, yielding the title acid (59 g, 258 mmol, 92%) as a brownish solid. 1H-NMR (CDCl3, 300 MHz) δ ppm 2.32 (s, 3H); 3.64 (s, 2H); 7.09 (d, 1H); 7.31 (d, 1H); 7.36 (s, 1H)

Step E: 2-(4-Bromo-2-methylphenyl)ethanol (4-Bromo-2-methylphenyl)acetic acid (59 g, 258 mmol) was dissolved in THF (100 mL), and cooled in an ice-bath to 0° C. Borane (1 M in THF, 310 mL, 1.2 eq) was added dropwise. During the addition the temperature rose slowly to 20° C. After complete addition, the ice-bath was removed and stirring was continued for 2 hours. The reaction mixture was poured into sat. aq. K$_2$CO$_3$ (300 mL), and the obtained suspension was diluted with H$_2$O (500 mL). The THF layer was separated and concentrated under reduced pressure. The aqueous layer was extracted with EtOAc (2×250 mL, 1×100 mL). The residue from the concentrated THF layer was dissolved in the combined organic layer, which was washed with brine. The organic layer was dried (Na$_2$SO$_4$), filtered, and concentrated under reduced pressure, yielding the crude product (54.6 g) as a brown oil. The crude product was purified by column chromatography (SiO$_2$, 2 L of 30% EtOAc in heptanes, Rf=0.3). Desired fractions were combined and concentrated under reduced pressure, yielding the title compound as a yellow oil (31.6 g, 144 mmol, 56%). 1H-NMR (CDCl3, 300 MHz) δ ppm 2.3 (s, 3H); 2.68 (t, 2H); 2.82 (t, 2H); 7.07 (d, 1H); 7.30 (d, 2H).

Step F: 4-Bromo-1-(2-iodo-ethyl)-2-methyl-benzene

To a 250 mL flask in an ice bath was added triphenyl phosphine (6.17 g, 22.8 mmol), imidazole (1.6 g, 22.8 mmol) and 100 mL of anhydrous dichloromethane. Once dissolved, iodine (5.79 g, 22.8 mmol) was added. The reaction was then stirred for about 30 minutes (ppt formed). The 2-(4-bromo-2-methylphenyl)ethanol (3.93 g, 18.3 mmol) was added in batches and the flask was rinsed with the remaining DCM (22 mL) which was also added to the reaction mixture. The reaction was warmed to room temperature and was stirred overnight. The reaction mixture was filtered through a small pad of celite and washed with DCM (100 mL). The filtrate was washed with saturated aqueous sodium thiosulfate (200 mL) and brine 200 mL. The organics were concentrated in vacuo to furnish a white solid (triphenyphosphine oxide+desired product). The material was triturated with heptanes for 5-10 mins then filtered to remove the majority of the triphenylphosphine oxide The filtrate was concentrated in vacuo to furnish a total of 5.86 g (98.8%) of the title compound as a clear oil that solidified upon standing. $^1$H NMR (400 MHz, CHLOROFORM-d) δ ppm 2.30 (s, 3H) 3.04-3.20 (m, 2H) 3.21-3.39 (m, 2H) 7.02 (d, J=8.20 Hz, 1H) 7.23-7.29 (m, 1H) 7.30-7.38 (m, 1H).

Step G: 4-(4-Bromo-2-methyl-phenyl)-2-methanesulfonyl-2-methyl-butyric acid ethyl ester The title compound was synthesized according to the general procedure Preparation #2, Step 2, except that 4-bromo-1-(2-iodo-ethyl)-2-methyl-benzene was used instead of 1-bromo-4-(2-iodoethyl)benzene and the reaction was conducted at 40° C. to yield: 2.2 g (33%). $^1$H NMR (400 MHz, CHLOROFORM-d) δ ppm 1.37 (t, J=7.22 Hz, 3H) 1.73 (s, 3H) 2.09 (td, 1H) 2.30 (s, 3H) 2.33-2.43 (m, 1H) 2.49 (td, J=12.88, 4.29 Hz, 1H) 2.70 (td, J=12.59, 4.88 Hz, 1H) 3.01-3.07 (m, 3H) 4.32 (q, J=7.03 Hz, 2H) 7.00 (d, J=8.20 Hz, 1H) 7.27 (s, 1H) 7.31 (s, 1H).

Step H: 4-(4-Bromo-2-methylphenyl)-2-methyl-2-(methylsulfonyl)butanoic acid

The title compound was synthesized according to the general procedure of Preparation Number 2, Step 3, for the preparation of (II) except that 4-(4-bromo-2-methyl-phenyl)-2-methanesulfonyl-2-methyl-butyric acid ethyl ester was used instead of (+/−)-ethyl 4-(4-bromophenyl)-2-methyl-2-(methylsulfonyl)butanoate and that the lithium hydroxide was dissolve in water prior to addition. Yield: 3.259 (81.2%).

LC-MS m/z 349.0 (M−1) $^1$H NMR (400 MHz, CHLOROFORM-d) δ ppm 1.77 (s, 3H) 2.09-2.20 (m, 1H) 2.30 (s, 3H) 2.39 (td, J=12.88, 4.29 Hz, 1H) 2.58 (td, J=12.98, 4.49 Hz, 1H) 2.68-2.81 (m, 1H) 3.10 (s, 3H) 7.01 (d, J=8.20 Hz, 1H) 7.29 (d, J=2.34 Hz, 1H) 7.31 (s, 1H).

Step I: 4-(4-Bromo-2-methylphenyl)-2-methyl-2-(methylsulfonyl)-N-(tetrahydro-2H-pyran-2-yloxy) butanamide 4-(4-Bromo-2-methylphenyl)-2-methyl-2-(methylsulfonyl)butanoic acid (3.28 g, 9.39 mmol), O-tetrahydro-2H-pyran-2-yl-hydroxylamine (2.19 g, 18.7 mmol), 1-hydroxy benzotriazole monohydrate (3.68 g, 24 mmol), triethylamine (3.35 mL, 24 mmol) and (3-dimethylaminopropyl)-3-ethyl-carbodiimide hydrochloride (3.59 g, 18.7 mmol) were combined followed by the addition 60 mL of dichloromethane. The reaction was allowed to stir at room temperature overnight. The reaction mixture was diluted with 20 mL of dichloromethane and 60 mL of water. The aqueous layer was extracted with dichloromethane (2×40 mL). The organics were combined, dried over magnesium sulfate, filtered and concentrated onto silica gel. Silica chromatography (30% ethyl acetate 70% heptane for 10 minutes, then 30% ethyl acetate 70% heptane to 60% ethyl acetate 40% heptane for 40 minutes) afforded the title compound as a white solid (2.11 g, 50.1%).

LC-MS m/z 448.2 (M−1)

Step J: 2-Methyl-4-(3-methylbiphenyl-4-yl)-2-(methylsulfonyl)-N-(tetrahydro-2H-pyran-2-yloxy)butanamide 4-(4-Bromo-2-methylphenyl)-2-methyl-2-(methylsulfonyl)-N-(tetrahydro-2H-pyran-2-yloxy)butanamide (250 mg, 0.558 mmol), phenyl boronic acid (102 mg, 0.837 mmol), sodium carbonate (181 mg, 1.71 mmol), Pd (II) EnCat (144 mg, 0.056 mmol, 0.39 mmol/g loading) were combined in a 2-5 mL microwave vial followed by the addition of 2 mL of dioxane, and 2 mL of water. The reaction was irradiated in a microwave at 120° C. for 40 minutes, followed by neutralization through the addition of 5 mL of aqueous 4N HCl and the mixture was extracted with ethyl acetate (3×15 mL). The organics were combined, dried over magnesium sulfate, filtered and concentrated onto silica gel. Silica chromatography (30% ethyl acetate 70% heptane for 10 minutes, then 30% ethyl acetate 70% heptane to 60% ethyl acetate 40% heptane for 40 minutes) afforded the title compound as a white solid (170 mg, 68%). LC-MS m/z 444.2 (M−1)

Step K: N-hydroxy-2-methyl-4-(3-methylbiphenyl-4-yl)-2(methylsulfonyl)butanamide 2-Methyl-4-(3-methylbiphenyl-4-yl)-2-(methylsulfonyl)-N-(tetrahydro-2H-pyran-2-yloxy)butanamide (170 mg, 0.382 mmol) was dissolved in 5 mL of dichloromethane at ambient temperature. To this was added a 4M HCl solution in dioxane (2.86 mL, 11.5 mmol) and the reaction was stirred at ambient temperature for 5 minutes. 0.5 mL of methanol was then added followed by silica gel and the mixture was concentrated to dryness. Silica chromatography (100% dichloromethane to 96% DCM 4% MeOH over 60 minutes) yielded product that contained impurities and was further triturated with a solution of 4:1 heptane:isopropanol afforded the title compound as a white solid (8 mg, 6%).

$^1$H NMR (400 MHz, METHANOL-$d_4$) δ ppm 1.69 (br. s., 3H) 2.01-2.28 (m, 1H) 2.17-2.31 (m, 1H) 2.39 (br. s., 3H) 2.55 (br. s., 3H) 2.75 (br. s., 1H) 3.04 (br. s., 3H) 7.22 (br. s., 1H) 7.29 (br. s., 2H) 7.40 (br. s., 3H) 7.56 (br. s., 2H)

Example 2

4-(3-Fluorobiphenyl-4-yl)-N-hydroxy-2-methyl-2-(methylsulfonyl)butanamide

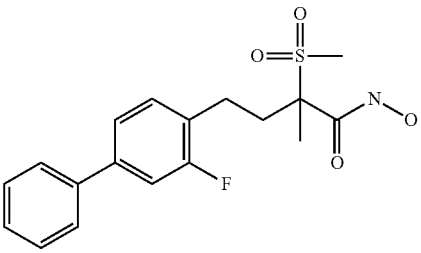 [SMILES: CC(CCc1ccc(-c2ccccc2)cc1F)(C(=O)NO)S(C)(=O)=O]

Step A: (4-Bromo-2-fluoro-phenyl)-acetonitrile

2-Fluoro-4-bromo-chloromethylbenzene (25.0 g, 112 mmol) and NaCN (6.32 g, 129 mmol) were dissolved in DMF (70 mL) and the solution was stirred under a $N_2$ atmosphere for 18 hrs at ambient temperature. The solution was poured into water (300 mL), and was extracted with EtOAc (1×1 L, 4×300 mL). The combined organic layers were dried ($Na_2SO_4$), filtered and concentrated under reduced pressure, yielding the title compound (22.5 g, 105 mmol, 93%) as a yellow oil that contained some traces of DMF. $^1$H-NMR (CDCl$_3$, 300 MHz): 3.75 (s, 2H); 7.20-7.4 (m, 3H)

Step B: 4-Bromo-2-fluoro-phenyl-acetic acid (4-Bromo-2-fluoro-phenyl)-acetonitrile (41.4 g, 174 mmol) (21.2 g, 99.1 mmol) was suspended in 30% aq. HCl (200 mL) and heated to reflux for 20 hours. After cooling to room temperature, the solids were collected by filtration, washed with water and allowed to dry in open air. The solids were azeotroped with toluene under reduced pressure to remove the final traces of water, yielding the title compound as a solid (21.7 g, 89 mmol, 94%). $^1$H-NMR (CD$_3$OD, 300 MHz): 3.68 (s, 2H); 7.20-7.4 (m, 3H)

Step C: 2-(4-Bromo-2-fluoro-phenyl)-ethanol

4-Bromo-2-fluoro-phenyl-acetic acid (36 g, 154 mmol) (40.6 g, 174 mmol) was dissolved in THF (100 mL), and cooled to 0° C. in an ice-bath. Borane (1 M in THF, 200 mL, 1.2 eq) was then added dropwise. During the addition, the temperature rose slowly to 27° C. After complete addition the ice-bath was removed and the reaction mixture was stirred for 1 hour at room temperature. The reaction mixture was added carefully to saturated aqueous $K_2CO_3$ (300 mL), and the obtained suspension was diluted with $H_2O$ (500 mL). The THF layer was separated and concentrated under reduced pressure. The aqueous layer was extracted with EtOAc (2×100 mL). The residue from the concentrated THF layer was dissolved into the combined organic layers, which was washed with brine. The organic layer was dried ($Na_2SO_4$), filtered, and concentrated under reduced pressure, yielding crude material (35.6 g) as a yellow oil, which solidified to a white solid upon standing. The crude material was purified by column chromatography (SiO$_2$; 1750 mL, 0-5% MeOH in CH$_2$Cl$_2$), yielding the title compound as a white solid (31.5 g, 144 mmol, 82%). $^1$H-NMR (CDCl3, 300 MHz): 1.50 (s, 1H); 2.95 (t, 2H); 3.92 (t, 2H); 7.18 (t, 1H); 7.28 (m, 1H)

Step D: 4-Bromo-1-(2-iodo-ethyl)-2-fluoro-benzene

The title compound was synthesized according to the same general procedure described for the synthesis of 4-bromo-1-(2-iodo-ethyl)-2-methyl-benzene in Preparation #2, Step 1, except that 2-(4-bromo-2-fluoro-phenyl)-ethanol was used instead of 2-(4-bromo-2-methylphenyl)ethanol to yield the title compound as a clear oil (5.75 g, 95.7%) $^1$H NMR (400 MHz, CHLOROFORM-d) δ ppm 3.13-3.24 (m, 2H) 3.26-3.44 (m, 2H) 7.06-7.14 (m, 1H) 7.21-7.24 (m, 1H) 7.26-7.31 (m, 1H)

Step E: 4-(4-Bromo-2-fluoro-phenyl)-2-methanesulfonyl-2-methyl-butyric acid ethyl ester The title compound was synthesized according to the general procedure of Preparation #2, Step 2, except that 4-bromo-1-(2-iodo-ethyl)-2-fluoro-benzene was used instead of 1-bromo-4-(2-iodoethyl)benzene and the reaction conducted at 40° C. to furnish the title compound as a white solid 2.2 g, (33%). $^1$H NMR (400 MHz, CHLOROFORM-d) δ ppm 1.35 (t, J=7.03 Hz, 3H) 1.72 (s, 3H) 2.19 (td, 1H) 2.38-2.48 (m, 1H) 2.52-2.61 (m, 1H) 2.72-2.86 (m, 1H) 3.05 (s, 3H) 4.28 (q, J=7.16 Hz, 2H) 7.08 (t, J=8.00 Hz, 1H) 7.19-7.25 (m, 1H) 7.25-7.34 (m, 1H).

Step F: 4-(4-Bromo-2-fluoro-phenyl)-2-methanesulfonyl-2-methyl-butyric acid

The title compound was synthesized according to the general procedure of Preparation 2, Step 3, for the preparation of (II) except that 4-(4-bromo-2-fluoro-phenyl)-2-methanesulfonyl-2-methyl-butyric acid ethyl ester was used instead of (+/−)-ethyl 4-(4-bromophenyl)-2-methyl-2-(methylsulfonyl) butanoate and that lithium hydroxide was dissolve in water prior to addition to yield as a white solid: 1.96 g, (96.2%). $^1$H NMR (400 MHz, CHLOROFORM-d) δ ppm 1.76 (s, 3H) 2.23 (td, 1H) 2.47 (td, J=12.59, 4.88 Hz, 1H) 2.63 (td, J=12.88, 4.68 Hz, 1H) 2.84 (td, J=12.49, 5.07 Hz, 1H) 3.11 (s, 3H) 7.10 (t, J=8.20 Hz, 1H) 7.20-7.23 (m, 1H) 7.25-7.34 (m, 1H)

Step G: 4-(4-Bromo-2-fluorophenyl)-2-methyl-2-(methylsulfonyl)-N-(tetrahydro-2H-pyran-2-yloxy)butanamide 4-(4-Bromo-2-fluoro-phenyl)-2-methanesulfonyl-2-methyl-butyric acid (1.96 g, 5.55 mmol), O-tetrahydro-2H-pyran-2-yl-hydroxylamine (0.910 g, 7.77 mmol), 1-hydroxybenzotriazole monohydrate (1.53 g, 9.99 mmol), triethylamine (1.39 mL, 9.99 mmol) and 1, (3-dimethylaminopropyl)-3-ethylcarbodiimide hydrochloride (1.49 g, 7.77 mmol) were combined followed by the addition 60 mL of dichloromethane. The reaction was allowed to stir at room temperature overnight, was then diluted with 20 mL of dichloromethane and 60 mL of water. The aqueous layer was re-extracted with DCM (2×40 mL). The organics were combined, dried over magnesium sulfate, filtered and concentrated onto silica gel. Silica chromatography (40% ethyl acetate 60% heptane to 40% ethyl acetate 60% heptane to 80% ethyl acetate 20% heptane for 60 minutes) afforded the title compound as a white foam 2.0 g, (79.9%). LC-MS m/z 452.1 (M−1)

Step H: 4-(3-Fluorobiphenyl-4-yl)-2-methyl-2-(methylsulfonyl)-N-(tetrahydro-2H-pyran-2-yloxy)butanamide 4-(4-Bromo-2-fluorophenyl)-2-methyl-2-(methylsulfonyl)-N-(tetrahydro-2H-pyran-2-yloxy)butanamide (250 mg, 0.558 mmol), phenyl boronic acid (91 mg, 0.747 mmol), sodium carbonate (216 mg, 2.04 mmol), and Pd (II) EnCat (144 mg, 0.056 mmol, 0.39 mmol/g loading) were combined in a 2-5 mL microwave vial followed by the addition of 2 mL of dioxane, and 2 mL of water. The reaction was irradiated in a microwave at 120° C. for 40 minutes, followed by neutralization through the addition of 5 mL of 4 N HCl in water and extracted with ethyl acetate (3×15 mL). The organics were combined, dried over magnesium sulfate, filtered and concentrated in vacuo to afford the title compound as a crude brown solid (206.7 mg, 67%). LC-MS m/z 448.3 (M−1)

Step I: 4-(3-Fluorobiphenyl-4-yl)-N-hydroxy-2-methyl-2-(methylsulfonyl)butanamide 4-(3-Fluorobiphenyl-4-yl)-2-methyl-2-(methylsulfonyl)-N-(tetrahydro-2H-pyran-2-yloxy)butanamide (170 mg, 0.382 mmol) was dissolved in 5 mL of dichloromethane at ambient temperature. To this solution was added 4M HCl (2.86 mL, 11.5 mmol) in dioxane and the solution was stirred at ambient temperature for 5 minutes. The reaction was quenched by the addition of 0.5 mL of methanol. After stirring for an additional 5 minutes, the reaction was concentrated in vacuo. Purification was performed using Shimadzu prep HPLC to provide the title compound (24.4 mg, 14.5%) LC-MS m/z 366.5 (M+1) $^1$H NMR (400 MHz, METHANOL-d$_4$) δ ppm 1.68 (s, 3H) 2.06-2.16 (m, 1H) 2.53-2.59 (m, 1H) 2.60-2.67 (m, 1H) 2.79-2.89 (m, 1H) 3.06 (s, 3H) 7.30-7.33 (m, 1H) 7.31-7.33 (m, 1H) 7.34-7.37 (m, 1H) 7.38 (d, J=3.12 Hz, 1H) 7.40-7.42 (m, 1H) 7.43-7.46 (m, 2H) 7.58-7.64 (m, 2H)

Example 3

N-Hydroxy-2-methyl-2-(methylsulfonyl)-4-(6-phenylpyridin-3-yl)butanamide

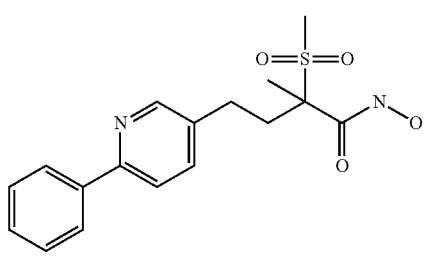 [SMILES: CC(CCc1ccc(-c2ccccc2)nc1)(C(=O)NO)S(C)(=O)=O]

Step A: 2-Bromo-5-(2-iodoethyl)pyridine

A solution of 2-(6-bromopyridin-3-yl)ethanol (2.0 g, 9.9 mmol, 1.0 equiv) in dichloromethane (31 mL) was added dropwise to a solution of imidazole (0.91 g, 13.4 mmol, 1.4 equiv), triphenylphosphine (3.3 g, 12.4 mmol, 1.3 equiv), and iodine (3.1 g, 12.4 mmol, 1.3 equiv) in dichloromethane (31 mL) at room temperature. After stirring for 6 h, the reaction was filtered and concentrated under reduced pressure. The crude material was purified by flash chromatography on silica gel (15% ethyl acetate in heptane) to provide the title compound as a white solid (2.83 g, 92%). MS (LCMS) m/z 312.0 (M+1). $^1$H NMR (400 MHz, METHANOL-d$_4$) δ ppm 3.15 (t, J=7.03 Hz, 2H) 3.43 (t, J=7.03 Hz, 2H) 7.54 (d, J=7.81 Hz, 1H) 7.61 (dd, J=8.20, 2.73 Hz, 1H) 8.22 (d, J=2.34 Hz, 1H).

Step B: Ethyl 4-(6-bromopyridin-3-yl)-2-(methylsulfonyl)butanoate

A solution of ethyl(methylsulfonyl)acetate (1090 mg, 6.6 mmol, 1.0 equiv) in DMF (11 mL) was added dropwise to a mixture of 60% sodium hydride in mineral oil (315 mg, 7.9 mmol, 1.2 equiv) in DMF (11 mL) at 0° C. The reaction was warmed to room temperature and allowed to stir for 40 min. The reaction was cooled to 0° C. and a solution of 2-bromo-5-(2-iodoethyl)pyridine (2560 mg, 8.2 mmol, 1.3 equiv) in DMF (11 mL) was added dropwise, and the reaction was allowed to stir for 3 days. Saturated aqueous ammonium chloride solution (30 mL) was added, and the mixture was extracted with ethyl acetate (3×70 mL). The combined organic layers were washed with brine (60 mL), dried over anhydrous sodium sulfate, filtered and concentrated under reduced pressure. The crude material was purified by flash chromatography (7:3 heptane/ethyl acetate) to provide the title compound as a white solid (1628 mg, 71%). MS (LCMS) m/z 352.1 (M+1). $^1$H NMR (400 MHz, CHLOROFORM-d) δ ppm 1.29-1.35 (m, 3H) 2.30-2.44 (m, 2H) 2.62-2.78 (m, 2H) 3.00 (s, 3H) 3.71 (dd, J=9.37, 4.68 Hz, 1H) 4.21-4.35 (m, 2H) 7.36-7.46 (m, 2H) 8.19 (d, J=1.56 Hz, 1H).

Step C: Ethyl 4-(6-bromopyridin-3-yl)-2-methyl-2-(methylsulfonyl)butanoate

A solution of methyl iodide (633 uL, 10.2 mmol, 2.2 equiv), potassium carbonate (895 mg, 6.5 mmol, 1.4 equiv), and ethyl 4-(6-bromopyridin-3-yl)-2-(methylsulfonyl)butanoate (1620 mg, 4.6 mmol, 1.0 equiv) in DMF (15 mL) was allowed to stir at room temperature overnight. The reaction was diluted with 0.5 M hydrochloric acid (220 mL) and was extracted with ethyl acetate (3×80 mL). The combined organic layers were washed with water (170 mL) and sodium thiosulfate (170 mL, 10% aq. solution), dried over anhydrous sodium sulfate, filtered, and concentrated under reduced pressure. The crude material was purified by flash chromatography on silica gel (7:3 heptane/ethyl acetate) to provide the title compound as a white solid (1107 mg, 66%). MS (LCMS) m/z 364.1 (M+1). $^1$H NMR (400 MHz, CHLOROFORM-d) δ ppm 1.33 (t, J=7.22 Hz, 3H) 1.69 (s, 3H) 2.12-2.23 (m, 1H) 2.39-2.59 (m, 2H) 2.69-2.79 (m, 1H) 3.02 (s, 3H) 4.27 (qd, J=7.16, 2.73 Hz, 2H) 7.35-7.43 (m, 2H) 8.20 (d, J=1.95 Hz, 1H).

Step D: 4-(6-Bromopyridin-3-yl)-2-methyl-2-(methylsulfonyl)butanoic acid

A solution of lithium hydroxide (357 mg, 8.5 mmol, 4.0 equiv) and ethyl 4-(6-bromopyridin-3-yl)-2-methyl-2-(methylsulfonyl)butanoate (775 mg, 2.1 mmol, 1.0 equiv) in 1:1:1 tetrahydrofuran-methanol-water (3 mL) was allowed to stir at room temperature for 2 h. The reaction was diluted with water (150 mL), acidified (to pH=2) with 0.5 M hydrochloric acid, and then was extracted with ethyl acetate (3×100 mL). The combined organic layers were washed with brine (100 mL), dried over anhydrous sodium sulfate, filtered, and concentrated under reduced pressure to provide the title compound (716 mg, 98%). MS (LCMS) m/z 334.1 (M−1). $^1$H NMR (400 MHz, CHLOROFORM-d) δ ppm 1.56 (s, 3H) 2.03 (td, J=12.78, 5.27 Hz, 1H) 2.31 (td, J=12.68, 4.68 Hz, 1H) 2.51 (td, J=12.98, 4.49 Hz, 1H) 2.59-2.70 (m, 1H) 2.96 (s, 3H) 7.30-7.39 (m, 2H) 8.07 (d, J=1.56 Hz, 1H).

Step E: 4-(6-Bromopyridin-3-yl)-N-hydroxy-2-methyl-2-(methylsulfonyl)butanamide DMF (1.6 uL, 0.02 mmol, 0.01 equiv) was added to a solution of oxalyl chloride (1.0 mL, 2.07 mmol, 1.0 equiv) and 4-(6-bromopyridin-3-yl)-2-methyl-2-(methylsulfonyl)butanoic acid (695 mg, 2.07 mmol, 1.0 equiv) in dichloromethane (20 mL) at room temperature. After 10 min (gas evolution subsided), O-(trimethylsilyl)hydroxylamine (843 uL, 6.2 mmol, 3.0 equiv) was added and the reaction was allowed to stir overnight. Methanol (8.8 mL) was added, and the reaction was allowed stir for an additional hour. The reaction was diluted with water (80 mL), and the resulting mixture was extracted with ethyl acetate (2×65 mL). The combined organic layers were washed with brine (40 mL), dried over anhydrous sodium sulfate, filtered, and concentrated under reduced pressure to provide the title compound as a white powder (666 mg, 92%). MS (LCMS) m/z 353.0 (M+1).

Step F: N-Hydroxy-2-methyl-2-(methylsulfonyl)-4-(6-phenylpyridin-3-yl)butanamide A solution of tetrakis(triphenylphosphine)palladium (0) (59 mg, 0.023 mmol, 0.1 equiv), sodium bicarbonate (45 mg, 0.73 mmol, 3.2 equiv), phenylboronic acid (42 mg, 0.35 mmol, 1.5 equiv), and 4-(6-bromopyridin-3-yl)-N-hydroxy-2-methyl-2-(methylsulfonyl)butanamide (81 mg, 0.23 mmol, 1.0 equiv) in 1:1 DMF-water (2 mL) was heated at 130° C. for 1 h. The reaction was diluted with 0.5 M hydrochloric acid (10 mL) and extracted with ethyl acetate (3×10 mL). The organic layers (from the acidic extraction) were discarded. The aqueous phase was basified (to pH=8) with a saturated aqueous sodium bicarbonate solution and then extracted with ethyl acetate (3×15 mL). The combined organic layers (from the second basic extraction) were dried over anhydrous sodium sulfate, filtered, and concentrated under reduced pressure. The crude material was purified by flash chromatography on silica gel (1:0-9:1 dichloromethane/methanol) to provide the title compound (29 mg, 36%). LCMS m/z 349.2 (M+1). $^1$H NMR (400 MHz, CD$_3$OD) δ 1.69 (s, 3H), 2.13 (m, 1H), 2.55-2.65 (m, 2H), 2.83 (m, 1H), 3.06 (s, 3H), 7.40-7.50 (m, 3H), 7.78-7.83 (m, 2H), 7.89-7.92 (m, 2H), 8.50 (br s, 1H).

Example 4

N-Hydroxy-2-methyl-2-(methylsulfonyl)-4-(5-phenylpyridin-2-yl)butanamide

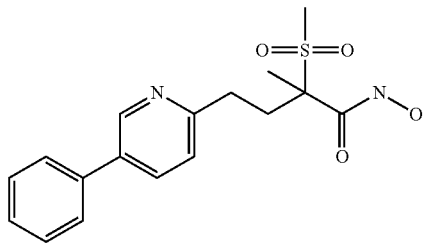 [SMILES: CC(CCc1ccc(-c2ccccc2)cn1)(C(=O)NO)S(C)(=O)=O]

Step A: 5-Bromo-2-(2-iodoethyl)pyridine

The title compound (3571 mg, 77%) was prepared from 2-(5-bromopyridin-2-yl)ethanol (Compound 6, Preparation 4) (3.0 g, 14.9 mmol) by a procedure analogous to that described for the preparation of 2-bromo-5-(2-iodoethyl)pyridine in Preparation 2, Step 1. MS (LCMS) m/z 312.0 (M+1). $^1$H NMR (400 MHz, CHLOROFORM-d) δ ppm 3.24-3.36

(m, 2H) 3.41-3.56 (m, 2H) 7.06 (d, J=8.20 Hz, 1H) 7.74 (dd, J=8.20, 2.34 Hz, 1H) 8.60 (d, J=2.34 Hz, 1H).

Step B: Ethyl 4-(5-bromopyridin-2-yl)-2-methyl-2-(methylsulfonyl)butanoate

The title compound (2030 mg, 49%) was prepared from 5-bromo-2-(2-iodoethyl)pyridine (3571 mg, 11.5 mmol) and (+/−)-2-ethanesulfonyl-propionic acid ethyl ester (2270 mg, 12.6 mmol) by a procedure analogous to that described for the preparation of compound (1) from Preparation 2, Step 2, i.e. (+/−)-ethyl 4-(4-bromophenyl)-2-methyl-2-(methylsulfonyl)butanoate. MS (LC MS) m/z 364.0 (M+1). $^1$H NMR (400 MHz, CHLOROFORM-d) δ ppm 1.31 (t, J=7.03 Hz, 3H) 1.68 (s, 3H) 2.28-2.39 (m, 1H) 2.54-2.76 (m, 2H) 2.83-2.95 (m, 1H) 3.05 (s, 3H) 4.24 (q, J=7.29 Hz, 2H) 7.05 (d, J=8.59 Hz, 1H) 7.71 (dd, J=8.20, 2.34 Hz, 1H) 8.56 (d, J=1.95 Hz, 1H).

Step C: 4-(5-Bromopyridin-2-yl)-2-methyl-2-(methylsulfonyl)butanoic acid

The title compound (1740 mg, 93%) was prepared from ethyl 4-(5-bromopyridin-2-yl)-2-methyl-2-(methylsulfonyl)butanoate (2025 mg, 5.6 mmol) by a procedure analogous to that described for the preparation of compound (II) 4-(6-bromophenyl-3-yl)-2-methyl-2-(methylsulfonyl)butanoic acid, Preparation 2, step 3. MS (LCMS) m/z 336.1 (M+1). $^1$H NMR (400 MHz, METHANOL-d$_4$) δ ppm 1.63 (s, 3H) 2.25 (ddd, J=13.27, 11.71, 5.07 Hz, 1H) 2.58 (ddd, J=13.27, 11.32, 5.07 Hz, 1H) 2.70-2.81 (m, 1H) 2.88-2.99 (m, 1H) 3.10 (s, 3H) 7.27 (d, J=8.20 Hz, 1H) 7.86-7.92 (m, 1H) 8.53 (d, J=1.95 Hz, 1H).

Step D: 4-(5-Bromopyridin-2yl)-N-hydroxy-2-methyl-2-(methylsulfonyl)butanamide The title compound (454 mg, 25%) was prepared from 4-(5-bromopyridin-2-yl)-2-methyl-2-(methylsulfonyl)butanoic acid (1740 mg, 5.2 mmol) and O-(trimethylsilyl)hydroxylamine (1810 mg, 15.5 mmol) by a procedure analogous to that described for the preparation of compound (IV) 4-(6-Bromophenyl-3-yl)-N-hydroxy-2-methyl-2-(methylsulfonyl)butanamide from Preparation 2, Step 5. MS (LCMS) m/z 351.0 (M+1). $^1$H NMR (400 MHz, CHLOROFORM-d) δ ppm 1.70 (s, 3H) 2.17-2.38 (m, 1H) 2.52-2.68 (m, 1H) 2.70-2.85 (m, 1H) 2.85-2.96 (m, 1H) 3.00 (s, 3H) 7.09 (d, J=8.20 Hz, 1H) 7.76 (dd, J=8.20, 2.34 Hz, 1H) 8.58 (d, J=2.34 Hz, 1H).

Step E: N-Hydroxy-2-methyl-2-(methylsulfonyl)-4-(5-phenylpyridin-2-yl)butanamide The title compound (2 mg, 1%) was prepared from 4-(5-bromopyridin-2-yl)-N-hydroxy-2-methyl-2-(methylsulfonyl)butanamide (151 mg, 0.43 mmol) and phenylboronic acid (79 mg, 0.65 mmol) by a procedure analogous to that described in Step F of Example 3. LCMS m/z 349.4 (M+1). $^1$H NMR (400 MHz, CD$_3$OD) δ 1.68 (s, 3H), 2.25 (m, 1H), 2.66-2.82 (m, 2H), 2.95 (m, 1H), 3.08 (s, 3H), 7.38-7.51 (m, 4H), 7.63-7.66 (m, 2H), 8.02 (dd, J=8.1, 2.3 Hz, 1H), 8.71 (dd, J=2.4, 0.8 Hz, 1H).

Example 5

Synthesis of (+/−)-N-hydroxy-2-methyl-2-(methylsulfonyl)-4-(4'-nitrobiphenyl-4-yl)butanamide

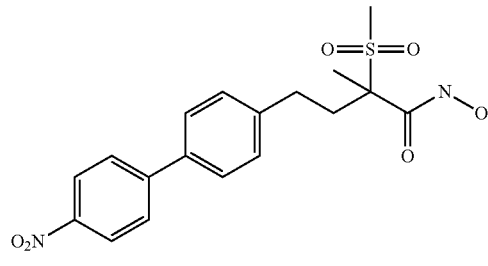 [SMILES: CC(CCc1ccc(-c2ccc([N+](=O)[O-])cc2)cc1)(C(=O)NO)S(C)(=O)=O]

Step A: (+/−)-2-Methyl-2-(methylsulfonyl)-4-(4'-nitrobiphenyl-4-yl)-N-(tetrahydro-2H-pyran-2-yloxy)butanamide Water (1.0 mL) was added to a solution of (+/−)-4-(4-bromophenyl)-2-methyl-2-(methylsulfonyl)-N-(tetrahydro-2H-pyran-2-yloxy)butanamide (0.35 g, 0.806 mmol), which may be prepared as in Preparation 2, Step 4, in 1,4-dioxane (5.0 mL). (4-nitrophenyl)boronic acid (209 mg, 1.01 mmol), cesium fluoride (0.49 mg, 3.22 mmol) and tetrakis(triphenylphosphine)palladium (0.094 g, 0.810 mmol) were added and the solution was heated to 90° C. After 4 hours the reaction was concentrated in vacuo and the resulting residue was triturated with ethyl acetate. The suspension was filtered through celite. The filtrate was washed with brine, dried (Na$_2$SO$_4$), and concentrated in vacuo. Purification on Biotage flash 40S (hexanes/ethyl 6:4-1:1) afforded the title compound as a yellow solid (700 mg, 50%). LCMS m/z 475.2 (M−1).

Step B: (+/−)-N-Hydroxy-2-methyl-2-(methylsulfonyl)-4-(4'-nitrobiphenyl-4-yl)butanamide A solution of HCl in dioxane (4.0 M, 10 mL) was added to a solution of (+/−)-2-methyl-2-(methylsulfonyl)-4-(4'-nitrobiphenyl-4-yl)-N-(tetrahydro-2H-pyran-2-yloxy)butanamide (700 mg, 1.47 mmol) in DCM (5 mL) at 0° C. The reaction was warmed to room temperature as the ice bath expired. After 4 hours the reaction was concentrated. Purification on silica by flash column chromatography (DCM/MeOH 99:1-95:5) afforded the title compound as a yellow solid (500 mg, 87%). LCMS m/z 391.1 (M−1). 1H NMR (400 MHz, DMSO-d$_6$) δ ppm 1.57 (s, 3H) 1.87-2.01 (m, 1H) 2.35-2.59 (m, 2H) 2.64-2.80 (m, 1H) 3.05 (s, 3H) 7.41 (d, J=8.20 Hz, 2H) 7.74 (d, J=8.59 Hz, 2H) 7.88-8.06 (m, 2H) 8.22-8.39 (m, 2H) 9.23 (br. s., 1H) 10.98 (s, 1H)

Example 6

4'-[(3R)-4-(Hydroxyamino)-3-methyl-3-(methylsulfonyl)-4-oxobutyl]biphenyl-4-yl dihydrogen phosphate

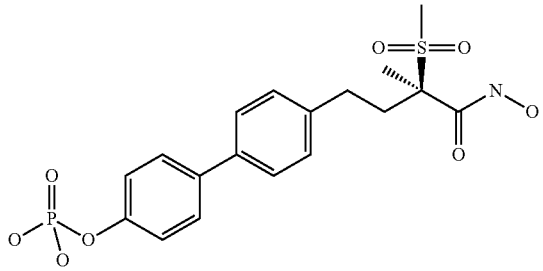 [SMILES: C[C@@](CCc1ccc(-c2ccc(OP(=O)(O)O)cc2)cc1)(C(=O)NO)S(C)(=O)=O]

Step A: Ethyl(2R)-4-(4'-hydroxybiphenyl-4-yl)-2-methyl-2-(methylsulfonyl)butanoate A mixture of palladium (II) EnCat (0.1 equiv), potassium carbonate (3.0 equiv), 4-iodophenol and ethyl(2R)-2-methyl-2-(methylsulfonyl)-4-[4-(4,4,5,5-tetramethyl-1,3,2-dioxaborolan-2-yl)phenyl]butanoate, which may be prepared as in Preparation 8A, was heated to 80° C. in 10:1 1,4-dioxane-water to provide the title compound (54%) after purification by flash chromatography on silica gel. MS (LCMS) m/z 399.5 (M+Na). $^1$H NMR (400 MHz, CHLOROFORM-d) δ ppm 1.33 (t, J=7.13 Hz, 3H) 1.72 (s, 3H) 2.18-2.28 (m, 1H) 2.47-2.58 (m, 2H) 2.72-2.84 (m, 1H) 3.04 (s, 3H) 4.22-4.31 (m, 2H) 4.91 (s, 1H) 6.85-6.92 (m, 2H) 7.17-7.24 (m, 2H) 7.40-7.51 (m, 4H).

Step B: Ethyl(2R)-4-{4'-[(di-tert-butoxyphosphoryl)oxy]biphenyl-4-yl}-2-methyl-2-(methylsulfonyl)butanoate A solution of 1H-tetrazole (2.37 g, 33.9 mmol, 3.0 equiv), di-tert-butyl-N,N-diisopropylphosphoramidite (7.42 mL, 22.6 mmol, 2.0 equiv), and ethyl(2R)-4-(4'-hydroxybiphenyl-4-yl)-2-methyl-2-(methylsulfonyl)butanoate (4.25 g, 11.3 mmol, 1.0 equiv) in tetrahydrofuran (113 mL) was allowed to stir overnight at room temperature. A solution of saturated sodium sulfite (330 mL) was added, and the mixture was extracted with dichloromethane (3×440 mL). The combined organic layers were washed with water (3×330 mL), brine (3×330 mL), dried over anhydrous sodium sulfate, filtered and concentrated under reduced pressure. The crude material was purified by flash chromatography on silica gel (50% ethyl acetate in heptane) to provide a colorless oil (5.84 g, 91%). $^1$H NMR (400 MHz, CHLOROFORM-d) δ ppm 1.33 (t, J=7.13 Hz, 3H) 1.50-1.52 (m, 18H) 1.71 (s, 3H) 2.17-2.30 (m, 1H) 2.46-2.61 (m, 2H) 2.72-2.85 (m, 1H) 3.04 (s, 3H) 4.26 (qd, J=7.13, 1.27 Hz, 2H) 7.21-7.28 (m, 4H) 7.45-7.53 (m, 4H).

Step C: (2R)-4-{4'-[(Di-tert-butoxyphosphoryl)oxy]biphenyl-4-yl}-2-methyl-2-(methylsulfonyl)butanoic acid The title compound (4.44 g, 81%) was prepared from ethyl (2R)-4-{4'-[(di-tert-butoxyphosphoryl)oxy]biphenyl-4-yl}-2-methyl-2-(methylsulfonyl)butanoate (5.8 g, 10.2 mmol) by following a procedure analogous to that described for the preparation of 4-(6-bromopyridin-3-yl)-2-methyl-2-(methylsulfonyl)butanoic acid (i.e. Example 3, Step D). MS (LCMS) m/z 539.5 (M−1). $^1$H NMR (400 MHz, CHLOROFORM-d) δ ppm 1.53-1.57 (m, 18H) 1.69 (s, 3H) 2.09-2.18 (m, 1H) 2.38-2.53 (m, 2H) 2.62-2.73 (m, 1H) 3.05 (s, 3H) 7.10 (d, J=8.20 Hz, 2H) 7.25-7.37 (m, 4H) 7.45-7.51 (m, 2H).

Step D: Di-tert-butyl 4'-{(3R)-3-methyl-3-(methylsulfonyl)-4-oxo-4-[(tetrahydro-2H-pyran-2-yloxy)amino]butyl}biphenyl-4-yl phosphate A solution of triethylamine (2.0 mL, 15 mmol, 1.8 equiv), 1-hydroxyl benzotriazole monohydrate (2.3 g, 15 mmol, 1.8 equiv), (2R)-4-{4'-[(di-tert-butoxyphosphoryl)oxy]biphenyl-4-yl}-2-methyl-2-(methylsulfonyl)butanoic acid (4.4 g, 8.2 mmol, 1.0 equiv), O-(tetrahydro-2H-pyran-2-yl)hydroxylamine (1.4 g, 12 mmol, 1.4 equiv), and N-(3-Dimethylaminopropyl)-N'-ethylcarbodiimide hydrochloride (EDCI) (2.2 g, 11 mmol, 1.4 equiv) in dichloromethane (205 mL) was allowed to stir at room temperature for 1 day. The reaction was diluted with water (600 mL) and dichloromethane (600 mL), the aqueous phase was separated and extracted with dichloromethane (2×300 mL). The combined organic layers were dried over anhydrous sodium sulfate, filtered, and concentrated under reduced pressure. The crude material was purified by flash chromatography on silica gel (60% ethyl acetate in heptane) to provide the title compound (3.29 g, 63%). MS (LCMS) m/z 638.8 (M−1).

Step E: 4'-[(3R)-4-(Hydroxyamino)-3-methyl-3-(methylsulfonyl)-4-oxobutyl]biphenyl-4-yl dihydrogen phosphate The title compound (2.03 mg, 89%) was prepared from di-tert-butyl 4'-{(3R)-3-methyl-3-(methylsulfonyl)-4-oxo-4-[(tetrahydro-2H-pyran-2-yloxy)amino]butyl}biphenyl-4-yl phosphate (3.29 g, 5.1 mmol) by following a procedure analogous to that described for Preparation 2, Step 5, compound (1V).

LCMS m/z 442.5 (M−1). $^1$H NMR (400 MHz, CO$_3$OD) δ 1.66 (s, 3H), 2.09 (m, 1H), 2.52-2.63 (m, 2H), 2.75 (m, 1H), 3.05 (s, 3H), 7.27 (dd, J=8.9, 1.3 Hz, 2H), 7.31 (d, J=8.3 Hz, 2H), 7.53 (d, J=8.4 Hz, 2H), 7.58 (br d, J=8.7 Hz, 2H).

Example 7

(2R)-4-Biphenyl-4-yl-N-hydroxy-2-methyl-2-(methylsulfonyl)butanamide

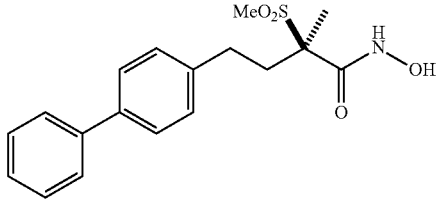 [SMILES: C[C@@](CCc1ccc(-c2ccccc2)cc1)(C(=O)NO)S(C)(=O)=O]

Step A: (2R)-4-Biphenyl-4-yl-2-methyl-2-(methylsulfonyl)-N-(tetrahydro-2H-pyran-2-yloxy)butanamide Trisdibenzylidine dipalladium (0.19 g, 0.21 mmol) was added to a mixture of potassium carbonate (1.45 g, 10.5 mmol, 5.0 equiv), (2R)-2-methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide, which may be prepared as in Preparation 8C (1.0 g, 2.1 mmol) and bromobenzene (0.26 mL, 2.5 mmol) in 1,2-dimethoxyethane-methanol (8.0 mL, 1:1). The reaction was heated to 80° C. and allowed to stir overnight. The reaction was diluted with ethyl acetate (60 mL), filtered through a pad of Celite, and concentrated under reduced pressure. The crude material was purified by flash chromatography on silica gel (heptane/ethyl acetate system) to provide the title compound as a tan gum-like material (72 mg, 8%). MS (LCMS) m/z 430.8 (M−1).

Step B: Preparation of (2R)-4-Biphenyl-4-yl-N-hydroxy-2-methyl-2-(methylsulfonyl)butanamide A solution of hydrochloric acid (4.2 mL, 4.0 M in 1,4-dioxane) was added to (2R)-4-biphenyl-4-yl-2-methyl-2-(methylsulfonyl)-N-(tetrahydro-2H-pyran-2-yloxy)butanamide (72 mg, 0.17 mmol). The reaction was allowed to stir at room temperature for 15 min, then anhydrous methanol (10 mL) was added. After 1 h, the reaction was concentrated under reduced pressure to provide a residue that was triturated with diethyl ether (35 mL). The ether was decanted off and the residual solvent was removed under reduced pressure to provide the title compound as an off-white solid (32 mg, 55%). LCMS m/z 348.2 (M+1). $^1$H NMR (400 MHz, CDCl$_3$) δ 1.62 (s, 3H), 2.09 (m, 1H), 2.45-2.56 (m, 2H), 2.65 (m, 1H), 2.96 (s, 3H), 7.21 (d, J=8.3 Hz, 2H), 7.25-7.29 (m, 1H), 7.34-7.39 (m, 2H), 7.46 (d, J=8.3 Hz, 2H), 7.49-7.52 (m, 2H).

Example 8

N-Hydroxy-4-(2'-hydroxybiphenyl-4-yl)-2-methyl-2-(methylsulfonyl)butanamide

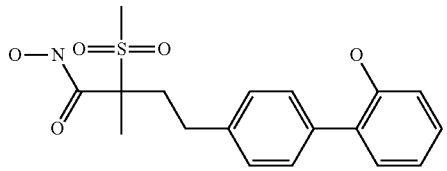

Step A

To a flask containing 2-methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide prepared as in Preparation Number 3 (150 mg, 0.312 mmol) was added 2-iodophenol (89.3 mg, 0.406 mmol), cesium fluoride (190 mg, 1.25 mmol), water (500 uL) and 1,4-dioxane (3 mL). To this mixture was added Palladium tetrakis (54.3 mg, 0.047 mmol) and the mixture was heated to 115° C. with stirring overnight. The mixture was diluted with ethyl acetate and water. The phases were separated and the crude organic extract was concentrated in vacuo to dryness. The crude material was purified via silica gel chromatography eluting with ethyl acetate/heptanes to afford 4-(2'-hydroxybiphenyl-4-yl)-2-methyl-2-(methylsulfonyl)-N-(tetrahydro-2H-pyran-2-yloxy)butanamide as solid. 19.6 mg LCMS: (M−1) 446.3.

Step B 4-(2'-Hydroxybiphenyl-4-yl)-2-methyl-2-(methylsulfonyl)-N-(tetrahydro-2H-pyran-2-yloxy)butanamide (19.6 mg, 0.044 mmol) was dissolved in methylene chloride (1 mL) at ambient temperature. To this solution was added HCl (4M in 1,4-dioxane, 0.33 mL, 1.32 mmol) and the solution was stirred at RT for 5 minutes. Methanol (100 uL) was added followed by silica gel and the mixture was concentrated to dryness. The crude material was purified via silica gel chromatography and eluted with methylene chloride/methanol to afford N-hydroxy-4-(2'-hydroxybiphenyl-4-yl)-2-methyl-2-(methylsulfonyl)butanamide as a solid. 6.5 mg

LCMS: (M−1) 362.2.

Example 9

N-Hydroxy-4-{4'-[3-(hydroxymethyl)isoxazol-5-yl]biphenyl-4-yl}-2-methyl-2-(methylsulfonyl)butanamide

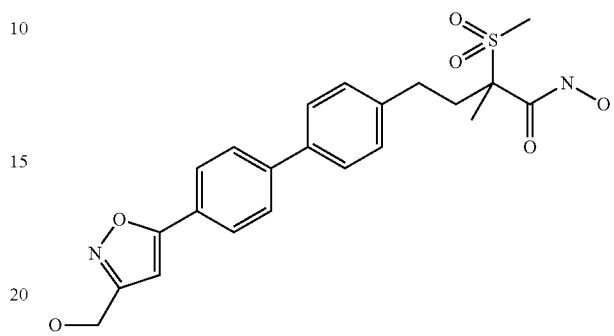

To flask containing 2-methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide, which may be prepared as in Preparation 3, (100 mg, 0.208 mmol) was added [5-(4-Bromo-phenyl)-isoxazol-3-yl]-methanol (58.2 mg, 0.229 mmol), cesium fluoride (126 mg, 0.832 mmol), water (200 uL) and 1,4-dioxane (2 mL). To this mixture was added Palladium tetrakis (35.8 mg, 0.031 mmol) and the mixture was heated to 115° C. with stirring for 3 hours. The mixture was diluted with ethyl acetate and washed with aqueous HCl (0.1 N). The phases were separated and the crude organic extract was concentrated to dryness. The crude material was purified via silica gel chromatography eluting with ethyl acetate/heptanes to afford N-hydroxy-4-{4'-[3-hhydroxymethyl)isoxazol-5-yl]biphenyl-4-yl}-2-methyl-2-(methylsulfonyl)butanamide as a solid 21 mg.

LCMS: (M+1) 445.2. $^1$H NMR (CD$_3$OD) 7.87 (2H, d, J=8.71 Hz), 7.73 (2H, d, J=8.29 Hz), 7.61 (2H, d, J=8.29 Hz), 7.34 (2H, d, J=7.88 Hz) 6.80 (1H, s), 4.67 (2H, s), 3.03 (3H, s), 2.79-2.71 (1H, m), 2.62-2.52 (2H, m), 2.12-2.04 (1H, m), 1.65 (3H, s) ppm.

Example 10

N-Hydroxy-2-methyl-2-(methylsulfonyl)-4-(4-phenoxyphenyl)butanamide

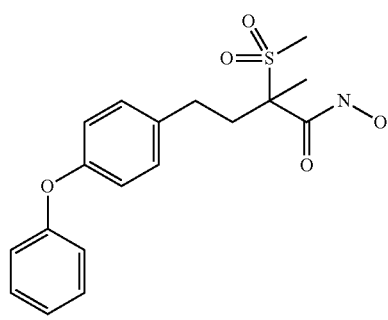 [SMILES: CC(CCc1ccc(Oc2ccccc2)cc1)(C(=O)NO)S(C)(=O)=O]

Step A: {4-[4-Ethoxy-3-methyl-3-(methylsulfonyl)-4-oxobutyl]phenyl}boronic acid

To a solution of ethyl 2-methyl-2-(methylsulfonyl)-4-[4-(4,4,5,5-tetramethyl-1,3,2-dioxaborolan-2-yl)phenyl]butanoate, which may be prepared as in Preparation Number 3, Step A, (4.75 g, 11.5 mmol) in acetone (90 mL) was added ammonium acetate (0.1 M in water, 232 mL, 23.2 mmol) and sodium periodate (7.43 g, 34.7 mmol). The mixture was stirred at ambient temperature overnight. The mixture was diluted with 1N HCl aq. and extracted with ether 2×. The combined organic extracts were dried over magnesium sulfate, filtered and concentrated in vacuo to give {4-[4-ethoxy-3-methyl-3-(methylsulfonyl)-4-oxobutyl]phenyl}boronic acid as an orange oil 3.44 g. LCMS: (M+1) 329.2

Step B: Ethyl 2-methyl-2-(methylsulfonyl)-4-(4-phenoxyphenyl)butanoate

To a solution of {4-[4-ethoxy-3-methyl-3-(methylsulfonyl)-4-oxobutyl]phenyl}boronic acid (599 mg, 1.83 mmol) in methylene chloride (3 mL) was added phenol (86 mg, 0.91 mmol), pyridine (148 uL, 1.83 mmol) and copper (II) acetate (157 mg, 0.866 mmol). The mixture was stirred at ambient temperature under open atmosphere for 2 days. Silica gel was added and the mixture was concentrated to dryness and purified via silica gel chromatography eluting with ethyl acetate/heptanes to afford ethyl 2-methyl-2-(methylsulfonyl)-4-(4-phenoxyphenyl)butanoate as an oil. 312 mg. LCMS: (M+1) 377.2

Step C: 2-Methyl-2-(methylsulfonyl)-4-(4-phenoxyphenyl)butanoic acid

To a solution of ethyl 2-methyl-2-(methylsulfonyl)-4-(4-phenoxyphenyl)butanoate (312 mg, 0.829 mmol) in tetrahydrofuran/methanol (4:1, 10 mL) was added a solution of lithium hydroxide monohydrate in water (1.66 M, 3.32 mmol). The mixture was stirred at ambient temperature overnight. The mixture was diluted with aqueous HCl (1 N in water) and extracted with ether 2×. The combined organic extracts were washed with water, dried over magnesium sulfate, filtered and concentrated to dryness to afford 2-methyl-2-(methylsulfonyl)-4-(4-phenoxyphenyl)butanoic acid as an oil. 285 mg. LCMS: (M−1) 347.3

Step D: 2-Methyl-2-(methylsulfonyl)-4-(4-phenoxyphenyl)-N-(tetrahydro-2H-pyran-2-yloxy)butanamide To a solution of 2-methyl-2-(methylsulfonyl)-4-(4-phenoxyphenyl)butanoic acid (285 mg, 0.818 mmol) in methylene chloride (8.18 mL) at ambient temperature was added 1,(3-dimethylaminopropyl)-3-ethylcarbodiimide hydrochloride (220 mg, 1.1 mmol), 1-hydroxy benzotriazole monohydrate (230 mg, 1.5 mmol), triethylamine (0.2 mL, 1.4 mmol) and O-tetrahydro-2H-pyran-2-yl-hydroxylamine (140 mg, 1.2 mmol). The resulting mixture was stirred at ambient temperature overnight. The mixture was diluted with methylene chloride and water. The phases were separated and the aqueous layer extracted with methylene chloride two times. The organic extracts were combined and dried over magnesium sulfate, filtered and concentrated in vacuo to a crude residue. The crude residue was purified via silica gel chromatography eluting with methylene chloride and methanol. The fractions containing the desired product were combined and concentrated in vacuo to afford 2-methyl-2-(methylsulfonyl)-4-(4-phenoxyphenyl)-N-(tetrahydro-2H-pyran-2-yloxy)butanamide as a solid. 247.2 mg

LCMS: (M−1) 446.3

Step E: N-Hydroxy-2-methyl-2-(methylsulfonyl)-4-(4-phenoxyphenyl)butanamide

2-Methyl-2-(methylsulfonyl)-4-(4-phenoxyphenyl)-N-(tetrahydro-2H-pyran-2-yloxy)butanamide (247.2 mg, 0.552 mmol) was dissolved in methylene chloride (10 mL) at ambient temperature. To this solution was added HCl (4M in 1,4-dioxane, 4.14 mL, 16.6 mmol) and the solution was stirred at RT for 5 minutes. Methanol (500 uL) was added followed by silica gel and the mixture was concentrated to dryness. The crude material was purified via silica gel chromatography eluting with methylene chloride/methanol to afford N-hydroxy-2-methyl-2-(methylsulfonyl)-4-(4-phenoxyphenyl)butanamide as a solid. 94.4 mg. LCMS: (M−1) 362.3

Example 11

N-Hydroxy-2-methyl-2-(methylsulfonyl)-4-[4-(1H-pyrazol-1-yl)phenyl]butanamide

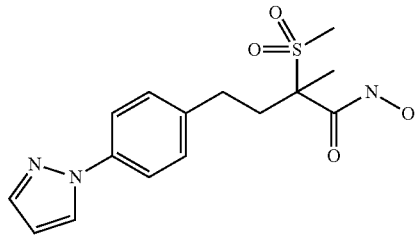 [SMILES: CC(CCc1ccc(-n2cccn2)cc1)(C(=O)NO)S(C)(=O)=O]

Step A: Ethyl 2-methyl-2-(methylsulfonyl)-4-[4-(1H-pyrazol-1-yl)phenyl]butanoate To a solution of {4-[4-ethoxy-3-methyl-3-(methylsulfonyl)-4-oxobutyl]phenyl}boronic acid which may be prepared as in Example 10, Step, A (597 mg, 1.82 mmol) in methylene chloride (3 mL) was added pyrazole (62 mg, 0.91 mmol), pyridine (147 uL, 1.82 mmol) and copper (II) acetate (157 mg, 0.866 mmol). The mixture was stirred at ambient temperature under an open atmosphere for 2 days. Silica gel was added, the mixture was concentrated to dryness and purified via silica gel chromatography eluting with ethyl acetate/heptanes to afford ethyl 2-methyl-2-(methylsulfonyl)-4-[4-(1H-pyrazol-1-yl)phenyl]butanoate as an oil. 316.9 mg. LCMS: (M+1) 351.2.

Step B: 2-Methyl-2-(methylsulfonyl)-4-[4-(1H-pyrazol-1-yl)phenyl]butanoic acid

To a solution of ethyl 2-methyl-2-(methylsulfonyl)-4-[4-(1H-pyrazol-1-yl)phenyl]butanoate (316 mg, 0.902 mmol) in tetrahydrofuran/methanol (4:1, 10 mL) was added a solution of lithium hydroxide monohydrate in water (1.8 M, 3.61 mmol). The mixture was stirred at ambient temperature overnight. The mixture was diluted with aqueous 1N HCl and extracted with ether 2×. The combined organic extracts were washed with water, dried over magnesium sulfate, filtered and concentrated to dryness to afford 2-methyl-2-(methylsulfonyl)-4-[4-(1H-pyrazol-1-yl)phenyl]butanoic acid as an oil. 286 mg. LCMS: (M−1) 321.3.

Step C: 2-Methyl-2-(methylsulfonyl)-4-[4-(1H-pyrazol-1-yl)phenyl]-N-(tetrahydro-2H-pyran-2-yloxy)butanamide To a solution of 2-Methyl-2-(methylsulfonyl)-4-[4-(1H-pyrazol-1-yl)phenyl]butanoic acid (286 mg, 0.887 mmol) in methylene chloride (8.87 mL) at ambient temperature was added 1,(3-dimethylaminopropyl)-3-ethylcarbodiimide hydrochloride (240 mg, 1.2 mmol), 1-hydroxy benzotriazole monohydrate (240 mg, 1.6 mmol), triethyl amine (220 uL, 1.6 mmol) and O-tetrahydro-2H-pyran-2-yl-hydroxylamine (150 mg, 1.3 mmol). The resulting mixture was stirred at ambient temperature overnight. The mixture was diluted with methylene chloride and water. The phases were separated and the aqueous layer was extracted with methylene chloride two times. The organic extracts were combined and dried over magnesium sulfate, filtered and concentrated in vacuo to a crude residue. The crude residue was purified via silica gel chromatography eluting with methylene chloride and methanol. The fractions containing desired product were combined and concentrated in vacuo to afford 2-methyl-2-(methylsulfonyl)-4-[4-(1H-pyrazol-1-yl)phenyl]-N-(tetrahydro-2H-pyran-2-yloxy)butanamide as a solid. 302.9 mg. LCMS: (M−1) 420.3.

Step D: N-hydroxy-2-methyl-2-(methylsulfonyl)-4-[4-(1H-pyrazol-1-yl)phenyl]butanamide 2-Methyl-2-(methylsulfonyl)-4-[4-(1H-pyrazol-1-yl)phenyl]-N-(tetrahydro-2H-pyran-2-yloxy)butanamide (302.9 mg, 0.719 mmol) was dissolved in methylene chloride (10 mL) at ambient temperature. To this solution was added HCl (4M in 1,4-dioxane, 5.39 mL, 21.6 mmol) and the solution was stirred at RT for 5 minutes. Methanol (500 uL) was added followed by silica gel and the mixture was concentrated to dryness. The crude material was purified via silica gel chromatography eluting with methylene chloride/methanol to afford N-hydroxy-2-methyl-2-(methylsulfonyl)-4-[4-(1H-pyrazol-1-yl)phenyl]butanamide as a solid. 67.8 mg. LCMS: (M−1) 336.3 $^1$H NMR (CD$_3$OD) 8.16 (1H, d, J=2.54 Hz), 7.69 (1H, d, J=1.17 Hz), 7.64 (2H, d, J=8.59), 7.36 (2H, d, J=8.40) 6.50 (1H, t), 3.03 (3H, s), 2.80-2.72 (1H, m), 2.61-2.52 (2H, m), 2.11-2.03 (1H, m), 1.65 (3H, s) ppm.

Example 12

N-Hydroxy-2-methyl-2-(methylsulfonyl)-4-[4-(phenylthio)phenyl]butanamide

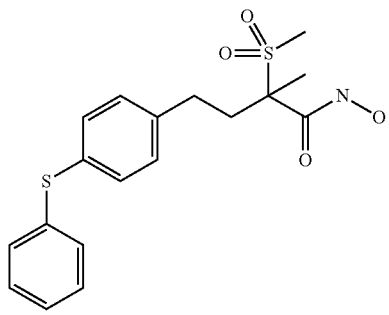 [SMILES: CC(CCc1ccc(Sc2ccccc2)cc1)(C(=O)NO)S(C)(=O)=O]

Step A: Ethyl 2-methyl-2-(methylsulfonyl)-4-[4-(phenylthio)phenyl]butanoate

To a solution of {4-[4-ethoxy-3-methyl-3-(methylsulfonyl)-4-oxobutyl]phenyl}boronic acid which may be prepared by the method described in Example 10, Step A, (600 mg, 1.83 mmol) in DMSO/water (2:1, 10 mL) at ambient temperature was added phenyl disulfide (200 mg, 0.914 mmol), [2,2']Bipyridinyl (7.20 mg, 0.046 mmol), and copper (I) iodide. The mixture was heated to 100° C. and stirred for 2 days. The mixture was allowed to cool to ambient temperature, diluted with diethyl ether and washed with water 3×. Silica gel was added to the organic extracts and the mixture was concentrated to dryness. The crude material was purified via silica gel chromatography eluting with ethyl acetate/heptanes to afford ethyl 2-methyl-2-(methylsulfonyl)-4-[4-(phenylthio)phenyl]butanoate as an oil. 348.6 mg LCMS: (M+1) 393.2.

Step B: 2-Methyl-2-(methylsulfonyl)-4-[4-(phenylthio)phenyl]-butanoic acid

To a solution of ethyl 2-methyl-2-(methylsulfonyl)-4-[4-(phenylthio)phenyl]butanoate (348.6 mg, 0.887 mmol) in tetrahydrofuran/methanol (4:1, 10 mL) was added a solution of lithium hydroxide monohydrate in water (1.78 M, 3.55 mmol). The mixture was stirred at ambient temperature overnight. The mixture was diluted with aqueous HCl (1N in water) and extracted with diethyl ether 2×. The combined organic extracts were washed with water, dried over magnesium sulfate, filtered and concentrated to dryness to afford 2-methyl-2-(methylsulfonyl)-4-[4-(phenylthio)phenyl]butanoic acid as a solid. 323 mg. LCMS: (M−1) 363.3.

Step C: 2-Methyl-2-(methylsulfonyl)-4-[4-(phenylthio)phenyl]-N-(tetrahydro-2H-pyran-2-yloxy)butanamide To a solution of 2-methyl-2-(methylsulfonyl)-4-[4-(phenylthio)phenyl]-butanoic acid (315.7 mg, 0.866 mmol) in methylene chloride (8.66 mL) at ambient temperature was added 1,(3-dimethylaminopropyl)-3-ethylcarbodiimide hydrochloride (230 mg, 1.2 mmol), 1-hydroxy benzotriazole monohydrate (240 mg, 1.6 mmol), triethyl amine (210 uL, 1.5 mmol) and O-tetrahydro-2H-pyran-2-yl-hydroxylamine (150 mg, 1.3 mmol). The resulting mixture was stirred at ambient temperature overnight. The mixture was diluted with methylene chloride and water. The phases were separated and the aqueous layer was extracted with methylene chloride two times. The organic extracts were combined and dried over magnesium sulfate, filtered and concentrated to a crude residue. The crude residue was purified via silica gel chromatography eluting with methylene chloride and methanol. The fractions containing the desired product were combined and concentrated to afford 2-methyl-2-(methylsulfonyl)-4-[4-(phenylthio)phenyl]-N-(tetrahydro-2H-pyran-2-yloxy)butanamide as a solid. 268.4 mg. LCMS: (M−1) 462.2.

Step D: N-hydroxy-2-methyl-2-(methylsulfonyl)-4-[4-(phenylthio)phenyl]butanamide To a solution of 2-methyl-2-(methylsulfonyl)-4-[4-(phenylthio)phenyl]-N-(tetrahydro-2H-pyran-2-yloxy)butanamide (268.4 mg, 0.579 mmol) in methylene chloride (3 mL) at ambient temperature was added HCl (4M in 1,4-dioxane, 4.34 mL, 17.4 mmol) and the resulting solution was stirred at RT for 5 minutes. Methanol (500 uL) was added followed by silica gel and the mixture was concentrated to dryness. The crude material was purified via silica gel chromatography eluting with methylene chloride/methanol to afford N-hydroxy-2-methyl-2-(methylsulfonyl)-4-[4-(phenylthio)phenyl]butanamide as a solid. 7.8 mg. LCMS: (M+1) 380.1.

Example 13

4-(4-Cyclohept-1-en-1-ylphenyl)-N-hydroxy-2-methyl-2-(methylsulfonyl)butanamide

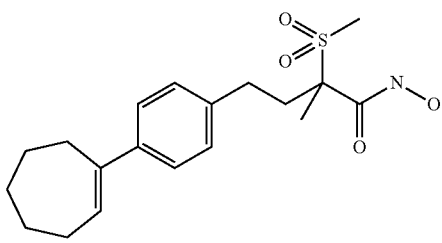 [SMILES: CC(CCc1ccc(C2=CCCCCC2)cc1)(C(=O)NO)S(C)(=O)=O]

Step A: Cyclohept-1-en-1-yl trifluoromethanesulfonate

To a solution of LDA (1.8 M in THF, 12.5 mL, 22.5 mmol) in tetrahydrofuran (70 mL) at −78° C. was added a solution of cycloheptanone (2.2 g, 19.6 mmol) in tetrahydrofuran (10 mL). The mixture was stirred at −78° C. for 45 minutes. To this solution was added 1,1,1-trifluoro-N-phenyl-N-[(trifluoromethyl)sulfonyl]methanesulfonamide (7.7 g, 21.5 mmol) in tetrahydrofuran (30 mL). The mixture was allowed to warm to ambient temperature and was stirred overnight. The mixture was diluted with diethyl ether and washed with aqueous HCl (1 N in water) and water successively. The organic extracts were dried over magnesium sulfate, filtered and concentrated to a crude residue. The residue was dissolved in heptanes and passed through a pad of silica gel eluting with heptanes. The eluant was concentrated to dryness to afford cyclohept-1-en-1-yl trifluoromethanesulfonate as a colorless oil. 2.87 g $^1$H NMR (CDCl$_3$) 5.86 (1H, t), 2.51-2.49 (2H, m), 2.16-2.12 (2H, m), 1.74-1.59 (6H, m) ppm $^{19}$F NMR (CDCl$_3$)-74.41 (3F, s) ppm.

Step B: 4-(4-Cyclohept-1-en-1-ylphenyl)-N-[(1-methoxypentyl)oxy]-2-methyl-2-(methylsulfonyl)butanamide To flask containing 2-methanesulfonyl-2-methyl-N-(tetrahydro-pyran-2-yloxy)-4-[4-(4,4,5,5-tetramethyl-[1,3,2]dioxaborolan-2-yl)-phenyl]-butyramide which may be prepared by the method described in Preparation 3 (800 mg, 01.66 mmol) was added cyclohept-1-en-1-yl trifluoromethanesulfonate (812 mg, 3.32 mmol), sodium carbonate (528 mg, 4.99 mmol), water (500 uL) and 1,4-dioxane (4 mL). To this mixture was added pd tetrakis (288 mg, 0.249 mmol) and the mixture was heated to 50° C. with stirring overnight. The mixture was diluted with ethyl acetate and washed with water 2×. The phases were separated, silica gel was added to the organic extracts and the mixture was concentrated to dryness. The crude material was purified via silica gel chromatography eluting with ethyl acetate/heptanes to afford 4-(4-cyclohept-1-en-1-ylphenyl)-N-[(1-methoxypentyl)oxy]-2-methyl-2-(methylsulfonyl)butanamide as a solid 205 mg. LCMS: (M+1) 448.3.

Step C: 4-(4-Cyclohept-1-en-1-ylphenyl)-N-hydroxy-2-methyl-2-dimethylsulfonyl)butanamide 4-(4-Cyclohept-1-en-1-ylphenyl)-N-[(1-methoxypentyl)oxy]-2-methyl-2-(methylsulfonyl)butanamide (205 mg, 0.36 mmol) was dissolved in methylene chloride (4 mL) at ambient temperature. To this solution was added HCl (4M in 1,4-dioxane, 1.82 mL, 7.30 mmol) and the solution was stirred at rt for 20 minutes. Methanol (500 uL) was added followed by silica gel and the mixture was concentrated to dryness. The crude material was purified via silica gel chromatography eluting with methylene chloride/methanol to afford 4-(4-cyclohept-1-en-1-ylphenyl)-N-hydroxy-2-methyl-2-(methylsulfonyl)butanamide as a solid. 91.5 mg. LCMS: (M+1) 366.2.

Example 14

(2R)-4-{4'-[(5R)-5-(Acetamidomethyl)-2-oxo-1,3-oxazolidin-3-yl]-2'-fluorobiphenyl-4-yl}-N-hydroxy-2-methyl-2-(methylsulfonyl)butanamide

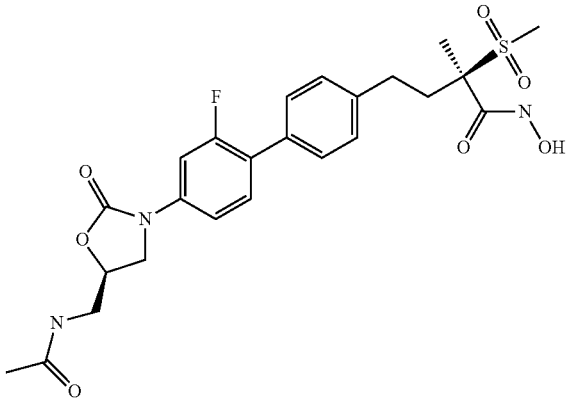 [SMILES: CC(=O)NC[C@@H]1CN(c2ccc(-c3ccc(CC[C@](C)(C(=O)NO)S(C)(=O)=O)cc3)c(F)c2)C(=O)O1]

Step A: N-({(5S)-3-[4-(5,5-dimethyl-1,3,2-dioxaborinan-2-yl)-3-fluorophenyl]-2-oxo-1,3-oxazolidin-5-yl}methyl)acetamide N-{[(5S)-3-(4-bromo-3-fluorophenyl)-2-oxo-1,3-oxazolidin-5-yl]methyl}acetamide (500 mg, 1.51 mmol) was weighed into a 20 mL vial, followed by the addition of bis (neopentyl glycolato) diboron (619 mg, 1.81 mmol), potassium acetate (593 mg, 6.04 mmol) and [1,1'-bis-(diphenylphosphino)ferrocene]-dichloropalladium (II) dcm complex (116 mg, 0.151 mmol). The reaction mixture was purged with vacuum and backfilled with nitrogen three times. To this was added N,N dimethyl formamide (10 mL). The reaction was heated at 100° C. for 72 hours, cooled to ambient temperature, filtered through celite (~1 inch), and the celite was washed with additional ethyl acetate (100 mL). The combined organics were then concentrated in vacuo. The residue was dissolved in ethyl acetate (100 mL) and organic phase was washed with water (25 mL). The aqueous layer was extracted with additional ethyl acetate (100 mL). The combined organics were then washed with brine (2×50 mL), dried (MgSO$_4$), filtered, and concentrated in vacuo. The crude material was purified by chromatography on silica gel (gradient: 80:20 hexanes:ethyl acetate) to afford the title compound as a light red solid (274 mg, 50%). MS (APCI) m/z 604.3 (M+1) 1H NMR (400 MHz, CHLOROFORM-d) δ ppm 1.04 (s, 6H) 2.01-2.04 (m, 3H) 3.56-3.68 (m, 2H) 3.69-3.78 (m, 2H) 3.80 (s, 3H) 4.07 (t, J=8.98 Hz, 1H) 4.73-4.85

(m, 1H) 6.03 (br. s., 1H) 7.20 (dd, J=8.20, 2.15 Hz, 1H) 7.37 (dd, J=11.91, 2.15 Hz, 1H) 7.73 (dd, J=8.20, 7.23 Hz, 1H).

Step B: (2R)-4-{4'-[(5R)-5-(acetamidomethyl)-2-oxo-1,3-oxazolidin-3-yl]-2'-fluorobiphenyl-4-yl}-2-methyl-2-(methylsulfonyl)-N-(tetrahydro-2H-pyran-2-yloxy)butanamide Palladium (II) EnCat (230 mg, 0.07 mmol) was added to a mixture of potassium carbonate (207 mg, 1.5 mmol), N-({(5S)-3-[4-(5,5-dimethyl-1,3,2-dioxaborinan-2-yl)-3-fluorophenyl]-2-oxo-1,3-oxazolidin-5-yl}methyl)acetamide (234 mg, 0.644 mmol), and 111a (2R)-4-(4-bromophenyl)-2-methyl-2-(methylsulfonyl)-N-(tetrahydro-2H-pyran-2-yloxy)butanamide which was prepared as in Preparation 7 (200 mg, 0.46 mmol) in dioxane:water (6 mL, 5:1) in a 20 mL sealed vial. The vial was heated overnight at 90° C. The reaction was cooled to ambient temperature, filtered through celite and the filtrate was washed with ethyl acetate (30 mL) and methanol (15 mL). The combined organics were concentrated in vacuo and purified by chromatography on silica gel (gradient: 80:20 heptanes:ethyl acetate to 0:100 heptanes:ethyl acetate, followed by ethyl acetate:methanol 90:10) to furnish the title compound as a light brown gum. Yield 50 mg, 18% theoretical yield. LCMS m/z 604.3 (M−1)

Step C: (2R)-4-{4'-[(5R)-5-(acetamidomethyl)-2-oxo-1,3-oxazolidin-3-yl]-2'-fluorobiphenyl-4-yl]-N-hydroxy-2-methyl-2-(methylsulfonyl)butanamide HCl (4.0 M in 1,4-dioxane, 1.0 mL) was added to a solution of (2R)-4-{4'-[(5R)-5-(acetamidomethyl)-2-oxo-1,3-oxazolidin-3-yl]-2'-fluorobiphenyl-4-yl}-2-methyl-2-(methylsulfonyl)-N-(tetrahydro-2H-pyran-2-yloxy)butanamide (50 mg, 0.083 mmol) in 1,4 dioxane/dichloromethane/water (1:1:1, 3 mL). After 15 minutes reaction was concentrated to give a white solid. The solid was triturated with a mixture of diethyl ether/2-propanol (10:1, 10 mL) for 2 hours. The title compound was collected as a white solid (16 mg, 37%) by filtration. LCMS m/z 522.6 (M+1) 1H NMR (400 MHz, DMSO-d$_6$) δ ppm 1.55 (s, 3H) 1.84 (s, 3H) 1.88-1.98 (m, 1H) 2.37-2.48 (m, 1H) 2.63-2.76 (m, 2H) 3.05 (s, 3H) 3.43 (t, J=5.47 Hz, 2H) 3.78 (dd, J=9.28, 6.35 Hz, 1H) 4.17 (t, J=8.98 Hz, 1H) 4.70-4.82 (m, 1H) 7.34 (d, J=8.20 Hz, 2H) 7.40 (dd, J=8.49, 2.25 Hz, 1H) 7.45-7.51 (m, 2H) 7.51-7.62 (m, 2H) 8.26 (t, J=5.86 Hz, 1H).

Example 15

(+/−)-4-[4-(Cyclopentyloxy)phenyl]-N-hydroxy-2-methyl-2-(methylsulfonyl)butanamide

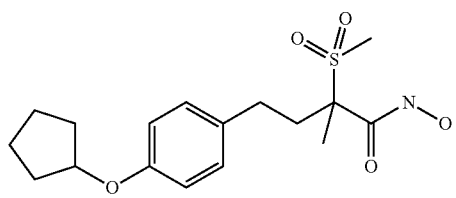 [SMILES: CC(CCc1ccc(OC2CCCC2)cc1)(C(=O)NO)S(C)(=O)=O]

Step A: 1-(Benzyloxy)-4-(2-iodoethyl)benzene

2-[4-(Benzyloxy)phenyl]ethanol was converted to the title compound following the general procedure outlined for 1-bromo-4-(2-iodoethyl)benzene in Preparation 2, step 1. The title compound was obtained as a white solid (34.32 g, 93%). $^1$H NMR (400 MHz, CHLOROFORM-d) δ ppm 3.13 (t, J=8.01 Hz, 2H) 3.33 (t, J=7.61 Hz, 2H) 5.07 (s, 2H) 6.94 (d, J=8.59 Hz, 2H) 7.12 (d, J=8.40 Hz, 2H) 7.31-7.47 (m, 5H).

Step B: Ethyl 4-[4-(benzyloxy)phenyl]-2-(methylsulfonyl)butanoate

Sodium hydride (1.80 g, 45 mmol, 60% in mineral oil) was added in three portions to a solution of ethyl (methylsulfonyl)acetate (6.70 g, 40.3 mmol) in DMF (200 mL) at 0° C. The reaction was allowed to warm to room temperature and stirred for 1 hour. 1-(Benzyloxy)-4-(2-iodoethyl)benzene was added to the solution and the reaction was stirred overnight at rt. The reaction was quenched with 1N aqueous HCl (200 mL) and extracted with ethyl acetate (3×100 mL). The combined organics were dried (MgSO$_4$), filtered and concentrated in vacuo. Chromatography on a Biotage 40 L column using 1:4 ethyl acetate in heptane afforded the title compound as a white solid (13.13 g, 86.5%). LC-MS m/z 375.2 (M−1). $^1$H NMR (400 MHz, CHLOROFORM-d) δ ppm 1.34 (t, J=7.03 Hz, 3H) 2.31-2.47 (m, 2H) 2.55-2.68 (m, 1H) 2.70-2.80 (m, 1H) 3.00 (s, 3H) 3.66-3.80 (m, 1H) 4.18-4.38 (m, 2H) 5.06 (s, 2H) 6.92 (d, J=8.59 Hz, 2H) 7.09 (d, J=8.59 Hz, 2H) 7.31-7.47 (m, 5H).

Step C: (+/−)-Ethyl 4-[4-(benzyloxy)phenyl]-2-methyl-2-(methylsulfonyl)butanoate Cesium carbonate (9.30 g, 28.5 mmol) was added to ethyl 4-[4-(benzyloxy)phenyl]-2-(methylsulfonyl)butanoate (8.86 g, 23.5 mmol) in DMF (100 mL) and stirred for 30 minutes. Iodomethane was added to the reaction followed by stirring overnight at room temperature. The reaction mixture was poured into 1N aqueous HCl (100 mL) and extracted with EtOAc (3×100 mL). The combined organics were washed with saturated aqueous sodium thiosulfate (100 mL) then dried (MgSO$_4$), filtered and concentrated in vacuo to afford a crude solid. The crude product was purified via silica gel chromatography using an eluant of ethyl acetate in heptane (10-100%) to afford the title compound as a white solid (8.35 g, 90.9%). LC-MS m/z 391.2 (M+1).

Step D: (+/−)-Ethyl 4-(4-hydroxyphenyl)-2-methyl-2-(methylsulfonyl)butanoate

Pearlman's catalyst (Pd(OH)$_2$/C, 1.19 g, 8.48 mmol) was added to a solution of (+/−)-Ethyl 4-[4-(benzyloxy)phenyl]-2-methyl-2-(methylsulfonyl)butanoate (4.73 g, 12.1 mmol) and cylcohexene (12.3 mL, 121 mmol) in ethanol (50 mL). The mixture was refluxed overnight. The reaction was filtered through celite (~1 inch), washed with ethanol (100 mL) and ethyl acetate (200 mL), and the combined filtrates were concentrated in vacuo. The crude product was purified via column chromatography using an Analogiz SF15-40 g column and eluting with 500 mL 1:9 EtOAc:Heptane, and 1 L 1:1 EtOAc:Heptane to afford the title compound as a clear liquid (3.44 g, 94.6%) LC-MS m/z 301.1 (M+1). $^1$H NMR (400 MHz, CHLOROFORM-d) δ ppm 1.33 (t, J=7.13 Hz, 3H) 1.70 (s, 3H) 2.10-2.24 (m, 1H) 2.37-2.53 (m, 2H) 2.62-2.78 (m, 1H) 3.04 (s, 3H) 4.26 (q, J=7.03 Hz, 2H) 5.77-6.01 (m, 1H) 6.77 (d, J=8.59 Hz, 2H) 7.01 (d, J=8.59 Hz, 2H).

Step E: (+/−)-Ethyl 4-[4-(cyclopentyloxy)phenyl]-2-methyl-2-(methylsulfonyl)butanoate Diethyl azodicarboxylate (40%, 220 uL, 0.48 mmol) was added to a solution of cyclopentanol (30.2 uL, 0.333 mmol), triphenylphosphine (120 mg. 0.456 mmol), and (+/−)-ethyl 4-(4-hydroxyphenyl)-2-methyl-2-(methylsulfonyl)butanoate (120 mg, 0.40 mmol) in THF (3 mL) at 0° C. under nitrogen. The reaction was allowed to warm to rt and was stirred overnight. The reaction was quenched with water (20 mL) and extracted with ethyl acetate (3×30 mL). The combined organics were dried (MgSO$_4$), filtered, and concentrated in vacuo. The crude product was purified via column chromatography using an Analogiz SF10-8 g using EtOAc in Heptane (10-50%) to afford the title compound as a clear oil (100 mg, 67.8%). LC-MS m/z 369.4 (M+1).

Step F: (+/−)-4-[4-(Cyclopentyloxy)phenyl]-2-methyl-2-(methylsulfonyl)butanoic acid (+/−)-Ethyl 4-[4-(cyclopentyloxy)phenyl]-2-methyl-2-(methylsulfonyl)butanoate was converted to the title compound following the procedure described in Preparation 2, Step 3, for preparation of (II). The title compound was obtained as a white solid (90 mg, 98%). LC-MS m/z 339.1 (M+1). $^1$H NMR (400 MHz, CHLOROFORM-d) δ ppm 1.58-1.66 (m, 2H) 1.74 (s, 3H) 1.76-1.96 (m, 6H) 2.15-2.28 (m, 1H) 2.38-2.62 (m, 2H) 2.65-2.81 (m, 1H) 3.08 (s, 3H) 4.66-4.79 (m, 1H) 6.81 (d, J=8.79 Hz, 2H) 7.09 (d, J=8.79 Hz, 2H).

Step G: (+/−)-4-[4-(Cyclopentyloxy)phenyl]-N-hydroxy-2-methyl-2-(methylsulfonyl)butanamide (+/−)-4-[4-(Cyclopentyloxy)phenyl]-2-methyl-2-(methylsulfonyl)butanoic acid was converted to the title compound following the procedure described in Preparation 2, Step 5, for the preparation of (IV). The title compound was obtained as a white solid (69 mg, 74%). LC-MS m/z 356.2. $^1$H NMR (400 MHz, METHANOL-d$_4$) δ ppm 1.55-1.69 (m, 5H) 1.70-1.85 (m, 4H) 1.85-1.96 (m, 2H) 2.01 (s, 1H) 2.40-2.57 (m, 2H) 2.58-2.69 (m, 1H) 3.04 (s, 3H) 4.74 (none, 1H) 6.80 (d, J=8.59 Hz, 2H) 7.11 (d, J=8.59 Hz, 2H).

Example 16

(+/−)-N-Hydroxy-2-methyl-2-(methylsulfonyl)-4-[4-(pyridin-2-ylmethoxy)phenyl]butanamide

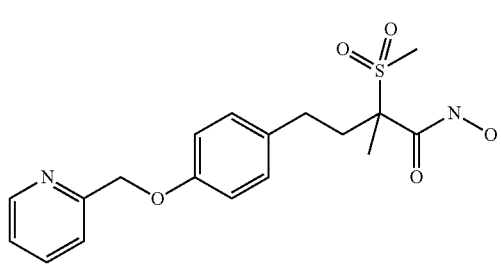 [SMILES: CC(CCc1ccc(OCc2ccccn2)cc1)(C(=O)NO)S(C)(=O)=O]

Step A: (+/−)-Ethyl 2-methyl-2-(methylsulfonyl)-4-[4-(pyridin-2-ylmethoxy)phenyl]butanoate 2-(Bromomethyl)pyridine (215 mg, mmol) was added to a suspension of cesium carbonate (485 mg, 1.49 mmol) and 4-(4-hydroxyphenyl)-2-methyl-2-(methylsulfonyl)butanoate, prepared as described in Example 15 step D (215 mg, mmol) in DMF in a 50 mL round bottom flask under N$_2$. The reaction was stirred overnight at rt, then diluted with 1N aqueous NaOH (30 mL) and extracted with ethyl acetate (3×30 mL). The combined organics were dried (MgSO$_4$), filtered, and concentrate in vacuo. The crude product was purified via flash chromatography using an Analogix SF10-4-g column and ethyl acetate in heptane (50-100° A) to afford the title compound as a yellow solid (161 mg, 58%). LC-MS m/z 392.3.

Step B: (+/−)-2-Methyl-2-(methylsulfonyl)-4-[4-(pyridin-2-ylmethoxy)phenyl]butanoic acid (+/−)-Ethyl 2-methyl-2-(methylsulfonyl)-4-[4-(pyridin-2-ylmethoxy)phenyl]butanoate was converted to the title compound following the general procedure described in Preparation 2, Step 3, for preparation of (II). The reaction was concentrated in vacuo to afford the title compound as a white solid containing salts (270 mg, >100%) which was used directly in the next reaction. LC-MS m/z 364.1. $^1$H NMR (400 MHz, DMSO-d$_6$) δ ppm 1.50 (s, 3H) 1.89-2.03 (m, 1H) 2.27-2.43 (m, 2H) 2.60-2.74 (m, 2H) 3.08 (s, 3H) 5.16 (s, 2H) 7.14 (d, J=8.59 Hz, 2H) 7.33-7.41 (m, 1H) 7.53 (d, J=7.81 Hz, 1H) 7.80-7.95 (m, 2H) 8.59 (d, J=5.07 Hz, 1H).

Step C: of (+/−)-N-Hydroxy-2-methyl-2-(methylsulfonyl)-4-[4-(pyridin-2-ylmethoxy)phenyl]butanamide (+/−)-2-Methyl-2-(methylsulfonyl)-4-[4-(pyridin-2-ylmethoxy)phenyl]butanoic acid was converted to the title compound following the general procedure described in Preparation 2, Step 5, for the preparation of (IV). The title compound was obtained as a white solid (44 mg, 17%). LC-MS m/z 379.2. $^1$H NMR (400 MHz, METHANOL-d$_4$) δ ppm 1.62 (s, 3H) 1.94-2.08 (m, 1H) 2.37-2.56 (m, 2H) 2.58-2.72 (m, 1H) 3.02 (s, 3H) 5.15 (none, 2H) 6.93 (d, J=8.79 Hz, 2H) 7.15 (d, J=8.59 Hz, 2H) 7.30-7.41 (m, 1H) 7.58 (d, J=8.01 Hz, 1H) 7.80-7.93 (m, 1H) 8.51-8.54 (m, 1H).

Example 17

(+/−)-4-[4-(2-Cyclopropylethoxy)phenyl]-N-hydroxy-2-methyl-2-(methylsulfonyl)butanamide

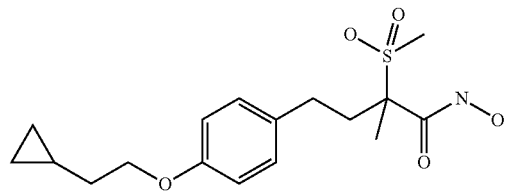

Step A: (+/−)-Ethyl 4-[4-(2-cyclopropylethoxy)phenyl]-2-methyl-2-(methylsulfonyl)butanoate 1,1'-(Azodicarbonyl)-dipiperidine (125 mg, 0.495 mmol) was added to a solution of cyclohexanol (30 mg, 0.35 mmol), tri-n-butylphosphine (12 uL), and (+/−)-ethyl 4-(4-hydroxyphenyl)-2-methyl-2-(methylsulfonyl)butanoate prepared as described in Example 15, Step D, (125 mg, 0.416 mmol) in THF (3 mL) at 0° C. under nitrogen. The reaction was allowed to warm to RT and stirred overnight, then diluted with water (30 mL) and extracted with ethyl acetate (3×30 mL). The combined organics were dried (MgSO$_4$), filtered, and concentrated in vacuo. The crude product was purified via flash chromatography using an Analogix SF10-8 g column and an eluant of 20% ethyl acetate in heptane to afford the title compound as a white solid (84 mg, 66%). LC-MS m/z 369.2. $^1$H NMR (400 MHz, CHLOROFORM-d) δ ppm 0.08-0.16 (m, 2H) 0.44-0.54 (m, 2H) 0.77-0.92 (m, 1H) 1.34 (t, J=7.03 Hz, 3H) 1.61-1.79 (m, 5H) 2.09-2.28 (m, 1H) 2.39-2.55 (m, 2H) 2.63-2.82 (m, 1H) 3.04 (s, 3H) 4.02 (t, J=6.64 Hz, 2H) 4.22-4.33 (m, 2H) 6.85 (d, J=8.79 Hz, 2H) 7.09 (d, J=8.79 Hz, 2H).

Step B: f+/−)-4-[4-(2-Cyclopropylethoxy)phenyl]-2-methyl-2-(methylsulfonyl)butanoic acid (+/−)-Ethyl 4-[4-(2-cyclopropylethoxy)phenyl]-2-methyl-2-(methylsulfonyl)butanoate was converted to the title compound following the general procedure described in Preparation 2, Step 3, for preparation of (II). The title compound was obtained as a white solid (80 mg, 100%). LC-MS m/z 369.2.

Step C: of (+/−)-4-[4-(2-Cyclopropylethoxy)phenyl]-N-hydroxy-2-methyl-2-(methylsulfonyl)butanamide (+/−)-4-[4-(2-Cyclopropylethoxy)phenyl]-2-methyl-2-(methylsulfonyl)butanoic acid was converted to the title compound following the general procedure described in Preparation 2, Step 5, for the preparation of (IV). The crude material was purified using preparatory HPLC to afford the title compound as a white solid (44 mg, 17%). LC-MS m/z 356.2. $^1$H NMR (400 MHz, METHANOL-$d_4$) δ ppm 0.06-0.23 (m, 2H) 0.40-0.55 (m, 2H) 0.79-0.97 (m, 1H) 1.55-1.73 (m, 5H) 1.92-2.09 (m, 1H) 2.36-2.57 (m, 2H) 2.57-2.74 (m, 1H) 3.03 (s, 3H) 4.01 (t, J=6.64 Hz, 2H) 6.84 (d, J=8.59 Hz, 2H) 7.13 (d, J=8.98 Hz, 2H).

Example 18

(+/−)-4-(4'-Fluoro-3-methoxybiphenyl-4-yl)-N-hydroxy-2-methyl-2-(methylsulfonyl)butanamide

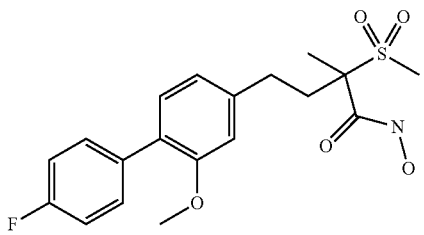 [SMILES: COc1cc(CCC(C)(C(=O)NO)S(C)(=O)=O)ccc1-c1ccc(F)cc1]

Step A:
4'-Fluoro-4-(2-iodoethyl)-3-methoxybiphenyl 2-(4'-Fluoro-3-methoxybiphenyl-4-yl)ethanol (product of Preparation 5) was converted to the title compound following the general procedure in Preparation 2, Step 1. The title compound was obtained as a white solid (1.38 g, 92.6%). $^1$H NMR (400 MHz, CHLOROFORM-d) δ ppm 3.23 (t, J=8.00 Hz, 2H) 3.40 (t, J=7.61 Hz, 2H) 3.90 (s, 3H) 7.00 (s, 1H) 7.04-7.22 (m, 4H) 7.50-7.58 (m, 2H).

Step B: (+/−)Ethyl 4-(4'-fluoro-3-methoxybiphenyl-4-yl)-2-methyl-2-dimethylsulfonyl)butanoate Cesium carbonate (2.90 g, 8.90 mmol) was added to a solution of 4'-fluoro-4-(2-iodoethyl)-3-methoxybiphenyl (1.38 g, 3.87 mmol) and ethyl 2-(methylsulfonyl) propanoate (770 mg, 4.27 mmol) in DMF (5 mL). The reaction was stirred overnight at room temperature under nitrogen. The reaction was diluted with water (60 mL) and extracted with ethyl acetate (3×60 mL). The combined organics were dried (MgSO$_4$), filtered and concentrated in vacuo to afford a clear oil. The crude oil was purified via flash chromatography using an Analogix SF25-40 g column and eluting with ethyl acetate in heptane (0-30%) to afford the title compound as a white solid (1.48 g, 93.6%). LC-MS m/z 409.5 (M+1). $^1$H NMR (400 MHz, CHLOROFORM-d) δ ppm 1.35 (t, J=7.02 Hz, 3H) 1.75 (s, 3H) 2.12-2.30 (m, 1H) 2.38-2.61 (m, 2H) 2.79-2.94 (m, 1H) 3.07 (s, 3H) 3.90 (s, 3H) 4.21-4.33 (m, 4H) 7.00 (d, J=1.56 Hz, 1H) 7.07 (dd, J=7.61, 1.76 Hz, 1H) 7.10-7.20 (m, 3H) 7.49-7.56 (m, 2H).

Step C: (+/−)-4-(4'-Fluoro-3-methoxybiphenyl-4-O-2-methyl-2-(methylsulfonyl)butanoic acid (+/−)Ethyl 4-(4'-fluoro-3-methoxybiphenyl-4-yl)-2-methyl-2-(methylsulfonyl)butanoate was converted to the title compound following the general procedure of Step 3, Preparation 2, for the formation of compound (1I) using potassium hydroxide in place of lithium hydroxide.

The title compound was obtained as a white solid (670 mg, 95.9%). LC-MS m/z 379.5 (M−1). $^1$H NMR (400 MHz, CHLOROFORM-d) δ ppm 1.78 (s, 3H) 2.22-2.35 (m, 1H) 2.37-2.51 (m, 1H) 2.54-2.66 (m, 1H) 2.83-2.95 (m, 2H) 3.11 (s, 3H) 3.90 (s, 3H).

Step D: (+/−)-4-(4'-Fluoro-3-methoxybiphenyl-4-yl)-2-methyl-2-(methylsulfonyl)-N-(tetrahydro-2H-pyran-2-yloxy)butanamide (+/−)-4-(4'-Fluoro-3-methoxybiphenyl-4-yl)-2-methyl-2-(methylsulfonyl)butanoic acid was converted to the title compound following the general procedure of step 4, Preparation 2, for the formation of compound (III) using N,N-diisopropylethylamine in place of triethylamine. The title compound was obtained as a white solid (647 mg, 76.6%) LC-MS m/z 478.6 (M−1).

Step E: (+/−)-4-(4'-Fluoro-3-methoxybiphenyl-4-yl)-N-hydroxy-2-methyl-2-(methylsulfonyl)butanamide (+/−)-4-(4'-Fluoro-3-methoxybiphenyl-4-yl)-2-methyl-2-(methylsulfonyl)-N-(tetrahydro-2H-pyran-2-yloxy)butanamide was converted to the title compound following the general procedure outlined for (+/−)-4-(4-bromophenyl)-N-hydroxy-2-methyl-2-(methylsulfonyl)butanamide as described in Preparation 2, Step 5. The title compound was obtained as a white solid (364 mg, 69%) LC-MS m/z 396.5 (M+1). $^1$H NMR (400 MHz, METHANOL-$d_4$) δ ppm 1.65 (s, 3H) 2.00-2.16 (m, 1H) 2.38-2.60 (m, 2H) 2.72-2.89 (m, 1H) 3.05 (s, 3H) 3.91 (s, 3H) 7.07-7.25 (m, 5H) 7.55-7.65 (m, 2H).

Example 19

(+/−)-4-(4'-Fluoro-3-hydroxybiphenyl-4-yl)-N-hydroxy-2-methyl-2-(methylsulfonyl)butanamide

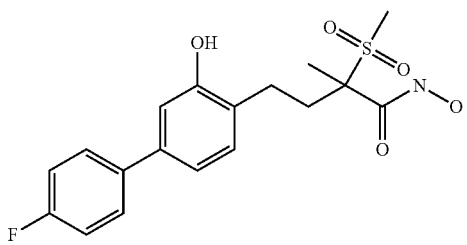 [SMILES: CC(CCc1ccc(-c2ccc(F)cc2)cc1O)(C(=O)NO)S(C)(=O)=O]

Step A: (+/−)-4-(4'-Fluoro-3-hydroxybiphenyl-4-yl)-N-hydroxy-2-methyl-2-(methylsulfonyl)butanamide Boron tribromide (750 ul, 0.75 mmol, 1.0 M in dichloromethane) was added to a solution of (+/−)-4-(4'-fluoro-3-methoxybiphenyl-4-yl)-N-hydroxy-2-methyl-2-(methylsulfonyl)butanamide prepared as in Example 18 (154 mg, 0.389 mmol) in dichloromethane (10 mL) at 0° C. The reaction was allowed to warm to rt and stirred until complete, then was diluted with water (60 mL) and extracted with ethyl acetate (3×60 mL). The combined organics were dried (MgSO$_4$), filtered and concentrated in vacuo. The solid was dissolved in 1N aqueous NaOH (60 mL), washed with ethyl acetate (3×80 mL), acidified using 1N aqueous HCl, and extracted with ethyl acetate (3×100 mL). The combined organics were dried (MgSO$_4$), filtered, and concentrated in vacuo to afford the title compound as an off-white solid (25.4 mg, 17.1%). LC-MS m/z 382.5 (M+1). $^1$H NMR (400 MHz, METHANOL-d$_4$) δ ppm 1.68 (s, 3H) 2.12-2.23 (m, 1H) 2.41-2.55 (m, 2H) 2.74-2.90 (m, 1H) 3.07 (s, 3H) 6.97-7.03 (m, 2H) 7.10-7.20 (m, 3H) 7.53-7.60 (m, 2H).

Example 20

4-(4'-Fluoro-2-methoxybiphenyl-4-yl)-N-hydroxy-2-methyl-2-(methylsulfonyl)butanamide

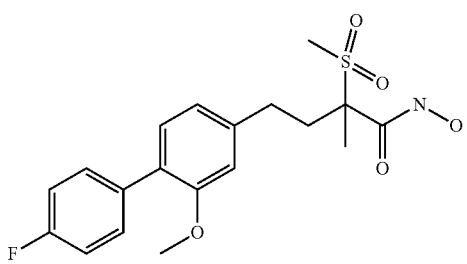 [SMILES: COc1cc(CCC(C)(C(=O)NO)S(C)(=O)=O)ccc1-c1ccc(F)cc1]

Step A: 4'-Fluoro-4-(2-iodoethyl)-2-methoxybiphenyl

The title compound (549 mg, 74.5%) was prepared from 2-(4'-fluoro-2-methoxybiphenyl-4-yl)ethanol (which may be made as described in Preparation Number 5) following the general procedure described in Preparation 2, Step 1 for 1-bromo-4-(2-iodoethyl)benzene. 1H NMR (400 MHz, CHLOROFORM-d) δ ppm 3.11 (t, J=8.00 Hz, 2H) 3.33 (t, J=7.81 Hz, 2H) 3.90 (s, 3H) 6.66-6.73 (m, 4H) 6.87 (d, J=8.59 Hz, 2H) 7.27 (s, 1H).

Step B: Ethyl 4-(4'-fluoro-2-methoxybiphenyl-4-yl)-2-(methylsulfonyl)butanoate The title compound (450 mg, 115%) containing minor solvent impurities was prepared as described in Preparation 2, Step 2, for the formation of compound (1) except that 4'-fluoro-4-(2-iodoethyl)-2-methoxybiphenyl was used. 1H NMR (400 MHz, METHANOL-d$_4$) δ ppm 2.33-2.51 (m, 3H) 2.71-2.91 (m, 3H) 3.07 (s, 3H) 3.83 (s, 3H) 3.97-4.06 (m, 1H) 4.16-4.33 (m, 3H) 6.90-6.94 (m, 1H) 6.98 (s, 1H) 7.27 (d, J=7.42 Hz, 1H) 7.64-7.70 (m, 2H) 7.70-7.75 (m, 2H).

Step C: 4-(4'-Fluoro-2-methoxybiphenyl-4-yl)-N-hydroxy-2-methyl-2-(methylsulfonyl)butanamide Lithium hydroxide (44.7 mg, 1.06 mmol) was added to a stirred solution of ethyl 4-(4'-fluoro-2-methoxybiphenyl-4-yl)-2-methyl-2-(methylsulfonyl)butanoate (435 mg, 1.06 mmol) in THF:MeOH:Water (2:2:1, 10 mL) at 0° C. The reaction was warmed to room temperature as the ice bath expired. After 18 hours the reaction was acidified to pH 4 with 1N HCl (aq) and extracted with ethyl acetate (2×). The organic layers were combined, dried (Na$_2$SO$_4$) and concentrated in vacuo to give a white solid (300 mg). The solid obtained was taken up in DCM (15 mL) at ambient temperature under a nitrogen atmosphere. To this solution was added oxalyl chloride (72 uL, 0.797 mmol) followed by 1 drop of DMF. Immediate effervescence occurred. TMSO-hydroxylamine (287 uL, 2.38 mmol) was added to the solution after five minutes resulting in the formation of a white solid. The reaction mixture was allowed to stir for an additional 60 minutes before methanol (10 mL) was added. The white solids were taken up in EtOAc (100 mL) and washed with water (75 mL). The aqueous phase was extracted with EtOAc, (40 mL). The combined organics were dried over Na$_2$SO$_4$, filtered and concentrated in vacuo to furnish a pale yellow solid. The crude material was purified by chromatography on silica gel (100% dichloromethane to 97:3 DCM: MeOH) to yield the title compound as an off white solid (110 mg, 35.3%). MS (LC/MS) m/z 396.2 (M+1). 1H NMR (400 MHz, METHANOL-d$_4$) δ ppm 1.67 (s, 3H) 2.04-2.17 (m, 1H) 2.48-2.66 (m, 2H) 2.70-2.83 (m, 1H) 3.05 (s, 3H) 3.80 (s, 3H) 6.89 (dd, J=7.81, 1.56 Hz, 1H) 6.95 (s, 1H) 7.01-7.12 (m, 2H) 7.19 (d, J=7.42 Hz, 1H) 7.41-7.50 (m, 2H).

Example 21

4-(4'-Fluoro-2-hydroxybiphenyl-4-yl)-N-hydroxy-2-methyl-2-(methylsulfonyl)butanamide

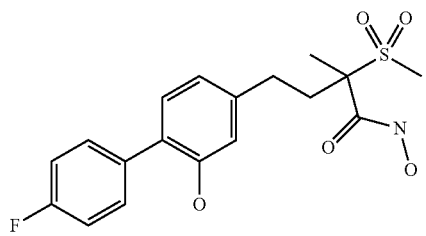 [SMILES: CC(CCc1ccc(-c2ccc(F)cc2)c(O)c1)(C(=O)NO)S(C)(=O)=O]

Step A: 4-(4'-Fluoro-2-hydroxybiphenyl-4-yl)-N-hydroxy-2-methyl-2-(methylsulfonyl)butanamide To a solution of the product of Example 20 (82 mg, 0.21 mmol) in dichloromethane (2.0 mL) under external ice cooling and a nitrogen atmosphere was added a 1.0M solution of boron tribromide in dichloromethane (0.42 mL, 0.42 mmol). The reaction mixture formed a precipitate after several minutes and was stirred for two hours under ice cooling. The reaction mixture was quenched with water 50 mL and extracted with ethyl acetate (100 mL). The organics were washed with brine 80 mL, dried over Na$_2$SO$_4$, filtered and concentrated in vacuo to furnish 80 mg of a clear oil. The residue was treated with approx 2:1 Et2O:IPA (6 mL) to attempt a trituration. However, the material was soluble; therefore, an equal portion of heptanes was added and the solution was concentrated in vacuo to 3-4 mL and a fine precipitate formed. An additional 1-2 mL of heptanes were added then the mixture was left to triturate overnight. The solids were collected via filtration to furnish the title compound as a white solid (69 mg, 87%). MS (LC/MS) m/z 382.3 (M+1).

Example 22

(+/−)-N-hydroxy-4-[4-(2H-indazol-2-yl)phenyl]-2-methyl-2-(methylsulfonyl)butanamide

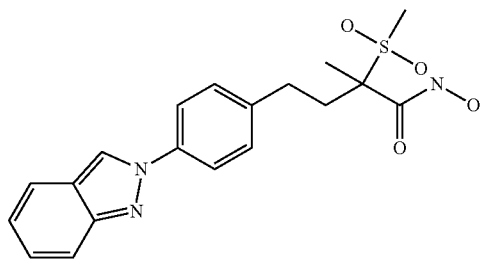 [SMILES: CC(CCc1ccc(-n2cc3ccccc3n2)cc1)(C(=O)NO)S(C)(O)O]

Step A: Tert-Butyl [4-(2-hydroxyethyl)phenyl]carbamate

Triethylamine (30 mL, 220 mmol) was added to a solution of 2-(4-aminophenyl)ethanol (26.62 g, 194 mmol) in 1,4-dioxane (200 mL) followed by the addition of di-tert-butyl dicarbonate (50 g, 230 mmol). The reaction was stirred overnight at room temperature under nitrogen. The reaction was concentrated, dissolved in ethyl acetate (500 mL), washed with water (3×100 mL) and brine (100 mL), dried (MgSO$_4$), filtered and concentrated in vacuo to afford a crude white solid. A portion of the crude white solid (10.64 g) was purified via flash chromatography using an Analogix SF40-150 g column and an eluant of ethyl acetate in heptane (30-60%) to afford the title compound as a white solid (6.45 g). $^1$H NMR (400 MHz, METHANOL-d$_4$) δ ppm 1.52 (s, 9H) 2.72-2.83 (m, 2H) 3.68-3.77 (m, 2H) 7.05-7.24 (m, 2H) 7.25-7.44 (m, 2H).

Step B: tert-Butyl [4-(2-iodoethyl)phenyl]carbamate tert-Butyl [4-(2-hydroxyethyl)phenyl]carbamate (6.45 g, 27.18 mmol) in dichloromethane (20 mL) was added dropwise to a solution of imidazole (2.04 g, 30.0 mmol), triphenylphosphine (8.60 g, 32.8 mmol), and iodine (8.28 g, 32.6 mmol) in dichloromethane (80 mL) at 0° C. The reaction was allowed to warm to rt and was stirred overnight at room temperature. The reaction was cooled to 0° C. and quenched with water (100 mL). The organic layer was separated, washed with saturated aqueous sodium thiosulfate (100 mL), water (100 mL), and brine (100 mL). The organics were dried (MgSO$_4$), filtered, and concentrated in vacuo. The crude product was purified via flash chromatography using an Analogix SF40-150 g column eluting with 30% EtOAc in heptane to afford the title compound as a white solid (8.16 g, 86.5%). $^1$H NMR (400 MHz, CHLOROFORM-d) δ ppm 1.52 (s, 9H) 3.13 (t, J=8.00 Hz, 2H) 3.27-3.35 (m, 2H) 7.12 (d, J=8.59 Hz, 2H) 7.32 (d, J=8.59 Hz, 2H).

Step C: (+/−)-Ethyl 4-{4-[(tert-butoxycarbonyl)amino]phenyl}-2-methyl-2-(methylsulfonyl)butanoate tert-Butyl [4-(2-iodoethyl)phenyl]carbamate was converted to the title compound following the general procedure described in Step 2, of Preparation 2, for the formation of compound (1). The title compound was afforded as a white solid (6.47 g, 75.8%). $^1$H NMR (400 MHz, CHLOROFORM-d) δ ppm 1.36 (t, J=7.22 Hz, 3H) 1.54 (s, 9H) 1.71 (s, 3H) 2.13-2.25 (m, 1H) 2.40-2.54 (m, 2H) 2.64-2.79 (m, 1H) 3.05 (s, 3H) 4.25-4.32 (m, 2H) 7.11 (m, J=8.39 Hz, 2H) 7.29 (d, J=8.59 Hz, 2H).

Step D: (+/−)-Ethyl 4-(4-aminophenyl)-2-methyl-2-(methylsulfonyl)butanoate

Trifluoroacetic acid (50 mL, 650 mmol) was added to a solution of (+/−)-ethyl 4-{4-[(tert-butoxycarbonyl)amino]phenyl}-2-methyl-2-(methylsulfonyl)butanoate (6.47 g, 16.2 mmol) in dicholoromethane (100 mL) at 0° C. The reaction was allowed to warm to room temperature and was stirred for 2 hours. The reaction was then concentrated; the residue was dissolved in 1N aqueous HCl (100 mL) and washed with ethyl acetate (3×100 mL). The organic layers were discarded. The aqueous layer was made basic with 1N aqueous NaOH, and extracted with ethyl acetate (3×100 mL). The combined organics were washed with water (100 mL), brine (100 mL), dried (MgSO$_4$), filtered, and concentrated in vacuo to afford a crude orange oil. The crude product was purified via flash chromatography using an Analogix SF40-150 g column and an eluant of ethyl acetate in heptane (1:1) to afford the title compound as a yellow oil (3.52 g, 72.6%). LC-MS m/z 300.5 (M+1). $^1$H NMR (400 MHz, METHANOL-d$_4$) δ ppm 1.55 (t, J=7.13 Hz, 3H) 1.88 (s, 3H) 2.24-2.39 (m, 1H) 2.56-2.77 (m, 2H) 2.84-2.98 (m, 1H) 3.31 (s, 3H) 4.42-4.49 (m, 2H) 6.91 (d, J=8.40 Hz, 2H) 7.19 (d, J=8.40 Hz, 2H).

Step E: (+/−)-Ethyl 2-methyl-2-(methylsulfonyl)-4-(4-(4{[(1E)-(2-nitrophenyl)methylene]amino}phenyl)butanoate A solution of 2-nitrobenzaldehyde (555 mg, 3.67 mmol) and (+/−)-ethyl 4-(4-aminophenyl)-2-methyl-2-(methylsulfonyl)butanoate (1.10 g 3.67 mmol) was stirred at reflux in ethanol for 2 hours. The reaction was concentrated in vacuo to afford a crude orange oil. The crude product was purified via flash chromatography using an Analogix SF25-40 g column and eluted with ethyl acetate in heptane (20-50%) to afford the title compound as a yellow oil (1.31 g, 82.4%). LC-MS m/z 433.6 (M+1). $^1$H NMR (400 MHz, CHLOROFORM-d) δ ppm 1.37 (t, J=7.12 Hz, 3H) 1.53 (s, 3H) 2.18-2.32 (m, 1H) 2.48-2.65 (m, 2H) 2.76-2.89 (m, 1H) 3.07 (s, 3H) 4.27-4.33

(m, 1H) 7.13-7.40 (m, 4H) 7.60-7.68 (m, 1H) 7.75 (t, J=7.42 Hz, 1H) 8.05-8.13 (m, 1H) 8.27-8.36 (m, 1H) 8.95 (s, 1H).

Step F: (+/−)-Ethyl 4-[4-(2H-indazol-2-yl)phenyl]-2-methyl-2-(methylsulfonyl)butanoate (+/−)-Ethyl-2-methyl-2-(methylsulfonyl)-4-(4-{[(1E)-(2-nitrophenyl)methylene]amino}phenyl) butanoate (912 mg, 2.11 mmol) was added to a solution of triethyl phosphite (10 mL) and the solution was refluxed overnight at 160° C. under nitrogen. The reaction was concentrated in vacuo and the residue was dissolved in ethyl acetate (50 mL) and washed with water (3×50 mL). The organic layer was dried (MgSO$_4$), filtered and concentrated in vacuo. The crude product was purified via flash chromatography using an Analogix SF15-24 g column and an eluant of 30% ethyl acetate in heptane to afford the title compound as a yellowish-white solid coded (499.5 mg, 56.7%). LC-MS m/z 401.5 (M+1). $^1$H NMR (400 MHz, CHLOROFORM-d) δ ppm 1.37 (t, J=7.03 Hz, 3H) 1.57 (s, 3H) 2.20-2.35 (m, 1H) 2.47-2.69 (m, 2H) 2.78-2.92 (m, 1H) 3.05-3.10 (m, 3H) 4.24-4.40 (m, 2H) 7.08-7.17 (m, 1H) 7.31-7.40 (m, 3H) 7.69-7.75 (m, 1H) 7.76-7.82 (m, 1H) 7.83-7.89 (m, 2H) 8.41 (d, J=0.98 Hz, 1H).

Step G: (+/−)-4-[4-(2H-Indazol-2-yl)phenyl]-2-methyl-2-(methylsulfonyl)butanoic acid (+/−)-Ethyl 4-[4-(2H-indazol-2-yl)phenyl]-2-methyl-2-(methylsulfonyl)butanoate was converted to the title compound following the general procedure described in Step 3, Preparation 2, for the formation of compound (1I) using potassium hydroxide in place of lithium hydroxide.

The title compound was obtained as a white solid (379 mg, 84.9%). LC-MS m/z 373.5 (M+1). $^1$H NMR (400 MHz, DMSO-d$_6$) δ ppm 1.58 (s, 0H) 2.02-2.16 (m, 0H) 2.40-2.60 (m, 2H) 2.79-2.92 (m, 1H) 3.14 (s, 3H) 7.07-7.15 (m, 1H) 7.28-7.36 (m, 1H) 7.46 (d, J=8.59 Hz, 2H) 7.68-7.81 (m, 2H) 8.03 (d, J=8.59 Hz, 2H) 9.08 (d, J=0.78 Hz, 1H).

Step H: (+/−)-4-[4-(2H-indazol-2-yl)phenyl]-2-methyl-2-(methylsulfonyl)-N-(tetrahydro-2H-pyran-2-yloxy)butanamide (+/−)-4-[4-(2H-Indazol-2-yl)phenyl]-2-methyl-2-(methylsulfonyl)butanoic acid was converted to the title compound following the general procedure described in step 4 of Preparation 2, for the preparation of compound (III) using N,N-diisopropylethylamine in place of triethylamine. The title compound was obtained as a white solid (437 mg, 87.6%) LC-MS m/z 472.7 (M+1).

Step I: (+/−)-N-hydroxy-4-[4-(2H-indazol-2-yl)phenyl]-2-methyl-2-(methylsulfonyl) butanamide (+/−)-4-[4-(2H-indazol-2-yl)phenyl]-2-methyl-2-(methylsulfonyl)-N-(tetrahydro-2H-pyran-2-yloxy)butanamide was converted to the title compound following an analogous procedure as described for the preparation of Example 11, Step D. The title compound was obtained as a white solid (232 mg, 64.6%) LC-MS m/z 388.5 (M+1). $^1$H NMR (400 MHz, METHANOL-d$_4$) δ ppm 1.69 (s, 3H) 2.06-2.21 (m, 1H) 2.54-2.69 (m, 2H) 2.76-2.91 (m, 1H) 3.07 (s, 3H) 7.10-7.18 (m, 1H) 7.32-7.39 (m, 1H) 7.48 (d, J=8.79 Hz, 2H) 7.67-7.72 (m, 1H) 7.74-7.81 (m, 1H) 7.90 (d, J=8.79 Hz, 2H) 8.75 (d, J=0.98 Hz, 1H).

Example 23

(2R)—N-hydroxy-4-(4'-hydroxybiphenyl-4-yl)-2-methyl-2-(methylsulfonyl)butanamide

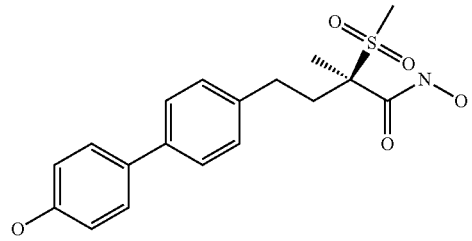 [SMILES: C[C@@](CCc1ccc(-c2ccc(O)cc2)cc1)(C(=O)NO)S(C)(=O)=O]

Step A: (2R)-2-Methyl-2-(methylsulfonyl)-N-(tetrahydro-2H-pyran-2-yloxy)-4-[4'-(tetrahydro-2H-pyran-2-yloxy)biphenyl-4-yl]butanamide Palladium (II) EnCat (575 mg, 0.22 mmol) was added to a mixture of potassium carbonate (892 mg, 3.1 mmol), (2R)-2-methyl-2-(methylsulfonyl)-N-(tetrahydro-2H-pyran-2-yloxy)-4-[4-(4,4,5,5-tetramethyl-1,3,2-dioxaborolan-2-yl)phenyl]butanamide (1.01 g, 2.1 mmol), (i.e. compound VIIa, which was prepared as in Preparation 8) and 2-(4-bromophenoxy)tetrahydro-2H-pyran (819 mg, 3.18 mmol) in dioxane: water (20 mL, 1:1) in a 50 mL flask and the reaction was heated at 90° C. overnight. The reaction was filtered and the resin was washed with ethyl acetate (50 mL) and water (50 mL). The organic layer was separated and aqueous layer extracted with ethyl acetate (2×100 mL). The combined organics were washed with saturated aqueous sodium bicarbonate (100 mL), dried (MgSO$_4$), filtered and concentrated in vacuo to furnish the crude product. The material was dissolved in a minimum amount of DCM and loaded onto an Analogix SF25-40 g column and eluted with 100% heptane (500 mL) followed by increasing EtOAc in heptane 20%-30%-50% over 500 mL volumes. The title compound was obtained as a white solid (830 mg, 74.4%) LC-MS m/z 530.8 (M−1).

Step B: (2R)—N-Hydroxy-4-(4'-hydroxybiphenyl-4-yl)-2-methyl-2-(methylsulfonyl) butanamide (2R)-2-methyl-2-(methylsulfonyl)-N-(tetrahydro-2H-pyran-2-yloxy)-4-[4'-(tetrahydro-2H-pyran-2-yloxy)biphenyl-4-yl]butanamide was converted to the title compound following the method described for the preparation of Example 11, step D. The title compound was obtained as an off-white solid (522.3 mg, 63.2%). LC-MS m/z 386.5 (M+Na+1). $^1$H NMR (400 MHz, DMSO-d$_6$) δ ppm 1.55 (s, 3H) 1.82-1.99 (m, 1H) 2.29-2.47 (m, 2H) 2.59-2.72 (m, 1H) 3.04 (s, 3H) 6.83 (d, 2H) 7.26 (d, J=8.20 Hz, 2H) 7.39-7.59 (m, 4H).

Example 24

4-(4'-Fluorobiphenyl-4-yl)-N-hydroxy-2-(methylsulfonyl)butanamide

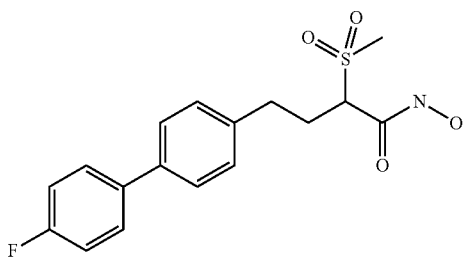 [SMILES: CS(=O)(=O)C(CCc1ccc(-c2ccc(F)cc2)cc1)C(=O)NO]

Step A: 2-(4'-Fluorobiphenyl-4-yl)ethanol

To a 2-5 mL microwave vial was added 2-(4-bromophenyl)ethanol (603 mg, 3.0 mmol), (4-fluorophenyl)boronic acid (462 mg, 3.3 mmol), sodium carbonate (973 mg, 9.0 mmol), palladium acetate (33.7 mg, 0.15 mmol), 1,4dioxane (4.5 mL) and water (4.5 mL). The mixture was irradiated in a CEN microwave at 120° C. for 10 minutes. The reaction mixture was biphasic upon reaction completion. The reaction mixture was extracted into ethyl acetate (2×150 mL) dried over $Na_2SO_4$ then filtered through a pad of celite. The organics were concentrated in vacuo and the crude material was purified by chromatography on silica gel (gradient: 70:30 heptanes:EtOAc). Isolated material still contained 2-(4-bromophenyl)ethanol, therefore, the material was triturated in heptanes to furnish the title compound as a white solid. (430 mg, 45%).

1H NMR (400 MHz, CHLOROFORM-d) δ ppm 2.84 (t, J=6.44 Hz, 1H) 2.93 (t, J=6.44 Hz, 1H) 3.86 (t, J=6.44 Hz, 1H) 3.92 (t, J=6.65 Hz, 1H) 7.07-7.19 (m, 3H) 7.32 (d, J=7.89 Hz, 1H) 7.45 (d, J=8.31 Hz, 1H) 7.48-7.58 (m, 3H)

Step B: 4-Fluoro-4'-(2-iodoethyl)biphenyl

The title compound (650 mg, 100%) was prepared following the general procedure of step 1, Preparation 2, outlined for 1-bromo-4-(2-iodoethyl)benzene except that 2-(4'-fluorobiphenyl-4-yl)ethanol (430 mg, 1.99 mmol) was used in place of 2-(4-bromophenyl)ethanol. 1H NMR (400 MHz, CHLOROFORM-d) δ ppm 3.23 (t, J=7.69 Hz, 2H) 3.39 (t, J=7.69 Hz, 2H) 7.13 (t, J=8.72 Hz, 2H) 7.24-7.30 (m, 2H) 7.48-7.58 (m, 4H).

Step C: Ethyl 4-(4'-fluorobiphenyl-4-yl)-2-(methylsulfonyl)butanoate

A mixture of ethyl(methylsulphonyl)acetate (330 mg, 1.99 mmol) in 4 mL of DMF was treated with sodium hydride (88 mg, 60% dispersion in mineral oil, 2.19 mmol), until effervescence ceased in an ice bath under nitrogen. To this was added 4-fluoro-4'-(2-iodoethyl)biphenyl (650 mg, 1.99 mmol) as a solid and the residual material was dissolved by the addition of DMF (2 mL). The mixture was warmed to room temperature, then heated at 50° C. for 2 hours. The mixture was then cooled to room temperature, poured into 60 mL of 0.5N aqueous HCl and extracted 2×60 mL with ethyl acetate. The organic phase was dried over sodium sulfate filtered and concentrated in vacuo to yield a light yellow oil with some white solid particulates. The crude yield was 840 mg. The material was purified by flash chromatography on a 40 mm flash column using 120 g silica gel eluting with 0-50% ethyl acetate/heptane. This afforded the title compound as an oil (510 mg, 70.2%). MS (LC/MS) m/z 365.2 (M+1).

1H NMR (400 MHz, CHLOROFORM-d) δ ppm 1.29-1.42 (m, 3H) 2.33-2.55 (m, 2H) 2.64-2.78 (m, 1H) 2.78-2.91 (m, 1H) 3.01 (s, 3H) 3.79 (dd, J=10.39, 4.15 Hz, 1H) 4.17-4.40 (m, 2H) 7.09-7.17 (m, 2H) 7.25 (d, J=7.89 Hz, 2H) 7.47-7.57 (m, 4H).

Step D: 4-(4'-Fluorobiphenyl-4-yl)-2-(methylsulfonyl)butanoic acid

To a solution of ethyl 4-(4'-fluorobiphenyl-4-yl)-2-(methylsulfonyl)butanoate in THF (2.2 mL) and methanol (0.6 mL) was added a solution of lithium hydroxide in water (37 mg, 1.54 mmol, 0.6 mL water) and stirred at room temperature for 30 minutes. The mixture was diluted with water (30 mL) and washed with $Et_2O$ 50 mL. The organic layer was discarded. The aqueous layer was acidified with 0.5N HCl and the white suspension was re-extracted with $Et_2O$. The ether extract was washed with brine 50 mL, dried over $Na_2SO_4$, filtered and concentrated in vacuo to afford the title compound as a white solid (113 mg, 87.5%) MS (LC/MS) m/z 335.1 (M−1)

1H NMR (400 MHz, METHANOL-$d_4$) δ ppm 2.31-2.41 (m, 2H) 2.68-2.79 (m, 1H) 2.82-2.92 (m, 1H) 3.08 (s, 3H) 3.89-3.96 (m, 1H) 7.15 (t, J=8.72 Hz, 2H) 7.31 (d, J=7.89 Hz, 2H) 7.54 (d, J=8.31 Hz, 2H) 7.58-7.64 (m, 2H).

Step E: 4-(4'-Fluorobiphenyl-4-yl)-N-hydroxy-2-(methylsulfonyl)butanamide

To a solution of 4-(4'-fluorobiphenyl-4-yl)-2-(methylsulfonyl)butanoic acid (113 mg, 0.336 mmol) in dichloromethane (1.8 mL) at ambient temperature under a nitrogen atmosphere was added a solution of oxalyl chloride (319 uL, 0.638 mmol) in dichloromethane (1.8 mL) followed by 1 drop of DMF. Immediate effervescence occurred. TMSO-hydroxylamine (89 ul, 0.739 mmol) was added to the solution after 5 minutes resulting in the formation of a white solid. 1 mL of MeOH was added to the reaction and the mixture was concentrated to dryness. The white solids were taken up in EtOAc (100 mL) and washed with water (75 mL). The aqueous phase was extracted with EtOAc (40 mL). The combined organics were dried over $Na_2SO_4$, filtered and concentrated in vacuo to furnish an off white solid. This material was triturated with diethyl ether overnight. The solid was collected via filtration and was washed with additional diethyl ether to furnish the title compound as a white solid (77 mg, 65%) MS (LC/MS) m/z 352.1 (M+1).

Example 25

N-Hydroxy-2-methyl-2-(methylsulfonyl)-4-[4-(phenoxymethyl)phenyl]butanamide

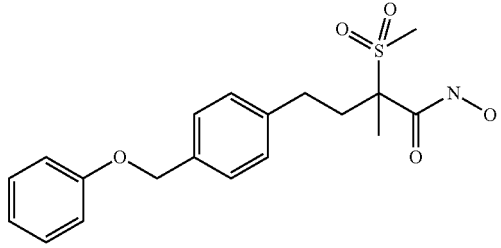 [SMILES: CC(CCc1ccc(COc2ccccc2)cc1)(C(=O)NO)S(C)(=O)=O]

Step A: 2-[4-(Phenoxymethyl)phenyl]ethanol

To a flask containing [4-(phenoxymethyl)phenyl]acetic acid (1.0 g, 4.13 mmol), in THF (20 mL) under external ice cooling was added a 1.0M sol of LiAlH$_4$ in THF (8.3 mL, 8.3 mmol) (effervescence noted). The reaction mixture was stirred for three hours under ice cooling, then allowed to stir at room temperature for 48 hours. The reaction mixture was quenched with water (4.1 mL) and 1N NaOH (24 mL) then extracted into EtOAc (200 mL). The organic layer was washed with brine (150 mL). The organics were dried over Na$_2$SO$_4$, filtered and concentrated in vacuo to furnish 1.64 g of the title compound as a white solid (174%), containing aluminum salt impurities. 1H NMR (400 MHz, CHLOROFORM-d) δ ppm 2.90 (t, J=6.64 Hz, 2H) 3.88 (t, J=6.44 Hz, 2H) 5.05 (s, 2H) 6.93-7.02 (m, 3H) 7.22-7.36 (m, 4H) 7.40 (d, J=8.20 Hz, 2H).

Step B: 1-(2-Iodoethyl)-4-(phenoxymethyl)benzene

2-[4-(Phenoxymethyl)phenyl]ethanol was converted to the title compound (960 mg, 68.7%) following the general procedure of Step 1, outlined in Preparation 2.

1H NMR (400 MHz, CHLOROFORM-d) δ ppm 3.13-3.23 (m, 2H) 3.31-3.39 (m, 2H) 5.05 (s, 2H) 6.95-7.01 (m, 3H) 7.23 (d, J=8.20 Hz, 2H) 7.28-7.36 (m, 2H) 7.41 (d, J=8.20 Hz, 2H).

Step C: Ethyl 2-methyl-2-(methylsulfonyl)-4-[4-(phenoxymethyl)phenyl]butanoate 1-(2-Iodoethyl)-4-(phenoxymethyl)benzene (960 mg, 2.84 mmol) and ethyl 2-(methylsulfonyl)propanoate (512 mg, 2.84 mmol) were converted to the title compound (1.17 g, 106%) containing minor solvent impurities following the general procedure of step 2 in Preparation 2 for the formation of compound (1). 1H NMR (400 MHz, CHLOROFORM-d) δ ppm 1.22-1.31 (m, 3H) 1.68-1.75 (m, 3H) 2.16-2.27 (m, 1H) 2.45-2.59 (m, 2H) 2.69-2.85 (m, 1H) 2.89 (s, 3H) 4.21-4.33 (m, 2H) 5.01-5.09 (m, 2H) 6.94-7.01 (m, 2H) 7.21 (d, J=8.20 Hz, 1H) 7.26-7.33 (m, 4H) 7.36-7.46 (m, 2H).

Step D: 2-Methyl-2-(methylsulfonyl)-4-[4-(phenoxymethyl)phenyl]butanoic acid The title compound (247 mg, 24%) was prepared from ethyl 2-methyl-2-(methylsulfonyl)-4-[4-(phenoxymethyl)phenyl]butanoate (1.1 g, 2.8 mmol) following the general procedure of step 3, from Preparation 2, for the formation of compound (II). MS (LC/MS) m/z 361.2 (M−1). 1H NMR (400 MHz, METHANOL-d$_4$) δ ppm 1.62-1.69 (m, 3H) 2.06-2.18 (m, 1H) 2.42-2.65 (m, 2H) 2.74-2.86 (m, 1H) 3.10 (s, 3H) 5.04 (s, 2H) 6.91 (t, J=7.42 Hz, 1H) 6.97 (d, J=7.81 Hz, 2H) 7.22-7.29 (m, 4H) 7.37 (d, J=8.20 Hz, 2H).

Step E: N-hydroxy-2-methyl-2-(methylsulfonyl)-4-[4-(phenoxymethyl)phenyl]butanamide 2-Methyl-2-(methylsulfonyl)-4-[4-(phenoxymethyl)phenyl]butanoic acid (245 mg, 0.676 mmol) was converted to the title compound (249 mg, 97.6%) following the method described for 4-(4'-fluorobiphenyl-4-yl)-N-hydroxy-2-(methylsulfonyl)butanamide in Step D, of Example 11. MS (LC/MS) m/z 378.1 (M+1).

BIOLOGICAL EXAMPLES

In order to assess the compounds biological activity, selected in-vitro assays were conducted on selected compounds. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as IC$_{50}$). Additionally, MICs (minimal inhibitory concentrations) were determined for several bacteria. The specific protocols are described below:

A) IC$_{50}$ Assay, LpxC Enzyme from *P. aeruginosa* (Labled as PA LpxC Enzyme IC$_{50}$ IC$_{50}$ determination in the LpxC enzyme assay was carried out in a similar manner to that described by Malikzay et al in the 2006 Poster, Screening LpxC (UDP-3-O—(R-3-hydroxymyristoyl)-GlcNAc deacetylase) using BioTrove Rapid Fire HTS Mass Spectrometry (aNew Lead Discovery and bInflammation and Infectious Disease, cStructural Chemistry, Schering-Plough Research Institute, Kenilworth, N.J. 07033, (BioTrove, Inc. 12 Gill St., Suite 4000, Woburn, Mass. 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1N HCl was added to stop the enzyme reaction; the plates were centrifuged, and then processed with the BioTrove Rapidfire HTMS Mass Spectrometry System. A no-enzyme control was used in calculating the IC$_{50}$ values from the percent conversion values.

B) MIC Determinations:

The in vitro antibacterial activity of compounds described in the Examples was evaluated by minimum inhibitory concentration (MIC) testing according to Clinical and Laboratory Standards Institute (CLSI, formerly NCCLS) guidelines. See: Clinical and Laboratory Standards Institute. Methods for Dilution Antimicrobial Susceptibility Tests for Bacteria that Grow Aerobically; Approved Standard-Seventh Edition. CLSI document M7-A7 [ISBN 1-56238-587-9]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Eighteenth Informational Supplement. CLSI document M100-S18 [ISBN1-56238-653-0]. Clinical and Laboratory Standards Institute. The MIC values in Tables 1, 2 and 3 are mg/L.

The following bacterial strains were used in these MIC determinations:

1) *Pseudomonas aeruginosa* UI-18: Wild-type, labeled as PA-7 in Tables 1, 2 and 3;

2) *Acinetobacter baumanii/haemolyticus*: Multidrug-resistant clinical isolate labeled as AB-3167 in Tables 1, 2 and 3;

3) *Escherichia coli* EC-1: VOGEL, mouse virulent labeled as EC-1 in Tables 1, 2 and 3;

4) *Klebsiella pneumoniae*: Ciprofloxacin-resistant isolate, expresses extended-spectrum beta-lactamases (ESBL), clinical isolate, labeled as KP-3700 in Tables 1, 2, and 3.

The following results were obtained with the final products described in Examples 1-25:

TABLE 1

| Example Number | PA LpxC enzyeme IC50 uM | AB-3167 | EC-1: | KP-3700 | PA-7 |
|---|---|---|---|---|---|
| Example 1 | 0.00168 | 16 | 2 | 8 | 4 |
| Example 2 | 0.00026 | 16 | 1 | 4 | 1 |
| Example 3 |  | ≥64 | 16 | ≥64 | 16 |
| Example 4 |  | ≥64 | 16 | ≥64 | 8 |
| Example 5 | 0.00012 | 32 | 0.5 | 1 | 0.5 |
| Example 6 | 0.0881 | ≥64 | ≥64 | ≥64 | ≥64 |
| Example 7 | 0.00031 and 0.00047 | 16 | 0.5 | 2 | 0.5 |
| Example 8 |  | ≥64 | ≥64 | ≥64 | 8 |
| Example 9 | 0.00032 | 32 | 0.125 | 4 | 2 |
| Example 10 |  | 32 | 16 | 32 | 8 |
| Example 11 |  | ≥64 | ≥64 | ≥64 | 16 |
| Example 12 | 0.0119 | 8 | 8 | 32 | 8 |
| Example 13 | 0.00029 | 0.5 | 2 | 4 | 1 |
| Example 14 | 0.00148 | ≥64 | 16 | ≥64 | 32 |
| Example 15 |  | 32 | 16 | ≥64 | 4 |
| Example 16 | 0.00501 | ≥64 | ≥64 | ≥64 | 16 |
| Example 17 | 0.00136 | 32 | 32 | ≥64 | 8 |
| Example 18 | 0.00063 | 16 | 4 | 16 | 4 |
| Example 19 | 0.00343 | ≥64 | 8 | 32 | 16 |
| Example 20 |  | ≥64 | 1 | 8 | 16 |
| Example 21 | 0.0154 | ≥64 | 16 | ≥64 | 16 |
| Example 22 |  | ≥64 | 4 | 8 | 4 |
| Example 23 | 0.00018 | ≥64 | 4 | 8 | 2 |
| Example 24 |  | 32 | 32 | 32 | 1 |
| Example 25 | 0.00238 | 16 | 4 | 16 | 8 |

Examples 26-234

In addition to the Examples above, a number of compounds were generated via combinatorial chemistry. Table 2 below lists these compounds by name, provides characterization data such as liquid chromatography-mass spectrometry and retention times. Table 2 also provides selected biological data using the same protocols as described above for Examples 1-25.

The compounds described below in Table 2 form a subset of those described by Formula I. In all of these compounds $R^1$ and $R^2$ are methyl, X is $CH_2$, A is unsubstituted phenyl, L is absent, D forms an aryl or heteroaryl ring, and both G and T may be absent or present and are as defined above in Formula I.

These compounds were generally produced in the following manner. (+/−)-4-(4-Bromophenyl)-N-hydroxy-2-methyl-2-(methylsulfonyl)butanamide (100 mg, 0.266 mmol (1 eq)), which may be produced as in Preparation 2, was combined with an appropriately substituted boronic derivative, i.e. a G-T-D moiety corresponding to the desired final product, ((0.404 mmol) (1.5 eq)) into a 2-5 mL microwave vial followed by the addition of a catalytic amount of Palladium (II) EnCat catalyst (approx 10 mol %), potassium carbonate (1 mL of 0.123M in water (~3 eq) and 1 mL of dioxane. The microwave vial was sealed and irradiated at 120° C. for 40 minutes. The reaction was filtered through a thin pad of celite and rinsed with ethyl acetate (2-5 mL). The solvents removed via Genevac, followed by a DMSO dilution (approx 100 mg/mL) and transferred to a 96 well plate for purification. The material was purified via reverse phase HPLC methods and purity determined by HPLC with a corresponding retention time HPLC Method: (HPLC 0.05% TFA 95% 5% to 5% 95% Water Acetonitrile). A few of the compounds below in Table 2 were produced individually, not by combinatorial methods, but the teachings above could be used to generate the compound.

In Table 2 below, column 2 provides the IUPAC name; column's 3-7 provide in-vitro biological data, column 8 reports the mass spectrometry data generated via LCMS and column 9 reports LCMS retention times. The in-vitro data in column's 3-7 was generated in the same manner as that described in Table I above. The LCMS retention times (LCMS-RT) reported in column 9 were generated in the following manner:
1) Acidic-labelled as "a" in column 9
   Gradients:
   0.05% TFA 95_5 to 5_95 Water_ACN
   Flow rate: 1.3 mL/min
   Column dimensions: Acquity HPLC BEH C18 1.7 μm 2.1×30 mm.
   Run time: 1.1 minutes
2) Basic-labelled as "b" in column 9
   Gradients:
   Solvent A: 0.06% NH4OH (in water)
   Solvent B: 0.06% NH4OH (in acetonitrile)

| Time (min) | % A | % B |
|---|---|---|
| 0 | 95 | 5 |
| 0.4 | 95 | 5 |
| 3.2 | 5 | 95 |
| 3.5 | 5 | 95 |
| 4.0 | 95 | 5 |

Flow rate: 2 mL/min
Column dimensions: Not currently available
Run time: 4 minutes LCMS data and retention times were not available for all compounds. This could be due to errors in computation, inability to locate data, errors in methodology, machinery failure etc. ("na" in column's 8 or 9 means that such data is not available).

TABLE 2

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 26 | 4-biphenyl-4-yl-N-hydroxy-2-methyl-2-(methylsulfonyl)butanamide |  | 4 | 4 | 8 | 1 | 100 | na |
| 27 | 4-(4'-fluorobiphenyl-4-yl)-N-hydroxy-2-methyl-2-(methylsulfonyl)butanamide |  | 8 | 2 | 4 | 1 | 73 | 1.65[b] |
| 28 | 4-(4'-cyanobiphenyl-4-yl)-N-hydroxy-2-(methylsulfonyl)butanamide |  | ≥64 | 32 | ≥64 | 2 | 100 | 1.27[b] |
| 29 | 4-(4'-cyanobiphenyl-4-yl)-N-hydroxy-2-methyl-2-(methylsulfonyl)butanamide |  | ≥64 | 1 | 2 | 1 | 100 | 1.32[b] |
| 30 | (2R)-4-(4'-fluorobiphenyl-4-yl)-N-hydroxy-2-(methylsulfonyl)butanamide |  | 32 | 8 | 16 | 1 | 100 | 1.37[b] |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 31 | (2S)-4-(4'-fluorobiphenyl-4-yl)-N-hydroxy-2-(methylsulfonyl)butanamide | | ≥64 | 16 | ≥64 | 2 | 100 | 1.37[b] |
| 32 | 4-(4-bromophenyl)-N-hydroxy-2-methyl-2-(methylsulfonyl)butanamide | | ≥64 | 32 | ≥64 | 32 | 100 | 0.36[a] |
| 33 | 4-(3',4'-dimethoxybiphenyl-4-yl)-N-hydroxy-2-methyl-2-(methylsulfonyl)butanamide | | ≥64 | 16 | 32 | 16 | 100 | 0.42[a] |
| 34 | N-hydroxy-4-[4'-(2-hydroxyethyl)biphenyl-4-yl]-2-methyl-2-(methylsulfonyl)butanamide | 0.000331 | ≥64 | 4 | 8 | 4 | 100 | 0.35[a] |
| 35 | 4-{4-[6-(dimethylamino)pyridin-3-yl]phenyl}-N-hydroxy-2-methyl-2-(methylsulfonyl)butanamide | | ≥64 | 4 | 16 | 32 | 100 | 0.27[a] |
| 36 | 4-biphenyl-4-yl-N-hydroxy-2-(methylsulfonyl)butanamide | | 32 | 16 | 16 | 2 | na | na |
| 37 | 4-{4-[6-(dimethylamino)-5-methylpyridin-3-yl]phenyl}-N-hydroxy-2-methyl-2-(methylsulfonyl)butanamide | | ≥64 | 16 | ≥64 | 16 | na | na |
| 38 | 4-(2',5'-difluorobiphenyl-4-yl)-N-hydroxy-2-methyl-2-(methylsulfonyl)butanamide | 0.000752 | 16 | 2 | 32 | 1 | 100 | 0.44[a] |
| 39 | N-hydroxy-2-methyl-2-(methylsulfonyl)-4-[4-(2-morpholin-4-ylpyrimidin-5-yl)phenyl]butanamide | | ≥64 | 4 | 32 | ≥64 | 94 | 0.32[a] |
| 40 | N-hydroxy-2-methyl-2-(methylsulfonyl)-4-[4'-(methylthio)biphenyl-4-yl]butanamide | na | 16 | 0.5 | 2 | 2 | na | na |
| 41 | 4-(2'-fluoro-6'-methoxybiphenyl-4-yl)-N-hydroxy-2-methyl-2-(methylsulfonyl)butanamide | | ≥64 | 16 | ≥64 | 8 | 100 | 0.45[a] |
| 42 | 4-(3'-fluorobiphenyl-4-yl)-N-hydroxy-2-methyl-2-(methylsulfonyl)butanamide | 0.000335 | ≥64 | 2 | 4 | 0.5 | na | na |
| 43 | N-hydroxy-4-(3'-isopropylbiphenyl-4-yl)-2-methyl-2-(methylsulfonyl)butanamide | | 4 | 4 | 16 | 8 | 100 | 0.53[a] |
| 44 | 4-(4'-chlorobiphenyl-4-yl)-N-hydroxy-2-methyl-2-(methylsulfonyl)butanamide | 6.69E−05 | 16 | 0.5 | 1 | 0.5 | na | na |
| 45 | 4-(4'-cyano-3'-fluorobiphenyl-4-yl)-N-hydroxy-2-methyl-2-(methylsulfonyl)butanamide | | ≥64 | 0.5 | 4 | 1 | 100 | 0.41[a] |
| 46 | N-hydroxy-2-methyl-2-(methylsulfonyl)-4-[4-(4-methyl-2-thienyl)phenyl]butanamide | | ≥64 | 2 | 4 | 2 | na | na |
| 47 | N-hydroxy-4-[4'-(3-hydroxypropyl)biphenyl-4-yl]-2-methyl-2-(methylsulfonyl)butanamide | 0.000132 | ≥64 | 0.5 | 2 | 1 | 100 | 0.37[a] |
| 48 | 4-(2',5'-dimethoxybiphenyl-4-yl)-N-hydroxy-2-methyl-2-(methylsulfonyl)butanamide | | 16 | 16 | ≥64 | ≥64 | 100 | 0.43[a] |
| 49 | N-hydroxy-4-(4'-isopropoxybiphenyl-4-yl)-2-methyl-2-(methylsulfonyl)butanamide | | 8 | 2 | 4 | 4 | 97 | 0.46[a] |
| 50 | 4-(2'-fluorobiphenyl-4-yl)-N-hydroxy-2-methyl-2-(methylsulfonyl)butanamide | 0.000731 | 16 | 2 | 8 | 0.5 | 95 | 1.45[b] |
| 51 | N-hydroxy-4-(4'-hydroxybiphenyl-4-yl)-2-methyl-2-(methylsulfonyl)butanamide | 0.000922 | ≥64 | 16 | 16 | 2 | 100 | 0.33[a] |
| 52 | 4-(3',5'-dimethylbiphenyl-4-yl)-N-hydroxy-2-methyl-2-(methylsulfonyl)butanamide | | 8 | 2 | 4 | 2 | 100 | 0.47[a] |
| 53 | 4-(2',4'-difluorobiphenyl-4-yl)-N-hydroxy-2-methyl-2-(methylsulfonyl)butanamide | | 8 | 1 | 4 | 0.5 | na | na |
| 54 | 4-(2',6'-difluorobiphenyl-4-yl)-N-hydroxy-2-methyl-2-(methylsulfonyl)butanamide | | 16 | 4 | 16 | 1 | 100 | 0.45[a] |
| 55 | N-hydroxy-4-(4'-methoxybiphenyl-4-yl)-2-methyl-2-(methylsulfonyl)butanamide | | 16 | 0.5 | 2 | 0.5 | na | na |
| 56 | N-hydroxy-2-methyl-2-(methylsulfonyl)-4-[3'-(methylthio)biphenyl-4-yl]butanamide | 0.000417 | 8 | 2 | 4 | 2 | 100 | 0.47[a] |
| 57 | N-hydroxy-4-[4-(1H-indol-5-yl)phenyl]-2-methyl-2-(methylsulfonyl)butanamide | 0.000295 | 8 | 0.5 | 8 | 0.5 | 100 | 0.38[a] |
| 58 | N-hydroxy-2-methyl-4-(2'-methylbiphenyl-4-yl)-2-(methylsulfonyl)butanamide | | 32 | 8 | 32 | 4 | 100 | 1.52[b] |
| 59 | 4-(2',3'-dichlorobiphenyl-4-yl)-N-hydroxy-2-methyl-2-(methylsulfonyl)butanamide | 0.000213 | 2 | 0.5 | 2 | 2 | 100 | 0.52[a] |
| 60 | N-hydroxy-4-(4'-methoxy-2'-methylbiphenyl-4-yl)-2-methyl-2-(methylsulfonyl)butanamide | | ≥64 | 4 | 16 | 4 | na | na |
| 61 | N-hydroxy-2-methyl-2-(methylsulfonyl)-4-(4-pyridin-3-ylphenyl)butanamide | | ≥64 | ≥64 | ≥64 | 16 | 100 | 0.21[a] |
| 62 | 4-(2',3'-difluorobiphenyl-4-yl)-N-hydroxy-2-methyl-2-(methylsulfonyl)butanamide | 0.000185 | 16 | 0.5 | 16 | 0.25 | 100 | 0.45[a] |
| 63 | N-hydroxy-4-(4'-isobutylbiphenyl-4-yl)-2-methyl-2-(methylsulfonyl)butanamide | 0.000356 | 8 | 2 | 4 | 16 | 85 | 1.83[b] |
| 64 | 4-(3'-cyanobiphenyl-4-yl)-N-hydroxy-2-methyl-2-(methylsulfonyl)butanamide | 0.000739 | ≥64 | 4 | 8 | 2 | 100 | 0.4[a] |
| 65 | 4-(2',4'-dimethoxybiphenyl-4-yl)-N-hydroxy-2-methyl-2-(methylsulfonyl)butanamide | | 32 | 1 | 2 | 2 | na | 0.41[a] |
| 66 | 4-(3'-fluoro-4'-methoxybiphenyl-4-yl)-N-hydroxy-2-methyl-2-(methylsulfonyl)butanamide | | 16 | 1 | 8 | 1 | 99 | 0.44[a] |
| 67 | N-hydroxy-4-(4'-methoxy-3'-methylbiphenyl-4-yl)-2-methyl-2-(methylsulfonyl)butanamide | | ≥64 | 4 | 8 | 16 | 100 | 0.25[a] |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 68 | N-hydroxy-2-methyl-4-{4'-[(methylamino)sulfonyl]biphenyl-4-yl}-2-(methylsulfonyl)butanamide | | ≥64 | 32 | 32 | 4 | 100 | 0.33$^a$ |
| 69 | 4-(2'-ethylbiphenyl-4-yl)-N-hydroxy-2-methyl-2-(methylsulfonyl)butanamide | | ≥64 | 16 | ≥64 | 16 | 100 | 0.5$^a$ |
| 70 | 4-(2',4'-dichlorobiphenyl-4-yl)-N-hydroxy-2-methyl-2-(methylsulfonyl)butanamide | | 32 | 1 | 2 | 1 | 100 | 0.52$^a$ |
| 71 | N-hydroxy-4-[4'-(1-methoxyethyl)biphenyl-4-yl]-2-methyl-2-(methylsulfonyl)butanamide | | 32 | 4 | 16 | 4 | 100 | 0.44$^a$ |
| 72 | N-hydroxy-4-[4-(6-methoxypyridin-3-yl)phenyl]-2-methyl-2-(methylsulfonyl)butanamide | | ≥64 | 8 | 32 | 4 | 100 | 0.35$^a$ |
| 73 | 4-(2',5'-dimethylbiphenyl-4-yl)-N-hydroxy-2-methyl-2-(methylsulfonyl)butanamide | | 4 | 16 | ≥64 | 32 | 100 | 0.5$^a$ |
| 74 | 4-[4-(2,3-dihydro-1-benzofuran-5-yl)phenyl]-N-hydroxy-2-methyl-2-(methylsulfonyl)butanamide | | 16 | 1 | 4 | 1 | 100 | 0.42$^a$ |
| 75 | 4-(3',4'-difluorobiphenyl-4-yl)-N-hydroxy-2-methyl-2-(methylsulfonyl)butanamide | | 8 | 1 | 4 | 0.5 | 100 | 0.46$^a$ |
| 76 | N-hydroxy-4-[4-(2-methoxypyridin-3-yl)phenyl]-2-methyl-2-(methylsulfonyl)butanamide | | ≥64 | 32 | ≥64 | 16 | 100 | 0.38$^a$ |
| 77 | N-hydroxy-2-methyl-2-(methylsulfonyl)-4-[4-(3-thienyl)phenyl]butanamide | 0.000991 | ≥64 | 8 | 16 | 2 | 100 | 0.42$^a$ |
| 78 | 4-(2',3'-dimethylbiphenyl-4-yl)-N-hydroxy-2-methyl-2-(methylsulfonyl)butanamide | 0.000444 | ≥64 | 2 | 16 | 2 | 100 | 0.49$^a$ |
| 79 | N-hydroxy-2-methyl-2-(methylsulfonyl)-4-[4'-(methylsulfonyl)biphenyl-4-yl]butanamide | | ≥64 | 32 | ≥64 | 4 | 100 | 0.33$^a$ |
| 80 | N-hydroxy-2-methyl-2-(methylsulfonyl)-4-(4-pyrimidin-5-ylphenyl)butanamide | | ≥64 | 8 | 32 | 8 | 100 | 0.38$^a$ |
| 81 | 4-(2'-chlorobiphenyl-4-yl)-N-hydroxy-2-methyl-2-(methylsulfonyl)butanamide | 0.000448 | 32 | 2 | 8 | 1 | 100 | 0.46$^a$ |
| 82 | 4-[4-(5-cyano-2-thienyl)phenyl]-N-hydroxy-2-methyl-2-(methylsulfonyl)butanamide | | 8 | 0.5 | 2 | 0.5 | 100 | 0.41$^a$ |
| 83 | 4-(3',4'-dimethylbiphenyl-4-yl)-N-hydroxy-2-methyl-2-(methylsulfonyl)butanamide | 0.000242 | 8 | 1 | 4 | 2 | 100 | 0.5$^a$ |
| 84 | N-hydroxy-4-[3'-(hydroxymethyl)biphenyl-4-yl]-2-methyl-2-(methylsulfonyl)butanamide | | ≥64 | ≥64 | ≥64 | 16 | 94 | 0.34$^a$ |
| 85 | 4'-[4-(hydroxyamino)-3-methyl-3-(methylsulfonyl)-4-oxobutyl]-N-methylbiphenyl-4-carboxamide | | ≥64 | 32 | ≥64 | 16 | 100 | 0.31$^a$ |
| 86 | N-hydroxy-4-[4-(6-methoxy-2-methylpyridin-3-yl)phenyl]-2-methyl-2-(methylsulfonyl)butanamide | | ≥64 | 8 | 32 | 4 | 100 | 0.31$^a$ |
| 87 | N-hydroxy-2-methyl-4-(3'-methylbiphenyl-4-yl)-2-(methylsulfonyl)butanamide | | 8 | 2 | 4 | 1 | 100 | 0.47$^a$ |
| 88 | 4-(3'-chlorobiphenyl-4-yl)-N-hydroxy-2-methyl-2-(methylsulfonyl)butanamide | 0.000364 | 4 | 1 | 4 | 1 | 100 | 0.48$^a$ |
| 89 | 4-(2'-fluoro-3'-methoxybiphenyl-4-yl)-N-hydroxy-2-methyl-2-(methylsulfonyl)butanamide | | 16 | 0.5 | 1 | 0.5 | 100 | 0.42$^a$ |
| 90 | 4-(5'-chloro-2'-fluorobiphenyl-4-yl)-N-hydroxy-2-methyl-2-(methylsulfonyl)butanamide | | 8 | 8 | 8 | 8 | na | na |
| 91 | 4-(4'-cyano-2'-methylbiphenyl-4-yl)-N-hydroxy-2-methyl-2-(methylsulfonyl)butanamide | 0.000266 | 16 | 2 | 8 | 2 | 100 | 0.43$^a$ |
| 92 | N-hydroxy-2-methyl-4-[4'-(1-methyl-1H-imidazol-2-yl)biphenyl-4-yl]-2-(methylsulfonyl)butanamide | | ≥64 | 16 | 32 | 32 | 100 | 0.26$^a$ |
| 93 | 4-[4-(6-cyanopyridin-3-yl)phenyl]-N-hydroxy-2-methyl-2-(methylsulfonyl)butanamide | | ≥64 | 16 | 32 | 4 | 100 | 0.35$^a$ |
| 94 | N-hydroxy-2-methyl-2-(methylsulfonyl)-4-[2'-(methylthio)biphenyl-4-yl]butanamide | | ≥64 | 32 | ≥64 | 32 | 100 | 0.46$^a$ |
| 95 | 4-[4-(3-furyl)phenyl]-N-hydroxy-2-methyl-2-(methylsulfonyl)butanamide | | ≥64 | 16 | 16 | 4 | 100 | 0.38$^a$ |
| 96 | 4'-[4-(hydroxyamino)-3-methyl-3-(methylsulfonyl)-4-oxobutyl]biphenyl-4-carboxamide | | ≥64 | ≥64 | ≥64 | 8 | 100 | 0.28$^a$ |
| 97 | 4-(3',5'-difluorobiphenyl-4-yl)-N-hydroxy-2-methyl-2-(methylsulfonyl)butanamide | | 8 | 2 | 4 | 1 | 100 | 0.46$^a$ |
| 98 | 4-(4'-fluoro-2'-methylbiphenyl-4-yl)-N-hydroxy-2-methyl-2-(methylsulfonyl)butanamide | 0.00123 | 32 | 4 | 16 | 2 | 100 | 0.47$^a$ |
| 99 | N-hydroxy-2-methyl-4-[4-(5-methyl-2-furyl)phenyl]-2-(methylsulfonyl)butanamide | | ≥64 | 16 | 32 | 8 | 100 | 0.38$^a$ |
| 100 | N-hydroxy-4-(2'-methoxybiphenyl-4-yl)-2-methyl-2-(methylsulfonyl)butanamide | | ≥64 | 32 | ≥64 | 8 | 100 | 0.43$^a$ |
| 101 | N-hydroxy-2-methyl-4-[4-(1-methyl-1H-pyrazol-4-yl)phenyl]-2-(methylsulfonyl)butanamide | | ≥64 | 32 | 32 | 8 | 100 | 0.38$^a$ |
| 102 | N-hydroxy-4-(4'-isopropylbiphenyl-4-yl)-2-methyl-2-(methylsulfonyl)butanamide | | 4 | 2 | 8 | 4 | 100 | 0.53$^a$ |
| 103 | 4-[4-(2-furyl)phenyl]-N-hydroxy-2-methyl-2-(methylsulfonyl)butanamide | | 32 | 8 | 16 | 4 | 93 | 0.38$^a$ |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 104 | 4-(3'-chloro-4'-fluorobiphenyl-4-yl)-N-hydroxy-2-methyl-2-(methylsulfonyl)butanamide | 0.000127 | 2 | 0.5 | 2 | 1 | 100 | 0.49[a] |
| 105 | 4-(2'-cyanobiphenyl-4-yl)-N-hydroxy-2-methyl-2-(methylsulfonyl)butanamide | | ≥64 | 8 | 32 | 16 | 100 | 0.4[a] |
| 106 | 4-[4'-(cyanomethyl)biphenyl-4-yl]-N-hydroxy-2-methyl-2-(methylsulfonyl)butanamide | | ≥64 | 2 | 8 | 1 | 100 | 0.37[a] |
| 107 | (2R)-4-(4'-cyanobiphenyl-4-yl)-N-hydroxy-2-methyl-2-(methylsulfonyl)butanamide | 0.000134 | 16 | 0.25 | 1 | 0.25 | na | na |
| 108 | 4-(4'-acetylbiphenyl-4-yl)-N-hydroxy-2-methyl-2-(methylsulfonyl)butanamide | 0.000176 | 32 | 0.5 | 2 | 0.5 | 100 | 0.4[a] |
| 109 | 4-(4'-cyano-3'-methylbiphenyl-4-yl)-N-hydroxy-2-methyl-2-(methylsulfonyl)butanamide | 0.000144 | 32 | 0.5 | 2 | 2 | 100 | 1.47[b] |
| 110 | (2R)-4-(4'-fluorobiphenyl-4-yl)-N-hydroxy-2-methyl-2-(methylsulfonyl)butanamide | | 8 | 2 | 4 | 0.25 | 100 | 0.44[a] |
| 111 | 4-[4'-(aminomethyl)biphenyl-4-yl]-N-hydroxy-2-methyl-2-(methylsulfonyl)butanamide | | ≥64 | ≥64 | ≥64 | 32 | 100 | 0.25[a] |
| 112 | N-hydroxy-4-[4'-(hydroxymethyl)biphenyl-4-yl]-2-methyl-2-(methylsulfonyl)butanamide | | ≥64 | ≥64 | ≥64 | 4 | 57 | 0.32[a] |
| 113 | N-hydroxy-4-[4'-(2-hydroxyethoxy)biphenyl-4-yl]-2-methyl-2-(methylsulfonyl)butanamide | 0.000148 | ≥64 | 2 | 8 | 1 | 100 | 0.33[a] |
| 114 | 4-[4'-(2-aminoethyl)biphenyl-4-yl]-N-hydroxy-2-methyl-2-(methylsulfonyl)butanamide | | ≥64 | ≥64 | ≥64 | 16 | 100 | 0.26[a] |
| 115 | N-hydroxy-4-[4'-(3-hydroxypropoxy)biphenyl-4-yl]-2-methyl-2-(methylsulfonyl)butanamide | 0.000388 | ≥64 | 0.5 | 2 | 2 | 100 | 1.3[b] |
| 116 | 4-[4'-(2-aminoethoxy)biphenyl-4-yl]-N-hydroxy-2-methyl-2-(methylsulfonyl)butanamide | | ≥64 | ≥64 | ≥64 | 4 | 100 | 0.26[a] |
| 117 | 4-[4'-(3-aminopropoxy)biphenyl-4-yl]-N-hydroxy-2-methyl-2-(methylsulfonyl)butanamide | | ≥64 | ≥64 | ≥64 | 8 | 100 | 0.28[a] |
| 118 | 4-[4'-(4-aminobutoxy)biphenyl-4-yl]-N-hydroxy-2-methyl-2-(methylsulfonyl)butanamide | | ≥64 | 32 | ≥64 | 16 | 100 | 0.3[a] |
| 119 | 4-[6-(4-fluorophenyl)pyridin-3-yl]-N-hydroxy-2-methyl-2-(methylsulfonyl)butanamide | | ≥64 | 16 | ≥64 | 8 | 100 | 0.26[a] |
| 120 | N-hydroxy-4-[6-(4-methoxyphenyl)pyridin-3-yl]-2-methyl-2-(methylsulfonyl)butanamide | | ≥64 | 4 | 16 | 8 | 100 | 0.25[a] |
| 121 | N-hydroxy-2-methyl-2-(methylsulfonyl)-4-{6-[4-(methylthio)phenyl]pyridin-3-yl}butanamide | | ≥64 | 1 | 4 | 4 | 100 | 0.29[a] |
| 122 | 4-[6-(4-cyanophenyl)pyridin-3-yl]-N-hydroxy-2-methyl-2-(methylsulfonyl)butanamide | | ≥64 | 16 | ≥64 | 8 | 100 | 0.28[a] |
| 123 | 4-[3'-fluoro-4'-(hydroxymethyl)biphenyl-4-yl]-N-hydroxy-2-methyl-2-(methylsulfonyl)butanamide | 0.000491 | ≥64 | 16 | 16 | 1 | 100 | 1.23[b] |
| 124 | 4-{4-[5-cyano-4-(trifluoromethyl)pyridin-2-yl]phenyl}-N-hydroxy-2-methyl-2-(methylsulfonyl)butanamide | | ≥64 | 8 | ≥64 | 8 | 100 | 0.44[a] |
| 125 | 4-(3',4'-dicyanobiphenyl-4-yl)-N-hydroxy-2-methyl-2-(methylsulfonyl)butanamide | | ≥64 | 8 | 32 | 4 | 97 | 0.4[a] |
| 126 | 4-(3'-chloro-4'-cyanobiphenyl-4-yl)-N-hydroxy-2-methyl-2-(methylsulfonyl)butanamide | 0.000329 | 8 | 0.5 | 2 | 0.5 | 0 | na |
| 127 | 4-(4'-cyano-3',5'-difluorobiphenyl-4-yl)-N-hydroxy-2-methyl-2-(methylsulfonyl)butanamide | 0.00015 | 32 | 1 | 8 | 2 | 100 | 1.49[b] |
| 128 | 4-(4'-cyano-2'-fluorobiphenyl-4-yl)-N-hydroxy-2-methyl-2-(methylsulfonyl)butanamide | 0.000232 | ≥64 | 0.5 | 8 | 0.5 | 100 | 0.42[a] |
| 129 | 4-[4-(5-cyanopyridin-2-yl)phenyl]-N-hydroxy-2-methyl-2-(methylsulfonyl)butanamide | | ≥64 | 16 | ≥64 | 4 | 100 | 0.35[a] |
| 130 | 4-[4-(5-cyanopyrazin-2-yl)phenyl]-N-hydroxy-2-methyl-2-(methylsulfonyl)butanamide | | ≥64 | 16 | ≥64 | 16 | 100 | 0.35[a] |
| 131 | 4-[4-(5-cyano-6-methylpyridin-2-yl)phenyl]-N-hydroxy-2-methyl-2-(methylsulfonyl)butanamide | | ≥64 | 4 | 16 | 4 | 100 | 0.39[a] |
| 132 | 4-[4-(benzyloxy)phenyl]-N-hydroxy-2-methyl-2-(methylsulfonyl)butanamide | 0.000386 | 16 | 2 | 16 | 2 | 100 | 0.49[a] |
| 133 | 4-[6-(4-acetylphenyl)pyridin-3-yl]-N-hydroxy-2-methyl-2-(methylsulfonyl)butanamide | 0.000985 | ≥64 | 16 | ≥64 | 16 | 100 | 0.28[a] |
| 134 | 4-[6-(2-fluoro-3-methoxyphenyl)pyridin-3-yl]-N-hydroxy-2-methyl-2-(methylsulfonyl)butanamide | | ≥64 | 4 | 16 | 4 | 100 | 0.27[a] |
| 135 | N-hydroxy-4-(4-methoxyphenyl)-2-methyl-2-(methylsulfonyl)butanamide | | ≥64 | ≥64 | ≥64 | 32 | 100 | 0.31[a] |
| 136 | N-hydroxy-4-[4'-(4-hydroxybutoxy)biphenyl-4-yl]-2-methyl-2-(methylsulfonyl)butanamide | 0.000205 | ≥64 | 0.125 | 1 | 1 | 100 | 0.38[a] |
| 137 | N-hydroxy-4-(4'-hydroxy-3'-methylbiphenyl-4-yl)-2-methyl-2-(methylsulfonyl)butanamide | | ≥64 | 16 | 32 | 4 | 100 | 1.23[b] |
| 138 | 4-(3'-fluoro-4'-hydroxybiphenyl-4-yl)-N-hydroxy-2-methyl-2-(methylsulfonyl)butanamide | 0.000335 | 32 | 2 | 8 | 1 | 100 | 0.34[a] |
| 139 | N-hydroxy-4-(4'-hydroxy-3'-methoxybiphenyl-4-yl)-2-methyl-2-(methylsulfonyl)butanamide | | ≥64 | 16 | ≥64 | 16 | 100 | 1.12[b] |
| 140 | N-hydroxy-4-(4'-hydroxy-2'-methylbiphenyl-4-yl)-2-methyl-2-(methylsulfonyl)butanamide | | ≥64 | 32 | ≥64 | 4 | 100 | 1.17[b] |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 141 | N-hydroxy-4-(4'-hydroxy-2'-methoxybiphenyl-4-yl)-2-methyl-2-(methylsulfonyl)butanamide | | ≥64 | ≥64 | ≥64 | 32 | 100 | 0.33$^a$ |
| 142 | 4-(4'-cyano-3'-hydroxybiphenyl-4-yl)-N-hydroxy-2-methyl-2-(methylsulfonyl)butanamide | | ≥64 | ≥64 | ≥64 | 32 | 100 | 0.35$^a$ |
| 143 | N-hydroxy-4-[6-(2-hydroxyphenyl)pyridin-3-yl]-2-methyl-2-(methylsulfonyl)butanamide | | ≥64 | 4 | 32 | 4 | na | na |
| 144 | 4-[2'-fluoro-4'-(2-hydroxyethoxy)biphenyl-4-yl]-N-hydroxy-2-methyl-2-(methylsulfonyl)butanamide | | ≥64 | 1 | 4 | 1 | 100 | 0.35$^a$ |
| 145 | 4-[3'-fluoro-4'-(2-hydroxyethoxy)biphenyl-4-yl]-N-hydroxy-2-methyl-2-(methylsulfonyl)butanamide | | ≥64 | 2 | 4 | 1 | 100 | 0.35$^a$ |
| 146 | N-hydroxy-4-[4'-(2-hydroxy-2-methylpropyl)biphenyl-4-yl]-2-methyl-2-(methylsulfonyl)butanamide | | ≥64 | 8 | 32 | 8 | 100 | 0.41$^a$ |
| 147 | 4-[2',3'-difluoro-4'-(2-hydroxyethoxy)biphenyl-4-yl]-N-hydroxy-2-methyl-2-(methylsulfonyl)butanamide | | 32 | 2 | 8 | 1 | 100 | 0.37$^a$ |
| 148 | 4-[3'-cyano-4'-(2-hydroxyethoxy)biphenyl-4-yl]-N-hydroxy-2-methyl-2-(methylsulfonyl)butanamide | | ≥64 | 16 | ≥64 | 16 | 100 | 0.35$^a$ |
| 149 | 4-(2'-fluoro-4'-hydroxybiphenyl-4-yl)-N-hydroxy-2-methyl-2-(methylsulfonyl)butanamide | | ≥64 | 2 | 8 | 1 | 100 | 0.36$^a$ |
| 150 | 4-[3',5'-difluoro-4'-(2-hydroxyethoxy)biphenyl-4-yl]-N-hydroxy-2-methyl-2-(methylsulfonyl)butanamide | | 32 | 2 | 8 | 2 | 99 | 0.38$^a$ |
| 151 | N-hydroxy-4-[4'-(2-hydroxyethoxy)-2'-methylbiphenyl-4-yl]-2-methyl-2-(methylsulfonyl)butanamide | | ≥64 | 8 | 32 | 4 | 99 | 0.37$^a$ |
| 152 | N-hydroxy-4-[4'-(2-hydroxyethyl)-3'-methylbiphenyl-4-yl]-2-methyl-2-(methylsulfonyl)butanamide | | ≥64 | 4 | 16 | 2 | 99 | 0.38$^a$ |
| 153 | N-hydroxy-4-[2'-(1-hydroxy-1-methylethyl)biphenyl-4-yl]-2-methyl-2-(methylsulfonyl)butanamide | | ≥64 | ≥64 | ≥64 | 32 | 99 | 0.4$^a$ |
| 154 | 4-(2'-fluoro-3'-hydroxybiphenyl-4-yl)-N-hydroxy-2-methyl-2-(methylsulfonyl)butanamide | | ≥64 | 4 | 8 | 1 | 99 | 0.37$^a$ |
| 155 | 4-[2'-fluoro-4'-(2-hydroxyethyl)biphenyl-4-yl]-N-hydroxy-2-methyl-2-(methylsulfonyl)butanamide | | ≥64 | 2 | 8 | 1 | 99 | 0.37$^a$ |
| 156 | N-hydroxy-4-[4'-(2-hydroxyethyl)-2'-methylbiphenyl-4-yl]-2-methyl-2-(methylsulfonyl)butanamide | | 16 | 16 | 8 | 8 | 100 | 0.38$^a$ |
| 157 | 4-(4'-fluoro-3-methylbiphenyl-4-yl)-N-hydroxy-2-methyl-2-(methylsulfonyl)butanamide | 0.000337 | 8 | 1 | 4 | 4 | 100 | 0.48$^a$ |
| 158 | N-hydroxy-4-[4'-(3-hydroxy-3-methylbutyl)biphenyl-4-yl]-2-methyl-2-(methylsulfonyl)butanamide | 0.000644 | 32 | 0.5 | 8 | 4 | 100 | 0.43$^a$ |
| 159 | N-hydroxy-2-methyl-4-(2-methylbiphenyl-4-yl)-2-(methylsulfonyl)butanamide | 0.00558 | 32 | 4 | 16 | 8 | 100 | 0.47$^a$ |
| 160 | 4-(4'-fluoro-2-methylbiphenyl-4-yl)-N-hydroxy-2-methyl-2-(methylsulfonyl)butanamide | 0.00254 | 16 | 2 | 8 | 4 | 100 | 0.48$^a$ |
| 161 | 4-(4'-cyano-3-methylbiphenyl-4-yl)-N-hydroxy-2-methyl-2-(methylsulfonyl)butanamide | 0.000725 | ≥64 | 1 | 16 | 4 | 100 | 0.42$^a$ |
| 162 | 4-(4'-cyano-2-methylbiphenyl-4-yl)-N-hydroxy-2-methyl-2-(methylsulfonyl)butanamide | 0.000241 | 16 | 2 | 16 | 4 | 100 | 0.43$^a$ |
| 163 | 4-[5-(4-cyanophenyl)pyridin-2-yl]-N-hydroxy-2-methyl-2-(methylsulfonyl)butanamide | | ≥64 | 32 | 32 | 8 | na | na |
| 164 | 4-[5-(4-fluorophenyl)pyridin-2-yl]-N-hydroxy-2-methyl-2-(methylsulfonyl)butanamide | | ≥64 | 32 | 32 | 4 | na | na |
| 165 | N-hydroxy-2-methyl-2-(methylsulfonyl)-4-(4'-morpholin-4-ylbiphenyl-4-yl)butanamide | 0.000295 | ≥64 | 0.5 | 8 | 8 | 100 | 0.37$^a$ |
| 166 | N-hydroxy-2-methyl-4-[4'-(4-methylpiperazin-1-yl)biphenyl-4-yl]-2-(methylsulfonyl)butanamide | 0.00117 | ≥64 | 4 | 16 | 2 | 100 | 0.28$^a$ |
| 167 | 4-(2,4'-difluorobiphenyl-4-yl)-N-hydroxy-2-methyl-2-(methylsulfonyl)butanamide | 0.000235 | 8 | 1 | 4 | 0.5 | 100 | 0.46$^a$ |
| 168 | 4-(4'-cyano-3-fluorobiphenyl-4-yl)-N-hydroxy-2-methyl-2-(methylsulfonyl)butanamide | 0.000427 | ≥64 | 1 | 2 | 1 | 100 | 0.41$^a$ |
| 169 | 4-(4'-glycoloylbiphenyl-4-yl)-N-hydroxy-2-methyl-2-(methylsulfonyl)butanamide | 0.0002 | 32 | 2 | 4 | 1 | 100 | 0.33$^a$ |
| 170 | (2R)-N-hydroxy-4-(3'-methoxybiphenyl-4-yl)-2-methyl-2-(methylsulfonyl)butanamide | 0.054 | 16 | ≥64 | ≥64 | ≥64 | 100 | 0.44$^a$ |
| 171 | N-hydroxy-4-(2-methoxybiphenyl-4-yl)-2-methyl-2-(methylsulfonyl)butanamide | 0.0146 | ≥64 | 4 | 16 | 32 | 100 | 0.45$^a$ |
| 172 | (2R)-N-hydroxy-2-methyl-2-(methylsulfonyl)-4-[4'-(2-morpholin-4-ylethoxy)biphenyl-4-yl]butanamide | 0.000512 | ≥64 | 0.5 | 4 | 4 | 100 | 0.29$^a$ |
| 173 | 4-[4-(2,3-dihydro-1H-isoindol-5-yl)phenyl]-N-hydroxy-2-methyl-2-(methylsulfonyl)butanamide | 0.00268 | ≥64 | ≥64 | ≥64 | 16 | 100 | 0.25$^a$ |
| 174 | 4-[4-(2,1,3-benzoxadiazol-5-yl)phenyl]-N-hydroxy-2-methyl-2-(methylsulfonyl)butanamide | 0.00054 | ≥64 | 4 | 8 | 2 | 100 | 0.43$^a$ |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 175 | (2S)-4-[4-(2,3-dihydro-1,4-benzodioxin-6-yl)phenyl]-N-hydroxy-2-methyl-2-(methylsulfonyl)butanamide | 0.0146 | ≥64 | 32 | ≥64 | ≥64 | 100 | 0.43[a] |
| 176 | 4-[4-(1,3-benzodioxol-5-yl)phenyl]-N-hydroxy-2-methyl-2-(methylsulfonyl)butanamide | 3.03E-05 | 16 | 0.5 | 2 | 0.5 | 100 | 0.43[a] |
| 177 | 4-(2-fluoro-4'-hydroxybiphenyl-4-yl)-N-hydroxy-2-methyl-2-(methylsulfonyl)butanamide | 0.000306 | 32 | 1 | 8 | 2 | 100 | 0.34[a] |
| 178 | 4-(3-fluoro-4'-hydroxybiphenyl-4-yl)-N-hydroxy-2-methyl-2-(methylsulfonyl)butanamide | 5.92E-05 | 8 | 1 | 4 | 1 | 100 | 0.35[a] |
| 179 | (2R)-N-hydroxy-2-methyl-2-(methylsulfonyl)-4-[4'-(3-morpholin-4-ylpropoxy)biphenyl-4-yl]butanamide | 0.000172 | 2 | 0.125 | 2 | 2 | 100 | 0.3[a] |
| 180 | 4-(3'-acetyl-4'-hydroxybiphenyl-4-yl)-N-hydroxy-2-methyl-2-(methylsulfonyl)butanamide | 0.000826 | 16 | 4 | 16 | 8 | 100 | 0.43[a] |
| 181 | 4-(4'-acetyl-3'-hydroxybiphenyl-4-yl)-N-hydroxy-2-methyl-2-(methylsulfonyl)butanamide | 0.000138 | 8 | 0.5 | 8 | 2 | 100 | 0.42[a] |
| 182 | (2R)-4-(4'-acetylbiphenyl-4-yl)-N-hydroxy-2-methyl-2-(methylsulfonyl)butanamide | 6.74E-05 | 16 | 0.5 | 1 | 0.5 | 95 | 1.43[b] |
| 183 | 4-(3-fluoro-4'-glycoloylbiphenyl-4-yl)-N-hydroxy-2-methyl-2-(methylsulfonyl)butanamide | 0.000387 | ≥64 | 2 | 4 | 2 | 100 | 0.33[a] |
| 184 | 4-(4'-acetyl-3'-fluorobiphenyl-4-yl)-N-hydroxy-2-methyl-2-(methylsulfonyl)butanamide | 0.000155 | 32 | 4 | 2 | 0.5 | 100 | 0.43[a] |
| 185 | N-hydroxy-2-methyl-2-(methylsulfonyl)-4-(4'-piperazin-1-ylbiphenyl-4-yl)butanamide | 0.00622 | ≥64 | 16 | ≥64 | 8 | 100 | 0.28[a] |
| 186 | (2R)-4-(4'-glycoloylbiphenyl-4-yl)-N-hydroxy-2-methyl-2-(methylsulfonyl)butanamide | 0.000238 | ≥64 | 2 | 4 | 1 | 100 | 0.33[a] |
| 187 | 4-[4-(5-acetylpyridin-2-yl)-2-fluorophenyl]-N-hydroxy-2-methyl-2-(methylsulfonyl)butanamide | 0.000632 | ≥64 | 16 | 16 | 4 | 100 | 0.36[a] |
| 188 | 4-[4-(6-acetylpyridin-3-yl)-2-fluorophenyl]-N-hydroxy-2-methyl-2-(methylsulfonyl)butanamide | 0.000348 | ≥64 | 8 | 8 | 2 | 100 | 0.36[a] |
| 189 | (2R)-4-[4-(5-acetylpyridin-2-yl)phenyl]-N-hydroxy-2-methyl-2-(methylsulfonyl)butanamide | 0.000711 | ≥64 | 16 | 16 | 4 | 100 | 0.31[a] |
| 190 | (2R)-4-[4-(6-acetylpyridin-3-yl)phenyl]-N-hydroxy-2-methyl-2-(methylsulfonyl)butanamide | 0.000246 | ≥64 | 4 | 4 | 2 | 100 | 0.35[a] |
| 191 | (2R)-N-hydroxy-4-{4'-[2-(4-hydroxypiperidin-1-yl)-2-oxoethyl]biphenyl-4-yl}-2-methyl-2-(methylsulfonyl)butanamide | 0.00263 | ≥64 | ≥64 | ≥64 | 16 | 100 | 0.32[a] |
| 192 | (2R)-N-hydroxy-4-{4'-[(4-hydroxypiperidin-1-yl)carbonyl]biphenyl-4-yl}-2-methyl-2-(methylsulfonyl)butanamide | 0.00339 | ≥64 | ≥64 | ≥64 | 16 | 100 | 0.31[a] |
| 193 | N-hydroxy-2-methyl-2-(methylsulfonyl)-4-{4'-[4-(methylsulfonyl)piperazin-1-yl]biphenyl-4-yl}butanamide | 0.00108 | ≥64 | 16 | ≥64 | ≥64 | 100 | 0.38[a] |
| 194 | (2R)-N-hydroxy-4-(4'-lactoylbiphenyl-4-yl)-2-methyl-2-(methylsulfonyl)butanamide | 0.000195 | ≥64 | 1 | 4 | 1 | 100 | 0.35[a] |
| 195 | 4-(3-fluoro-4-quinolin-6-ylphenyl)-N-hydroxy-2-methyl-2-(methylsulfonyl)butanamide | 0.000733 | 32 | 1 | 4 | 2 | 83 | 0.29[a] |
| 196 | 4-[2-fluoro-4-(3-oxo-2,3-dihydro-1H-isoindol-5-yl)phenyl]-N-hydroxy-2-methyl-2-(methylsulfonyl)butanamide | 0.000631 | ≥64 | 4 | 16 | 4 | 100 | 0.33[a] |
| 197 | 4-(3-fluoro-4-pyridin-3-ylphenyl)-N-hydroxy-2-methyl-2-(methylsulfonyl)butanamide | 0.00711 | ≥64 | ≥64 | ≥64 | 8 | 100 | 0.24[a] |
| 198 | (2R)-N-hydroxy-2-methyl-2-(methylsulfonyl)-4-(4-pyridin-3-ylphenyl)butanamide | 0.00384 | ≥64 | ≥64 | ≥64 | 8 | 100 | 0.23[a] |
| 199 | (2R)-N-hydroxy-2-methyl-2-(methylsulfonyl)-4-[4-(1-oxo-2,3-dihydro-1H-isoindol-5-yl)phenyl]butanamide | 0.000266 | ≥64 | 8 | 32 | 2 | 100 | 0.31[a] |
| 200 | 4-(2-fluoro-4-quinolin-3-ylphenyl)-N-hydroxy-2-methyl-2-(methylsulfonyl)butanamide | 0.000463 | ≥64 | 1 | 8 | 4 | 100 | 0.33[a] |
| 201 | (2R)-N-hydroxy-2-methyl-2-(methylsulfonyl)-4-(4-quinolin-3-ylphenyl)butanamide | 0.00024 | ≥64 | 1 | 8 | 2 | 100 | 0.31[a] |
| 202 | (2R)-4-[4-(5-cyanopyridin-2-yl)phenyl]-N-hydroxy-2-methyl-2-(methylsulfonyl)butanamide | 0.000808 | ≥64 | 8 | 16 | 1 | 100 | 0.37[a] |
| 203 | 4-[3-fluoro-4-(3-oxo-2,3-dihydro-1H-isoindol-5-yl)phenyl]-N-hydroxy-2-methyl-2-(methylsulfonyl)butanamide | 0.000659 | ≥64 | 8 | 32 | 4 | 100 | 0.32[a] |
| 204 | (2R)-4-[4-(6-aminopyridin-3-yl)phenyl]-N-hydroxy-2-methyl-2-(methylsulfonyl)butanamide | 0.0182 | ≥64 | ≥64 | ≥64 | 8 | 100 | 0.24[a] |
| 205 | (2R)-4-(4'-acetamidobiphenyl-4-yl)-N-hydroxy-2-methyl-2-(methylsulfonyl)butanamide | 0.00174 | ≥64 | 16 | 32 | 4 | 100 | 0.35[a] |
| 206 | 4-[4-(6-aminopyridin-3-yl)-3-fluorophenyl]-N-hydroxy-2-methyl-2-(methylsulfonyl)butanamide | 0.0235 | ≥64 | ≥64 | ≥64 | 16 | 100 | 0.25[a] |
| 207 | 4-(4'-acetamido-2-fluorobiphenyl-4-yl)-N-hydroxy-2-methyl-2-(methylsulfonyl)butanamide | 0.00709 | ≥64 | 32 | ≥64 | 16 | 100 | 0.36[a] |

TABLE 2-continued

| Example Number | IUPACNAME | PA LpxC enzyeme IC50 uM | AB-3167 MIC | EC-1 MIC | KP-3700 MIC | PA-7 MIC | LCMS ELSD | LCMS-RT |
|---|---|---|---|---|---|---|---|---|
| 208 | (2R)-N-hydroxy-2-methyl-2-(methylsulfonyl)-4-[4-(3-oxo-2,3-dihydro-1H-isoindol-5-yl)phenyl]butanamide | 0.000374 | ≥64 | 4 | 16 | 2 | 100 | 0.31$^a$ |
| 209 | 4-{2-fluoro-4'-[(methylsulfonyl)amino]biphenyl-4-yl}-N-hydroxy-2-methyl-2-(methylsulfonyl)butanamide | 0.00204 | ≥64 | 8 | 32 | 8 | 100 | 0.37$^a$ |
| 210 | (2R)-N-hydroxy-2-methyl-2-(methylsulfonyl)-4-{4'-[(methylsulfonyl)amino]biphenyl-4-yl}butanamide | 0.000706 | ≥64 | 4 | 16 | 2 | 100 | 0.36$^a$ |
| 211 | (2R)-N-hydroxy-2-methyl-2-(methylsulfonyl)-4-[4-(1H-pyrrolo[3,2-b]pyridin-6-yl)phenyl]butanamide | 0.0111 | ≥64 | ≥64 | ≥64 | 32 | 71 | 0.26$^a$ |
| 212 | (2R)-N-hydroxy-4-[4-(6-methoxypyridin-3-yl)phenyl]-2-methyl-2-(methylsulfonyl)butanamide | 0.000237 | ≥64 | 4 | 16 | 1 | 100 | 0.38$^a$ |
| 213 | 4-[3-fluoro-4-(6-methoxypyridin-3-yl)phenyl]-N-hydroxy-2-methyl-2-(methylsulfonyl)butanamide | 0.000518 | ≥64 | 2 | 8 | 2 | 100 | 0.41$^a$ |
| 214 | (2R)-4-[4-(1-benzofuran-2-yl)phenyl]-N-hydroxy-2-methyl-2-(methylsulfonyl)butanamide | | 8 | 0.125 | 4 | 8 | na | na |
| 215 | (2R)-4-[4-(1,3-benzodioxol-5-yl)phenyl]-N-hydroxy-2-methyl-2-(methylsulfonyl)butanamide | 8.42E−05 | 16 | 0.5 | 2 | 0.5 | 100 | 0.43$^a$ |
| 216 | (2R)-N-hydroxy-4-(4'-{[(2R)-2-(hydroxymethyl)pyrrolidin-1-yl]carbonyl}biphenyl-4-yl)-2-methyl-2-(methylsulfonyl)butanamide | 0.00402 | ≥64 | 32 | ≥64 | 32 | 100 | 0.33$^a$ |
| 217 | (2R)-N-hydroxy-4-[4'-(2-hydroxy-2-methylpropanoyl)biphenyl-4-yl]-2-methyl-2-(methylsulfonyl)butanamide | 0.000278 | ≥64 | 0.5 | 4 | 4 | 100 | 0.41$^a$ |
| 218 | (2R)-N-hydroxy-4-[4-(1H-indol-2-yl)phenyl]-2-methyl-2-(methylsulfonyl)butanamide | 0.000034 | 32 | 0.5 | 2 | 0.5 | 100 | 0.47$^a$ |
| 219 | 4-[6-(2-fluoro-4-methoxyphenyl)pyridin-3-yl]-N-hydroxy-2-methyl-2-(methylsulfonyl)butanamide | 0.00121 | ≥64 | 4 | 16 | 8 | 100 | 0.29$^a$ |
| 220 | (2R)-N-hydroxy-2-methyl-2-(methylsulfonyl)-4-[4'-(3-piperidin-1-ylpropoxy)biphenyl-4-yl]butanamide | 0.000467 | ≥64 | 8 | 32 | 16 | 100 | 0.35$^a$ |
| 221 | (2R)-N-hydroxy-4-{4'-[2-(4-hydroxypiperidin-1-yl)-2-oxoethoxy]biphenyl-4-yl}-2-methyl-2-(methylsulfonyl)butanamide | 0.000533 | ≥64 | 16 | ≥64 | 16 | 100 | 0.35$^a$ |
| 222 | (2R)-N-hydroxy-4-{4'-[2-(4-hydroxy-4-methylpiperidin-1-yl)-2-oxoethoxy]biphenyl-4-yl}-2-methyl-2-(methylsulfonyl)butanamide | 0.000841 | ≥64 | 16 | ≥64 | 32 | 98 | 0.37$^a$ |
| 223 | (2R)-N-hydroxy-4-{4'-[2-(3-hydroxyazetidin-1-yl)-2-oxoethoxy]biphenyl-4-yl}-2-methyl-2-(methylsulfonyl)butanamide | 0.000507 | ≥64 | 16 | 32 | 8 | 100 | 0.34$^a$ |
| 224 | 4-(4-cyclohex-1-en-1-ylphenyl)-N-hydroxy-2-methyl-2-(methylsulfonyl)butanamide | 0.000441 | 4 | 4 | 16 | 2 | 100 | 0.5$^a$ |
| 225 | 4-[4-(3,6-dihydro-2H-pyran-4-yl)phenyl]-N-hydroxy-2-methyl-2-(methylsulfonyl)butanamide | 0.00188 | ≥64 | 32 | ≥64 | 4 | 100 | 0.45$^a$ |
| 226 | 4-[4-(3,6-dihydro-2H-thiopyran-4-yl)phenyl]-N-hydroxy-2-methyl-2-(methylsulfonyl)butanamide | 0.00032 | 16 | 8 | 8 | 1 | na | na |
| 227 | 4-(4-cyclopent-1-en-1-ylphenyl)-N-hydroxy-2-methyl-2-(methylsulfonyl)butanamide | 0.0114 | ≥64 | ≥64 | ≥64 | 16 | na | 0.54$^a$ |
| 228 | 4-{4-[(4-fluorophenoxy)methyl]phenyl}-N-hydroxy-2-methyl-2-(methylsulfonyl)butanamide | 0.00328 | 16 | 8 | 16 | 8 | 100 | 1.51$^b$ |
| 229 | 4-{4-[(3-fluorophenoxy)methyl]phenyl}-N-hydroxy-2-methyl-2-(methylsulfonyl)butanamide | 0.00324 | 16 | 8 | 32 | 8 | 100 | 0.46$^a$ |
| 230 | N-hydroxy-4-[4'-(1-hydroxy-1-methylethyl)biphenyl-4-yl]-2-methyl-2-(methylsulfonyl)butanamide | | ≥64 | 8 | 32 | 8 | 100 | 0.38$^a$ |
| 231 | (2S)-2-amino-3-{4'-[4-(hydroxyamino)-3-methyl-3-(methylsulfonyl)-4-oxobutyl]biphenyl-4-yl}propanoic acid | | ≥64 | 32 | ≥64 | 16 | 89 | 0.25$^a$ |
| 232 | (2R)-2-amino-3-{4'-[4-(hydroxyamino)-3-methyl-3-(methylsulfonyl)-4-oxobutyl]biphenyl-4-yl}propanoic acid | | ≥64 | ≥64 | ≥64 | 32 | 96 | 0.25$^a$ |

Examples 233-318

In addition to the compounds above, a series of ether derivatives (i.e. L is O) were also prepared by combinatorial methods. Table 3 below lists these compounds by name, provides characterization data such as liquid chromatography-mass spectrometry and retention times. Table 3 also provides selected biological data using the same protocols as described above for Examples 1-25.

The compounds described below in Table 3 form a subset of those described by Formula I. In all of these compounds $R^1$ and $R^2$ are methyl, X is $CH_2$, A is unsubstituted phenyl, L is O, D is as described above and G and T may be absent or present and are as defined above.

These compounds were generally produced in the following manner.

Step 1:

Phenol monomer ((+/−)-Ethyl 4-(4-hydroxyphenyl)-2-methyl-2-(methylsulfonyl)butanoate) (600 ul, 125 umol) of a 0.208M solution in anhydrous DMA was dispensed into 8 mL vials. To this was added Cs$_2$CO$_3$ (81 mg, 250 umol, 2 eq). The vials were capped and shaken at 30° C. for 30 mins. An appropriate alkyl/benzyl halide, i.e. one corresponding to the desired G-T-D moiety, (162 umol, 1.3 eq) was added to the vials. The vials were capped and shaken at 30° C. for 16 hours. The reaction mixture was filtered and concentrated by Speedvac to give the crude intermediate.

Step 2:

THF (300 ul) and MeOH (600 ul) were added to each vial followed by manual addition of a freshly prepared 1M solution of LiOH in water (300 ul, 3 umol, 3 eq.). The vials were capped and shaken at 30° C. for 16 hours. THF and MeOH were removed via speedvac and the resulting contents were adjusted to pH 3-5 by the addition of a prepared solution of citric acid in water (50 ul of a 12 g citric acid in 15 mL H$_2$O). The mixture was extracted with DCM 8 mL, dried over MgSO$_4$ and concentrated by speedvac to give crude intermediate.

Step 3:

Anhydrous DCM 2 mL was added to each vial containing crude acid (approx. 75 umol, 1 eq). Oxalyl chloride (23 ul, 275 umol, 3.6 eq) and 5 ul DMF was added to the vials. Nitrogen was bubbled for 1 minute to deoxygenate the reaction mixtures. The vials were capped and allowed to shake at 30° C. for 60 mins. O-TMS-hydroxylamine (91 ul, 750 umol-10 eq) was added to the vials. The vials were left to shake for a further 2 hrs at 30° C. The solvent was removed by speedvac and the residue was purified by prep HPLC to give the final product. A few of the compounds below in Table 3 were produced individually, not by combinatorial methods, but the teachings above could be used to generate the compound. In Table 3 below, column 2 provides the IUPAC name, column's 3-7 provide in-vitro biological data generated in the same manner as in Table I, columns 8 and 9 provide the retention times and mass spectra generated via LCMS, using the same methodology as described in Table 2, except that the acidic gradient was used to generate all retention times. Some data is not available, as described in Table 2, and is labeled "na".

TABLE 3

| Example | IUPAC NAME | PA LpxC enzyeme IC$^{50}$ μM | AB-3167 MIC | EC-1 MIC | KP-3700 MIC | PA-7 MIC | Ret. time | LCMS ELSD |
|---|---|---|---|---|---|---|---|---|
| 233 | 4-{4-[(4-cyanobenzyl)oxy]phenyl}-N-hydroxy-2-methyl-2-(methylsulfonyl)butanamide | | ≥64 | 4 | 16 | 4 | | 100 |
| 234 | N-hydroxy-4-(4-isopropoxyphenyl)-2-methyl-2-(methylsulfonyl)butanamide | | ≥64 | ≥64 | ≥64 | 8 | 0.38 | 100 |
| 235 | 4-(4-ethoxyphenyl)-N-hydroxy-2-methyl-2-(methylsulfonyl)butanamide | | ≥64 | 32 | ≥64 | 16 | 0.35 | 100 |
| 236 | 4-(4-butoxyphenyl)-N-hydroxy-2-methyl-2-(methylsulfonyl)butanamide | | 32 | 16 | ≥64 | 8 | 0.44 | 100 |
| 237 | N-hydroxy-2-methyl-2-(methylsulfonyl)-4-(4-propoxyphenyl)butanamide | | ≥64 | 32 | ≥64 | 8 | 0.4 | 100 |
| 238 | 4-[4-(cyclohexyloxy)phenyl]-N-hydroxy-2-methyl-2-(methylsulfonyl)butanamide | 0.000753 | 32 | 32 | ≥64 | 8 | 0.48 | 100 |
| 239 | 4-[4-(2-ethylbutoxy)phenyl]-N-hydroxy-2-methyl-2-(methylsulfonyl)butanamide | 0.00129 | 4 | 16 | ≥64 | 8 | 0.58 | 100 |
| 240 | N-hydroxy-2-methyl-2-(methylsulfonyl)-4-(4-{[3-(1-phenylpropyl)-1,2,4-oxadiazol-5-yl]methoxy}phenyl)butanamide | 0.0205 | ≥64 | 32 | ≥64 | ≥64 | 0.55 | 100 |
| 241 | 4-(4-{[3-(3-fluorophenyl)-1,2,4-oxadiazol-5-yl]methoxy}phenyl)-N-hydroxy-2-methyl-2-(methylsulfonyl)butanamide | 0.00381 | 16 | 8 | ≥64 | 32 | 0.5 | 100 |
| 242 | 4-{4-[(2-fluorobenzyl)oxy]phenyl}-N-hydroxy-2-methyl-2-(methylsulfonyl)butanamide | 0.000655 | ≥64 | 4 | 8 | ≥64 | 0.5 | 100 |
| 243 | 4-{4-[3-(benzyloxy)propoxy]phenyl}-N-hydroxy-2-methyl-2-(methylsulfonyl)butanamide | 0.0211 | 32 | 32 | ≥64 | ≥64 | 0.53 | 100 |
| 244 | 4-{4-[(3,5-dimethoxybenzyl)oxy]phenyl}-N-hydroxy-2-methyl-2-(methylsulfonyl)butanamide | 0.005 | ≥64 | 4 | 16 | ≥64 | 0.48 | 100 |
| 245 | N-hydroxy-2-methyl-4-{4-[(2-methylpyridin-3-yl)methoxy]phenyl}-2-(methylsulfonyl)butanamide | 0.00559 | ≥64 | ≥64 | ≥64 | 32 | 0.38 | 100 |
| 246 | 4-[4-(cyclopropylmethoxy)phenyl]- | 0.0105 | ≥64 | 32 | ≥64 | ≥64 | 0.47 | 100 |

TABLE 3-continued

| Example | IUPAC NAME | PA LpxC enzyeme IC$^{50}$ μM | AB-3167 MIC | EC-1 MIC | KP-3700 MIC | PA-7 MIC | Ret. time | LCMS ELSD |
|---|---|---|---|---|---|---|---|---|
| 247 | 4-{4-[(2,3-difluorobenzyl)oxy]phenyl}-N-hydroxy-2-methyl-2-(methylsulfonyl)butanamide | 0.000325 | 16 | 2 | 16 | 2 | 0.52 | 100 |
| 248 | N-hydroxy-2-methyl-2-(methylsulfonyl)-4-[4-(2-phenoxyethoxy)phenyl]butanamide | 0.00152 | 32 | 2 | 8 | 32 | 0.49 | 100 |
| 249 | 4-(4-{[4-fluoro-2-(trifluoromethyl)benzyl]oxy}phenyl)-N-hydroxy-2-methyl-2-(methylsulfonyl)butanamide | 0.00236 | 16 | 16 | ≥64 | 16 | 0.54 | 100 |
| 250 | 4-{4-[(3-chlorobenzyl)oxy]phenyl}-N-hydroxy-2-methyl-2-(methylsulfonyl)butanamide | 0.00132 | 4 | 2 | 8 | 4 | 0.52 | 100 |
| 251 | 4-(4-{[2-(2-fluorophenyl)-5-methyl-1,3-oxazol-4-yl]methoxy}phenyl)-N-hydroxy-2-methyl-2-(methylsulfonyl)butanamide | 0.0216 | ≥64 | 32 | ≥64 | ≥64 | 0.52 | 100 |
| 252 | 4-[4-(hexyloxy)phenyl]-N-hydroxy-2-methyl-2-(methylsulfonyl)butanamide | 0.00631 | 4 | 8 | 32 | 16 | 0.58 | 100 |
| 253 | 4-(4-{[3-(2,3-difluorophenyl)-1,2,4-oxadiazol-5-yl]methoxy}phenyl)-N-hydroxy-2-methyl-2-(methylsulfonyl)butanamide | 0.00531 | ≥64 | 8 | ≥64 | 32 | 0.51 | 100 |
| 254 | 4-{4-[(2,5-dimethylbenzyl)oxy]phenyl}-N-hydroxy-2-methyl-2-(methylsulfonyl)butanamide | 0.00425 | 16 | 8 | ≥64 | 16 | 0.56 | 100 |
| 255 | 4-(4-{[3-(3,5-difluorophenyl)-1,2,4-oxadiazol-5-yl]methoxy}phenyl)-N-hydroxy-2-methyl-2-(methylsulfonyl)butanamide | 0.00581 | 16 | 16 | ≥64 | ≥64 | 0.52 | 100 |
| 256 | 4-(4-{[3-(2,5-difluorobenzyl)-1,2,4-oxadiazol-5-yl]methoxy}phenyl)-N-hydroxy-2-methyl-2-(methylsulfonyl)butanamide | 0.000714 | ≥64 | 32 | ≥64 | ≥64 | 0.49 | 100 |
| 257 | 4-{4-[(3,5-dimethylbenzyl)oxy]phenyl}-N-hydroxy-2-methyl-2-(methylsulfonyl)butanamide | 0.0045 | ≥64 | 4 | 32 | 32 | 0.56 | 100 |
| 258 | 4-{4-[(2,6-difluorobenzyl)oxy]phenyl}-N-hydroxy-2-methyl-2-(methylsulfonyl)butanamide | 0.000599 | 32 | 2 | 16 | 2 | 0.48 | 100 |
| 259 | 4-(4-{[3-(2-fluoro-5-methoxyphenyl)-1,2,4-oxadiazol-5-yl]methoxy}phenyl)-N-hydroxy-2-methyl-2-(methylsulfonyl)butanamide | 0.00639 | ≥64 | 16 | ≥64 | ≥64 | 0.5 | 100 |
| 260 | N-hydroxy-2-methyl-4-{4-[(2-methylbenzyl)oxy]phenyl}-2-(methylsulfonyl)butanamide | 0.00145 | 32 | 16 | ≥64 | 8 | na | na |
| 261 | N-hydroxy-2-methyl-2-(methylsulfonyl)-4-[4-(tetrahydro-2H-pyran-4-ylmethoxy)phenyl]butanamide | 0.00493 | ≥64 | ≥64 | ≥64 | 32 | 0.43 | 100 |
| 262 | 4-{4-[(2-fluoro-3-methylbenzyl)oxy]phenyl}-N-hydroxy-2-methyl-2-(methylsulfonyl)butanamide | 0.000525 | 16 | 1 | 8 | 2 | 0.54 | 100 |
| 263 | N-hydroxy-2-methyl-4-{4-[(4-methylbenzyl)oxy]phenyl}-2-(methylsulfonyl)butanamide | 0.00102 | 16 | 2 | 8 | 4 | 0.54 | 100 |
| 264 | N-hydroxy-2-methyl-2-(methylsulfonyl)-4-[4-(3-phenylpropoxy)phenyl]butanamide | 0.0102 | 8 | 4 | 16 | 32 | 0.55 | 100 |

TABLE 3-continued

| Example | IUPAC NAME | PA LpxC enzyme IC$^{50}$ μM | AB-3167 MIC | EC-1 MIC | KP-3700 MIC | PA-7 MIC | Ret. time | LCMS ELSD |
|---|---|---|---|---|---|---|---|---|
| 265 | N-hydroxy-2-methyl-2-(methylsulfonyl)-4-[4-(prop-2-yn-1-yloxy)phenyl]butanamide | 0.105 | ≥64 | ≥64 | ≥64 | 16 | 0.43 | 100 |
| 266 | 4-[4-(cyclobutylmethoxy)phenyl]-N-hydroxy-2-methyl-2-(methylsulfonyl)butanamide | 0.00328 | 32 | 32 | ≥64 | 16 | 0.52 | 100 |
| 267 | N-hydroxy-2-methyl-4-{4-[(4-methylpentyl)oxy]phenyl}-2-(methylsulfonyl)butanamide | 0.00322 | 8 | 8 | ≥64 | 16 | 0.58 | 100 |
| 268 | 4-{4-[(3-fluorobenzyl)oxy]phenyl}-N-hydroxy-2-methyl-2-(methylsulfonyl)butanamide | 0.000834 | 16 | 2 | 8 | 8 | 0.51 | 100 |
| 269 | N-hydroxy-2-methyl-4-(4-{[3-(4-methylphenyl)-1,2,4-oxadiazol-5-yl]methoxy}phenyl)-2-(methylsulfonyl)butanamide | 0.00348 | ≥64 | 4 | ≥64 | ≥64 | 0.52 | 100 |
| 270 | N-hydroxy-2-methyl-4-{4-[(6-methylpyridin-3-yl)methoxy]phenyl}-2-(methylsulfonyl)butanamide | 0.00596 | ≥64 | ≥64 | ≥64 | 32 | 0.29 | 100 |
| 271 | N-hydroxy-2-methyl-2-(methylsulfonyl)-4-[4-(2-phenylethoxy)phenyl]butanamide | 0.00403 | 32 | 16 | ≥64 | ≥64 | 0.53 | 100 |
| 272 | N-hydroxy-2-methyl-4-(4-{[3-(3-methylbutyl)-1,2,4-oxadiazol-5-yl]methoxy}phenyl)-2-(methylsulfonyl)butanamide | 0.00154 | ≥64 | 32 | ≥64 | ≥64 | 399.2 UV-215 m/z 0.52 | 74 |
| 273 | 4-{4-[(3-cyclopentyl-1,2,4-oxadiazol-5-yl)methoxy]phenyl}-N-hydroxy-2-methyl-2-(methylsulfonyl)butanamide | 0.0072 | ≥64 | 16 | 32 | ≥64 | 0.51 | 100 |
| 274 | N-hydroxy-2-methyl-2-(methylsulfonyl)-4-(4-{[3-(trifluoromethoxy)benzyl]oxy}phenyl)butanamide | 0.00271 | 16 | 4 | 16 | 16 | 0.56 | 100 |
| 275 | 4-{4-[(5-cyano-2-fluorobenzyl)oxy]phenyl}-N-hydroxy-2-methyl-2-(methylsulfonyl)butanamide | 0.00136 | ≥64 | ≥64 | ≥64 | 32 | 0.48 | 100 |
| 276 | 4-{4-[(2-chloro-6-fluorobenzyl)oxy]phenyl}-N-hydroxy-2-methyl-2-(methylsulfonyl)butanamide | | 32 | 4 | 16 | 4 | | na |
| 277 | 4-[4-(1,3-benzothiazol-2-ylmethoxy)phenyl]-N-hydroxy-2-methyl-2-(methylsulfonyl)butanamide | 0.000651 | ≥64 | 4 | 16 | 32 | 0.49 | 100 |
| 278 | N-hydroxy-2-methyl-4-(4-{[5-methyl-2-(3-methylphenyl)-1,3-oxazol-4-yl]methoxy}phenyl)-2-(methylsulfonyl)butanamide | 0.0104 | ≥64 | 32 | ≥64 | ≥64 | 0.55 | 100 |
| 279 | N-hydroxy-2-methyl-2-(methylsulfonyl)-4-[4-(quinolin-2-ylmethoxy)phenyl]butanamide | 0.0139 | ≥64 | 16 | ≥64 | ≥64 | 0.39 | 100 |
| 280 | 4-(4-{[5-fluoro-2-(trifluoromethyl)benzyl]oxy}phenyl)-N-hydroxy-2-methyl-2-(methylsulfonyl)butanamide | 0.0138 | 32 | 8 | 32 | 32 | 0.56 | 100 |
| 281 | N-hydroxy-2-methyl-2-(methylsulfonyl)-4-{4-[2-(tetrahydro-2H-pyran-4-yl)ethoxy]phenyl}butanamide | 0.00677 | ≥64 | ≥64 | ≥64 | 32 | 0.39 | 100 |
| 282 | N-hydroxy-2-methyl-2-(methylsulfonyl)-4-[4-(1-phenylethoxy)phenyl]butanamide | 0.00955 | 32 | 8 | ≥64 | ≥64 | na | na |
| 283 | N-hydroxy-2-methyl-4-(4-{[3-(4-methylbenzyl)-1,2,4-oxadiazol-5-yl]methoxy}phenyl)-2-(methylsulfonyl)butanamide | 0.00632 | ≥64 | 16 | ≥64 | ≥64 | na | na |

TABLE 3-continued

| Example | IUPAC NAME | PA LpxC enzyeme IC$^{50}$ μM | AB-3167 MIC | EC-1 MIC | KP-3700 MIC | PA-7 MIC | Ret. time | LCMS ELSD |
|---|---|---|---|---|---|---|---|---|
| 284 | 4-{4-[(2-cyano-4-fluorobenzyl)oxy]phenyl}-N-hydroxy-2-methyl-2-(methylsulfonyl)butanamide | 0.00536 | ≥64 | 32 | ≥64 | ≥64 | na | na |
| 285 | 4-{4-[(2-cyanobenzyl)oxy]phenyl}-N-hydroxy-2-methyl-2-(methylsulfonyl)butanamide | 0.01 | ≥64 | 32 | ≥64 | 32 | na | na |
| 286 | N-hydroxy-2-methyl-4-[4-({3-[(4-methylphenoxy)methyl]-1,2,4-oxadiazol-5-yl}methoxy)phenyl]-2-(methylsulfonyl)butanamide | 0.0119 | ≥64 | 32 | ≥64 | ≥64 | na | na |
| 287 | N-hydroxy-2-methyl-4-{4-[(3-methylpyridin-2-yl)methoxy]phenyl}-2-(methylsulfonyl)butanamide | 0.00314 | ≥64 | ≥64 | ≥64 | 16 | na | na |
| 288 | N-hydroxy-2-methyl-2-(methylsulfonyl)-4-(4-{[4-(trifluoromethoxy)benzyl]oxy}phenyl)butanamide | 0.00153 | 4 | 4 | 8 | 8 | na | na |
| 289 | N-hydroxy-2-methyl-4-(4-{[3-(3-methylbenzyl)-1,2,4-oxadiazol-5-yl]methoxy}phenyl)-2-(methylsulfonyl)butanamide | 0.0104 | ≥64 | 32 | ≥64 | ≥64 | na | na |
| 290 | N-hydroxy-2-methyl-2-(methylsulfonyl)-4-(4-{2-[4-(3-methyl-4H-1,2,4-triazol-4-yl)phenoxy]ethoxy}phenyl)butanamide | 0.00356 | ≥64 | 8 | 32 | ≥64 | na | na |
| 291 | 4-(4-{[3-(2-fluoro-5-methylphenyl)-1,2,4-oxadiazol-5-yl]methoxy}phenyl)-N-hydroxy-2-methyl-2-(methylsulfonyl)butanamide | 0.00927 | ≥64 | 16 | ≥64 | ≥64 | na | na |
| 292 | N-hydroxy-2-methyl-4-[4-(3-methylbutoxy)phenyl]-2-(methylsulfonyl)butanamide | 0.00111 | 16 | 16 | ≥64 | 8 | na | na |
| 293 | N-hydroxy-2-methyl-2-(methylsulfonyl)-4-{4-[(2,4,6-trifluorobenzyl)oxy]phenyl}butanamide | 0.000955 | 32 | 4 | 32 | 4 | na | na |
| 294 | 4-{4-[(2,4-difluorobenzyl)oxy]phenyl}-N-hydroxy-2-methyl-2-(methylsulfonyl)butanamide | 0.000992 | 32 | 4 | 16 | 4 | na | na |
| 295 | N-hydroxy-2-methyl-2-(methylsulfonyl)-4-{4-[(3-pentyl-1,2,4-oxadiazol-5-yl)methoxy]phenyl}butanamide | 0.0125 | ≥64 | 32 | ≥64 | ≥64 | na | na |
| 296 | N-hydroxy-2-methyl-2-(methylsulfonyl)-4-[4-(quinolin-8-ylmethoxy)phenyl]butanamide | 0.0158 | 32 | 8 | 16 | ≥64 | na | na |
| 297 | N-hydroxy-2-methyl-2-(methylsulfonyl)-4-[4-(3-phenoxypropoxy)phenyl]butanamide | 0.0425 | 32 | 16 | ≥64 | ≥64 | na | na |
| 298 | 4-(4-{[3-(3-chlorophenyl)-1,2,4-oxadiazol-5-yl]methoxy}phenyl)-N-hydroxy-2-methyl-2-(methylsulfonyl)butanamide | 0.00166 | 16 | 16 | 32 | 32 | na | na |
| 299 | N-hydroxy-4-(4-{[3-(4-isopropylphenyl)-1,2,4-oxadiazol-5-yl]methoxy}phenyl)-2-methyl-2-(methylsulfonyl)butanamide | 0.00393 | ≥64 | 16 | ≥64 | ≥64 | na | na |
| 300 | 4-{4-[(3-cyclobutyl-1,2,4-oxadiazol-5-yl)methoxy]phenyl}-N-hydroxy-2-methyl-2-(methylsulfonyl)butanamide | 0.00756 | ≥64 | 16 | 32 | 32 | na | na |

TABLE 3-continued

| Example | IUPAC NAME | PA LpxC enzyeme IC$^{50}$ μM | AB-3167 MIC | EC-1 MIC | KP-3700 MIC | PA-7 MIC | Ret. time | LCMS ELSD |
|---|---|---|---|---|---|---|---|---|
| 301 | N-hydroxy-2-methyl-2-(methylsulfonyl)-4-(4-{[4-(trifluoromethyl)benzyl]oxy}phenyl)butanamide | 0.00208 | 4 | 4 | 8 | 8 | na | na |
| 302 | 4-(4-{[2-(3-fluorophenyl)-5-methyl-1,3-oxazol-4-yl]methoxy}phenyl)-N-hydroxy-2-methyl-2-(methylsulfonyl)butanamide | 0.0125 | ≥64 | 16 | ≥64 | ≥64 | na | na |
| 303 | N-hydroxy-2-methyl-2-(methylsulfonyl)-4-[4-(pyridin-3-ylmethoxy)phenyl]butanamide | 0.00458 | ≥64 | ≥64 | ≥64 | 16 | na | na |
| 304 | N-hydroxy-2-methyl-2-(methylsulfonyl)-4-(4-{[4-(1H-pyrazol-1-yl)benzyl]oxy}phenyl)butanamide | 0.00199 | 32 | 4 | 16 | 16 | na | na |
| 305 | N-hydroxy-2-methyl-2-(methylsulfonyl)-4-{4-[(3-pyridin-3-yl-1,2,4-oxadiazol-5-yl)methoxy]phenyl}butanamide | 0.00753 | ≥64 | 32 | ≥64 | 32 | na | na |
| 306 | 4-{4-[(2-ethylbenzyl)oxy]phenyl}-N-hydroxy-2-methyl-2-(methylsulfonyl)butanamide | 0.000813 | 16 | 8 | 32 | 16 | na | na |
| 307 | 4-{4-[(4-chloro-2-fluorobenzyl)oxy]phenyl}-N-hydroxy-2-methyl-2-(methylsulfonyl)butanamide | 0.000393 | 16 | 2 | 8 | 4 | na | na |
| 308 | N-hydroxy-2-methyl-2-(methylsulfonyl)-4-{4-[(3-phenyl-1,2,4-oxadiazol-5-yl)methoxy]phenyl}butanamide | 0.00256 | ≥64 | 4 | 16 | 32 | na | na |
| 309 | N-hydroxy-2-methyl-2-(methylsulfonyl)-4-(4-{[4-(methylsulfonyl)benzyl]oxy}phenyl)butanamide | 0.00121 | ≥64 | 8 | 16 | 8 | na | na |
| 310 | N-hydroxy-2-methyl-4-{4-[(3-methylbenzyl)oxy]phenyl}-2-(methylsulfonyl)butanamide | 0.000883 | 16 | 2 | 8 | 4 | na | na |
| 311 | N-hydroxy-2-methyl-2-(methylsulfonyl)-4-[4-(2-pyridin-4-ylethoxy)phenyl]butanamide | 0.0137 | ≥64 | ≥64 | ≥64 | 32 | 0.24 | 100 |
| 312 | 4-[4-(2-cyclopentylethoxy)phenyl]-N-hydroxy-2-methyl-2-(methylsulfonyl)butanamide | 0.00127 | 2 | 8 | ≥64 | 8 | 0.54 | 100 |
| 313 | 4-[4-(3-cyclopentylpropoxy)phenyl]-N-hydroxy-2-methyl-2-(methylsulfonyl)butanamide | 0.00255 | 2 | 4 | 16 | 16 | 0.57 | 100 |
| 314 | 4-[4-(2-cyclohexylethoxy)phenyl]-N-hydroxy-2-methyl-2-(methylsulfonyl)butanamide | 0.00279 | 2 | 16 | ≥64 | 16 | 0.57 | 100 |
| 315 | 4-[4-(3-cyclohexylpropoxy)phenyl]-N-hydroxy-2-methyl-2-(methylsulfonyl)butanamide | 0.00456 | 2 | 4 | 16 | 32 | 0.6 | 100 |
| 316 | N-hydroxy-2-methyl-2-(methylsulfonyl)-4-[4-(pyridin-4-ylmethoxy)phenyl]butanamide | | 16 | 32 | ≥64 | 8 | na | na |

What is claimed is:

1. A compound selected from the group consisting of (2R)-4-(4'-cyanobiphenyl-4-yl)-N-hydroxy-2-methyl-2-(methylsulfonyl)butanamide;

(2R)-4-(4'-fluorobiphenyl-4-yl)-N-hydroxy-2-methyl-2-(methylsulfonyl)butanamide;

4-(2'-fluorobiphenyl-4-yl)-N-hydroxy-2-methyl-2-(methylsulfonyl)butanamide;

N-hydroxy-4-(4'-methoxybiphenyl-4-yl)-2-methyl-2-(methylsulfonyl)butanamide;

N-hydroxy-4-[4-(1H-indol-5-yl)phenyl]-2-methyl-2-(methylsulfonyl)butanamide;

4-[4-(5-cyano-2-thienyl)phenyl]-N-hydroxy-2-methyl-2-(methylsulfonyl)butanamide;

(2R)-4-[4-(1,3-benzodioxol-5-yl)phenyl]-N-hydroxy-2-methyl-2-(methylsulfonyl)butanamide;

(2R)—N-hydroxy-4-[4-(1H-indol-2-yl)phenyl]-2-methyl-2-(methylsulfonyl)butanamide;
(2R)-4-biphenyl-4-yl-N-hydroxy-2-methyl-2-(methylsulfonyl)butanamide;
4-(2,4'-difluorobiphenyl-4-yl)-N-hydroxy-2-methyl-2-(methylsulfonyl)butanamide;
(2R)-4-(4'-glycoloylbiphenyl-4-yl)-N-hydroxy-2-methyl-2-(methylsulfonyl)butanamide;
(2R)—N-hydroxy-4-[4-(6-methoxypyridin-3-yl)phenyl]-2-methyl-2-(methylsulfonyl)butanamide;
4-[4-(3,6-dihydro-2H-thiopyran-4-yl)phenyl]-N-hydroxy-2-methyl-2-(methylsulfonyl)butanamide;
4-(4'-cyano-3-fluorobiphenyl-4-yl)-N-hydroxy-2-methyl-2-(methylsulfonyl)butanamide;
N-hydroxy-4-[4'-(4-hydroxybutoxy)biphenyl-4-yl]-2-methyl-2-(methylsulfonyl)butanamide;
(2R)—N-hydroxy-4-(4'-hydroxybiphenyl-4-yl)-2-methyl-2-(methylsulfonyl)butanamide;
4-[4-(benzyloxy)phenyl]-N-hydroxy-2-methyl-2-(methylsulfonyl)butanamide;
(2R)—N-hydroxy-2-methyl-2-(methylsulfonyl)-4-[4'-(3-morpholin-4-ylpropoxy)biphenyl-4-yl]butanamide;
4-[3-fluoro-4-(6-methoxypyridin-3-yl)phenyl]-N-hydroxy-2-methyl-2-(methylsulfonyl)butanamide;
4-(4-cyclohex-1-en-1-ylphenyl)-N-hydroxy-2-methyl-2-(methylsulfonyl)butanamide;
N-hydroxy-2-methyl-2-(methylsulfonyl)-4-[4-(4-methyl-2-thienyl)phenyl]butanamide;
4-(3-fluoro-4-quinolin-6-ylphenyl)-N-hydroxy-2-methyl-2-(methylsulfonyl)butanamide; and
4'-[(3R)-4-(hydroxyamino)-3-methyl-3-(methylsulfonyl)-4-oxobutyl]biphenyl-4-yl dihydrogen phosphate;
or a pharmaceutically acceptable salt thereof.

2. A pharmaceutical composition comprising a compound selected from the group consisting of
(2R)-4-(4'-cyanobiphenyl-4-yl)-N-hydroxy-2-methyl-2-(methylsulfonyl)butanamide;
(2R)-4-(4'-fluorobiphenyl-4-yl)-N-hydroxy-2-methyl-2-(methylsulfonyl)butanamide;
4-(2'-fluorobiphenyl-4-yl)-N-hydroxy-2-methyl-2-(methylsulfonyl)butanamide;
N-hydroxy-4-(4'-methoxybiphenyl-4-yl)-2-methyl-2-(methylsulfonyl)butanamide;
N-hydroxy-4-[4-(1H-indol-5-yl)phenyl]-2-methyl-2-(methylsulfonyl)butanamide;
4-[4-(5-cyano-2-thienyl)phenyl]-N-hydroxy-2-methyl-2-(methylsulfonyl)butanamide;
(2R)-4-[4-(1,3-benzodioxol-5-yl)phenyl]-N-hydroxy-2-methyl-2-(methylsulfonyl)butanamide;
(2R)—N-hydroxy-4-[4-(1H-indol-2-yl)phenyl]-2-methyl-2-(methylsulfonyl)butanamide;
(2R)-4-biphenyl-4-yl-N-hydroxy-2-methyl-2-(methylsulfonyl)butanamide;
4-(2,4'-difluorobiphenyl-4-yl)-N-hydroxy-2-methyl-2-(methylsulfonyl)butanamide;
(2R)-4-(4'-glycoloylbiphenyl-4-yl)-N-hydroxy-2-methyl-2-(methylsulfonyl)butanamide;
(2R)—N-hydroxy-4-[4-(6-methoxypyridin-3-yl)phenyl]-2-methyl-2-(methylsulfonyl)butanamide;
4-[4-(3,6-dihydro-2H-thiopyran-4-yl)phenyl]-N-hydroxy-2-methyl-2-(methylsulfonyl)butanamide;
4-(4'-cyano-3-fluorobiphenyl-4-yl)-N-hydroxy-2-methyl-2-(methylsulfonyl)butanamide;
N-hydroxy-4-[4'-(4-hydroxybutoxy)biphenyl-4-yl]-2-methyl-2-(methylsulfonyl)butanamide;
(2R)—N-hydroxy-4-(4'-hydroxybiphenyl-4-yl)-2-methyl-2-(methylsulfonyl)butanamide;
4-[4-(benzyloxy)phenyl]-N-hydroxy-2-methyl-2-(methylsulfonyl)butanamide;
(2R)—N-hydroxy-2-methyl-2-(methylsulfonyl)-4-[4'-(3-morpholin-4-ylpropoxy)biphenyl-4-yl]butanamide;
4-[3-fluoro-4-(6-methoxypyridin-3-yl)phenyl]-N-hydroxy-2-methyl-2-(methylsulfonyl)butanamide;
4-(4-cyclohex-1-en-1-ylphenyl)-N-hydroxy-2-methyl-2-(methylsulfonyl)butanamide;
N-hydroxy-2-methyl-2-(methylsulfonyl)-4-[4-(4-methyl-2-thienyl)phenyl]butanamide;
4-(3-fluoro-4-quinolin-6-ylphenyl)-N-hydroxy-2-methyl-2-(methylsulfonyl)butanamide; and
4'-[(3R)-4-(hydroxyamino)-3-methyl-3-(methylsulfonyl)-4-oxobutyl]biphenyl-4-yl dihydrogen phosphate;
or a pharmaceutically acceptable salt thereof;
in admixture with at least one pharmaceutically acceptable excipient.

3. A method of treating a gram negative bacterial infection in a patient, the method comprising administering a therapeutically effective amount of a compound selected from the group consisting of
(2R)-4-(4'-cyanobiphenyl-4-yl)-N-hydroxy-2-methyl-2-(methylsulfonyl)butanamide;
(2R)-4-(4'-fluorobiphenyl-4-yl)-N-hydroxy-2-methyl-2-(methylsulfonyl)butanamide;
4-(2'-fluorobiphenyl-4-yl)-N-hydroxy-2-methyl-2-(methylsulfonyl)butanamide;
N-hydroxy-4-(4'-methoxybiphenyl-4-yl)-2-methyl-2-(methylsulfonyl)butanamide;
N-hydroxy-4-[4-(1H-indol-5-yl)phenyl]-2-methyl-2-(methylsulfonyl)butanamide;
4-[4-(5-cyano-2-thienyl)phenyl]-N-hydroxy-2-methyl-2-(methylsulfonyl)butanamide;
(2R)-4-[4-(1,3-benzodioxol-5-yl)phenyl]-N-hydroxy-2-methyl-2-(methylsulfonyl)butanamide;
(2R)—N-hydroxy-4-[4-(1H-indol-2-yl)phenyl]-2-methyl-2-(methylsulfonyl)butanamide;
(2R)-4-biphenyl-4-yl-N-hydroxy-2-methyl-2-(methylsulfonyl)butanamide;
4-(2,4'-difluorobiphenyl-4-yl)-N-hydroxy-2-methyl-2-(methylsulfonyl)butanamide;
(2R)-4-(4'-glycoloylbiphenyl-4-yl)-N-hydroxy-2-methyl-2-(methylsulfonyl)butanamide;
(2R)—N-hydroxy-4-[4-(6-methoxypyridin-3-yl)phenyl]-2-methyl-2-(methylsulfonyl)butanamide;
4-[4-(3,6-dihydro-2H-thiopyran-4-yl)phenyl]-N-hydroxy-2-methyl-2-(methylsulfonyl)butanamide;
4-(4'-cyano-3-fluorobiphenyl-4-yl)-N-hydroxy-2-methyl-2-(methylsulfonyl)butanamide;
N-hydroxy-4-[4'-(4-hydroxybutoxy)biphenyl-4-yl]-2-methyl-2-(methylsulfonyl)butanamide;
(2R)—N-hydroxy-4-(4'-hydroxybiphenyl-4-yl)-2-methyl-2-(methylsulfonyl)butanamide;
4-[4-(benzyloxy)phenyl]-N-hydroxy-2-methyl-2-(methylsulfonyl)butanamide;
(2R)—N-hydroxy-2-methyl-2-(methylsulfonyl)-4-[4'-(3-morpholin-4-ylpropoxy)biphenyl-4-yl]butanamide;
4-[3-fluoro-4-(6-methoxypyridin-3-yl)phenyl]-N-hydroxy-2-methyl-2-(methylsulfonyl)butanamide;
4-(4-cyclohex-1-en-1-ylphenyl)-N-hydroxy-2-methyl-2-(methylsulfonyl)butanamide;
N-hydroxy-2-methyl-2-(methylsulfonyl)-4-[4-(4-methyl-2-thienyl)phenyl]butanamide;
4-(3-fluoro-4-quinolin-6-ylphenyl)-N-hydroxy-2-methyl-2-(methylsulfonyl)butanamide; and
4'-[(3R)-4-(hydroxyamino)-3-methyl-3-(methylsulfonyl)-4-oxobutyl]biphenyl-4-yl dihydrogen phosphate;

or a pharmaceutically acceptable salt thereof to a patient in need thereof.

4. The method according to claim 3 wherein the gram negative bacterial infection is an *Acinetobacter baumannii, Acinetobacter* spp., *Enterobacter aerogenes, Enterobacter clocae, Escherichia coli, Klebsiella oxytoca, Klebsiella pneumonia, Serratia marcescens* or *Pseudomonas aeruginosa* infection.

5. The method according to claim 4 wherein the gram negative bacterial infection is an *Acinetobacter baumannii, Escherichia coli, Klebsiella pneumonia* or *Pseudomonas aeruginosa* infection.

\* \* \* \* \*